(12) United States Patent
Cirillo et al.

(10) Patent No.: US 9,138,490 B2
(45) Date of Patent: Sep. 22, 2015

(54) USE OF BACTERIAL BETA-LACTAMASE FOR IN VITRO DIAGNOSTICS AND IN VIVO IMAGING, DIAGNOSTICS AND THERAPEUTICS

(71) Applicants: Jeffrey D. Cirillo, College Station, TX (US); James C. Sacchettini, College Station, TX (US); Jianghong Rao, Sunnyvale, CA (US); Hexin Xie, Mountain View, CA (US)

(72) Inventors: Jeffrey D. Cirillo, College Station, TX (US); James C. Sacchettini, College Station, TX (US); Jianghong Rao, Sunnyvale, CA (US); Hexin Xie, Mountain View, CA (US)

(73) Assignees: The Texas A&M University System, College Station, TX (US); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/693,706

(22) Filed: Dec. 4, 2012

(65) Prior Publication Data

US 2013/0164221 A1    Jun. 27, 2013

Related U.S. Application Data

(63) Continuation of application No. PCT/US2011/001018, filed on Jun. 3, 2011, which is a continuation-in-part of application No. 12/802,340, filed on Jun. 4, 2010, now abandoned, which is a continuation-in-part of application No. 12/462,644, filed on Aug. 6, 2009, now abandoned.

(60) Provisional application No. 61/203,605, filed on Dec. 24, 2008, provisional application No. 61/188,112, filed on Aug. 6, 2008.

(51) Int. Cl.
| | |
|---|---|
| *G01N 21/64* | (2006.01) |
| *A61K 49/00* | (2006.01) |
| *C12Q 1/04* | (2006.01) |
| *C12Q 1/34* | (2006.01) |

(52) U.S. Cl.
CPC .......... *A61K 49/0021* (2013.01); *A61K 49/0028* (2013.01); *A61K 49/0032* (2013.01); *A61K 49/0041* (2013.01); *A61K 49/0052* (2013.01); *C12Q 1/04* (2013.01); *C12Q 1/34* (2013.01); *G01N 21/6486* (2013.01); *G01N 2333/986* (2013.01)

(58) Field of Classification Search
None
See application file for complete search history.

(56) References Cited

U.S. PATENT DOCUMENTS 7,396,926 B2 *   7/2008   Tsien et al. ............. 540/229

FOREIGN PATENT DOCUMENTS

EP         553741 A2    8/1993

OTHER PUBLICATIONS

Brook et al., Bacterial interference in the nasopharynx following antimicrobial therapy of acute otitis media, 1998, Journal of Antimicrobial Chemotherapy 41(4): 489-492.*
Brook, Aerobic and anaerobic bacterial flora of normal maxillary sinuses, 1981, The laryngoscope 91(3): 372-376.*
Stjernquist-Desatnik et al., Tonsillar microbial flora: comparison of recurrent tonsillitis and normal tonsils, 1999, Acta Otolaryngologica 119(1): 102-106.*
Tung, Flourescent Peptide Probes for in Vivo Diagnostic Imaging, journal, 2004, p. 391-403, vol. 76 (5), Peptide Science, US.
Giwercman, High-Level beta-Lactamase Activity in Sputum Samples from Cystic Fibrosis Patients during Antipseudomonal Treatment, journal, 1992, p. 71-76, vol. 36 (1), Antimicrobial Agents and Chemotherapy, US.
Ntziachristos, Visualization of antitumor treatment by means of fluorescence molecular tomography with an annexin V-Cy5.5 conjugate, journal, 2004, p. 12294-12299, vol. 101(33), PNAS, US.
Raynaud, Extracellular enzyme activities potentially involved in the pathogenicity of *Mycobacterium tuberculosis*, journal, 1998, p. 577-587, vol. 144, Microbiology, US.
Xing, Raymond, Cell-Permeable Near-Infrared Fluorogenic substrates for Imaging beta-Lactamase Activity, JACSociety 2005, vol. 127, issue 12, 4158-4159.
McCann et al., Microbiology, 2007, 153, pp. 3350-3359.

* cited by examiner

*Primary Examiner* — Robert Yamasaki
(74) *Attorney, Agent, or Firm* — Benjamin Aaron Adler

(57) ABSTRACT

Provided herein are methods for detecting, quantifying, differentiating, diagnosing and imaging pathogenic bacteria or condition associated therewith using substrates for bacterial enzymes. Fluorescent, luminescent or colorimetric signals emitted by substrates or enzyme products in the presence of the bacteria are compared to controls to detect and locate the pathogenic bacteria. Provided is a method for screening therapeutic agents to treat the pathophysiological conditions by measuring a signal emitted from the substrates or products in the presence and absence of the potential therapeutic agent and a diagnostic method for detecting a mycobacterial infection in a subject by contacting biological samples with a substrate and imaging for signals emitted from a mycobacterial beta-lactamase product. Also provided are fluorogenic substrates or substrates comprising a colored dye or a chemical reagent effective to induce a color or pH change.

8 Claims, 60 Drawing Sheets

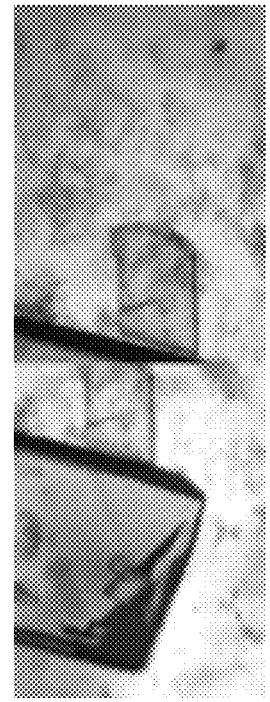
FIG. 1B
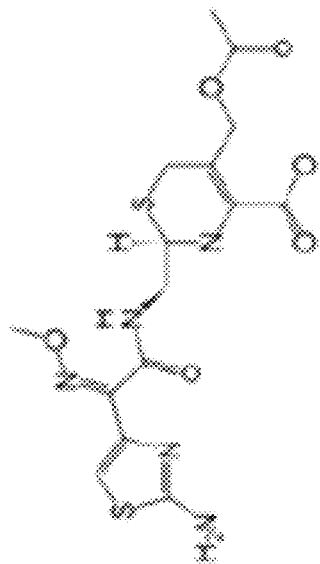
Cefotaxime product
FIG. 1C
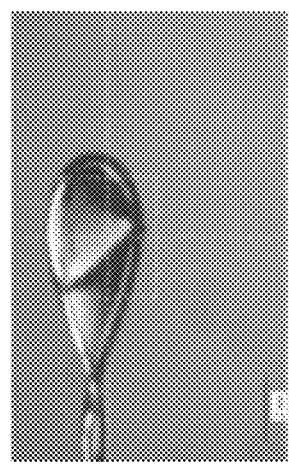
FIG. 1A
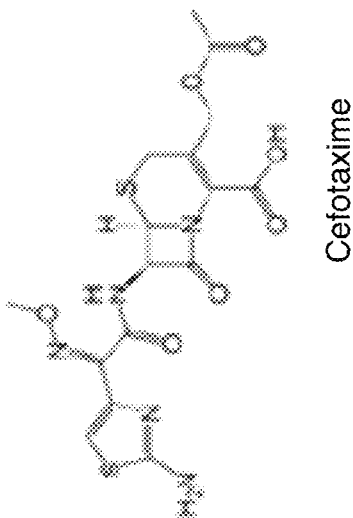
Cefotaxime QSY22 disulfonate
690 nm QSY21 disulfonate
675 nm QSY21
660 nm Abs

CNIR10

XHX2-81

XHX2-91

XHX3-26

XHX3-32

XHX3-1

CNIR800

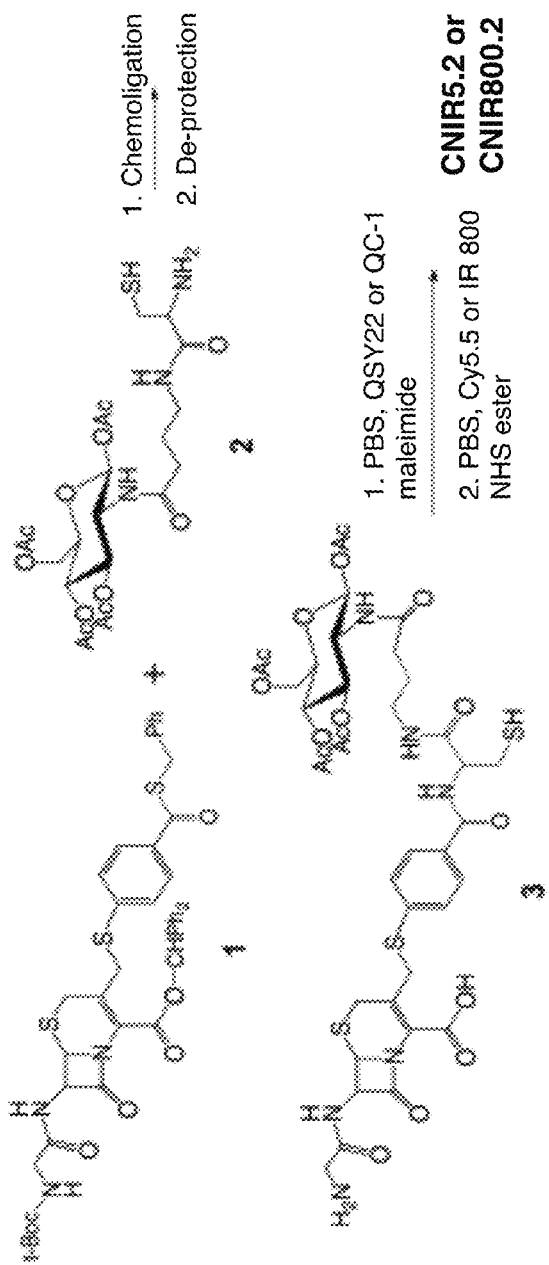
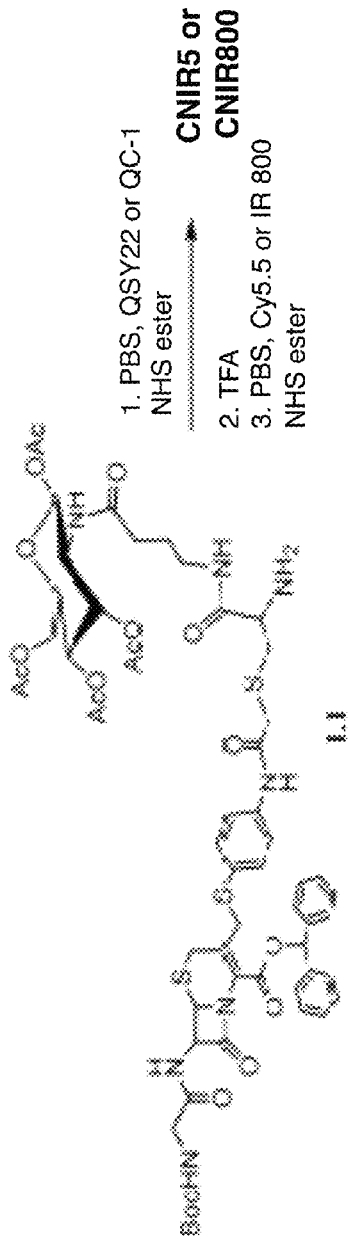
FIG. 11B
FIG. 11C

| | R | R' |
|---|---|---|
| CNIR5.2 | Cy5.5 | QSY22 |
| CNIR800.2 | IR800CW | IRDye QC-1 |

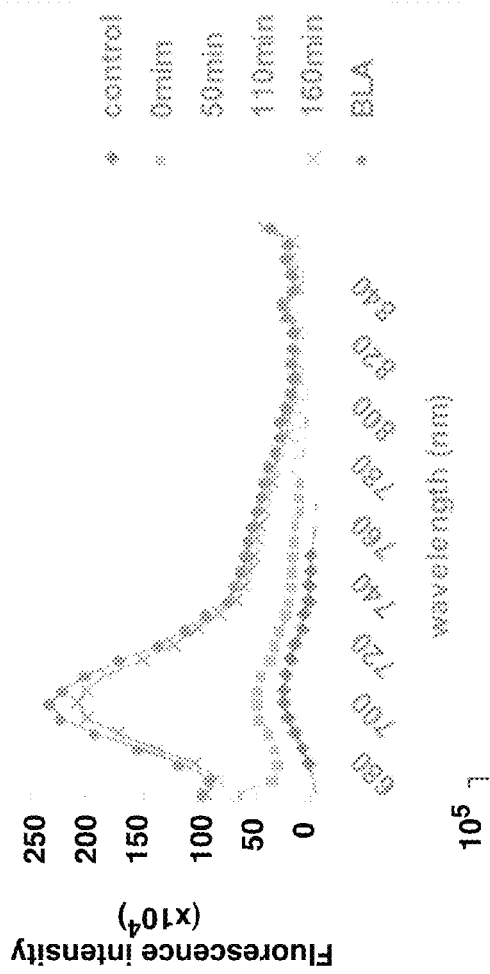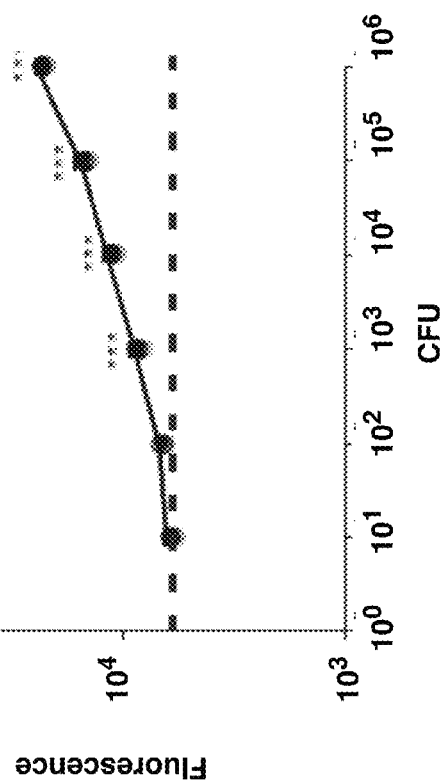
FIG. 12A
FIG. 12B

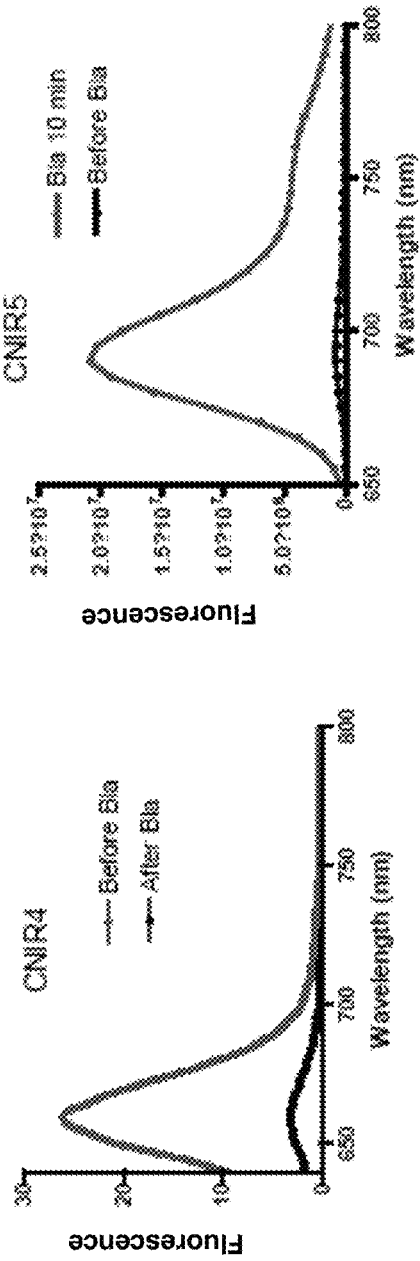
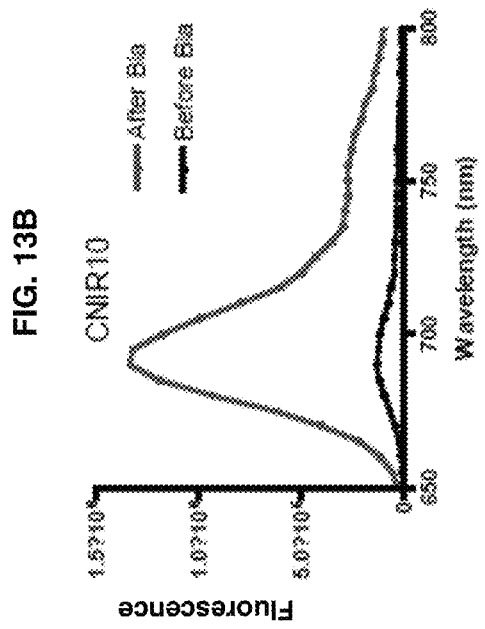
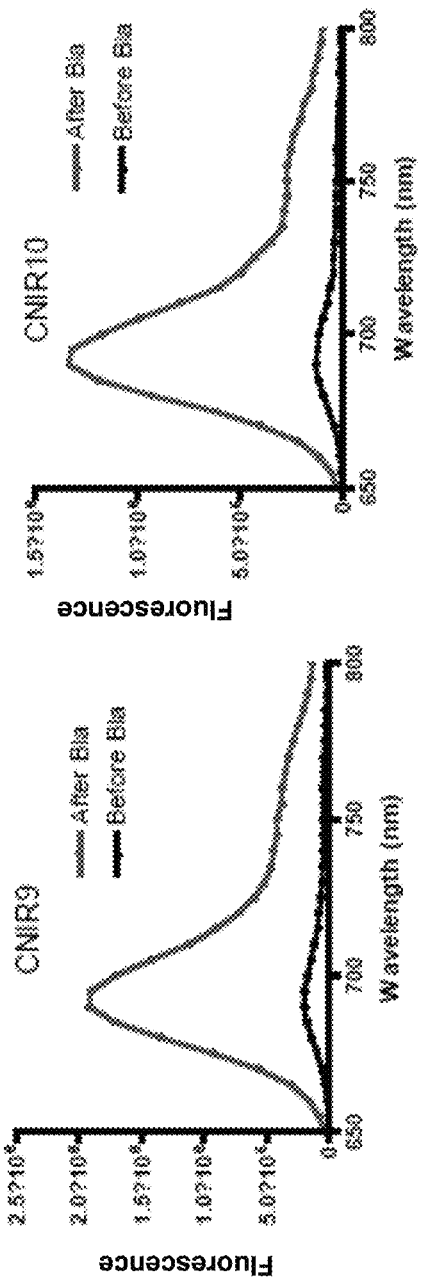
FIG. 13A
FIG. 13B
FIG. 13C
FIG. 13D

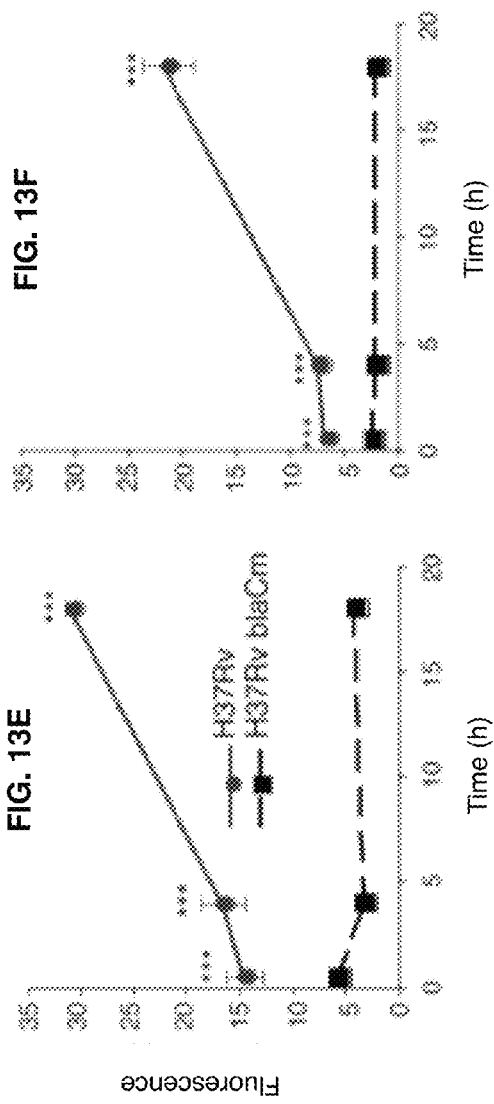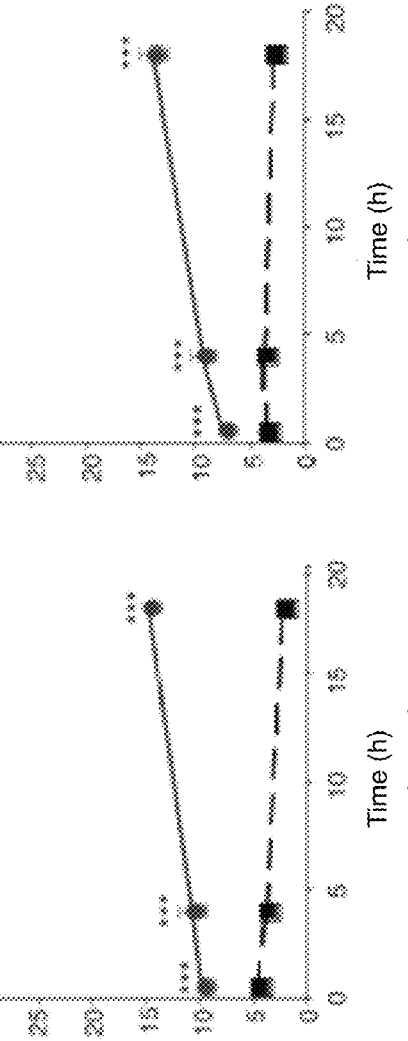

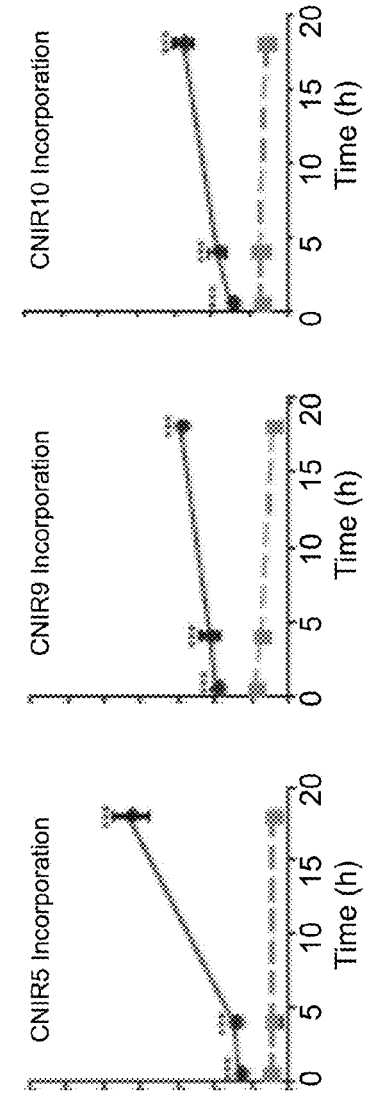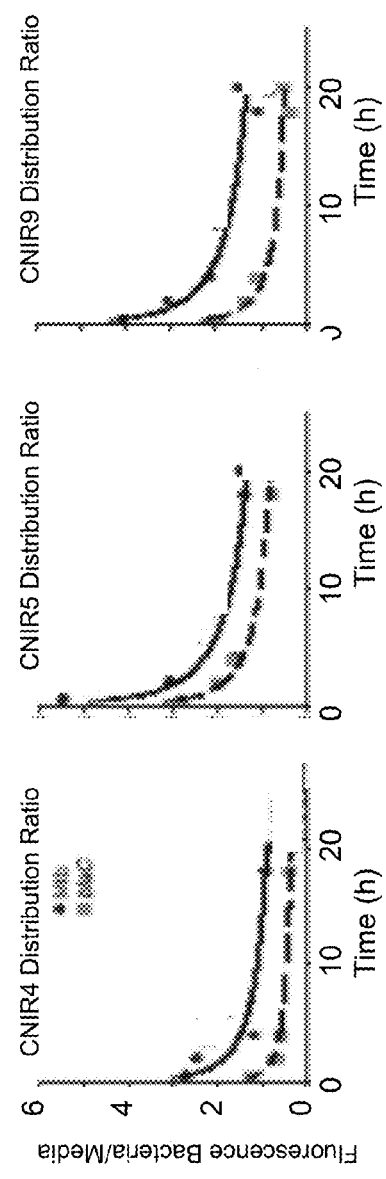

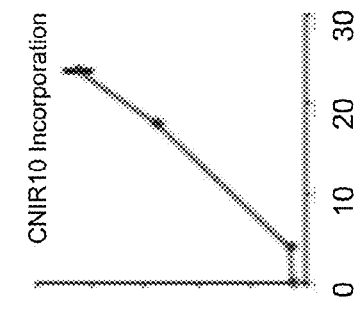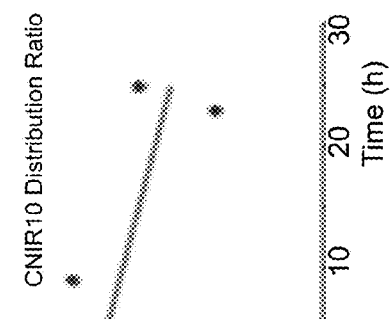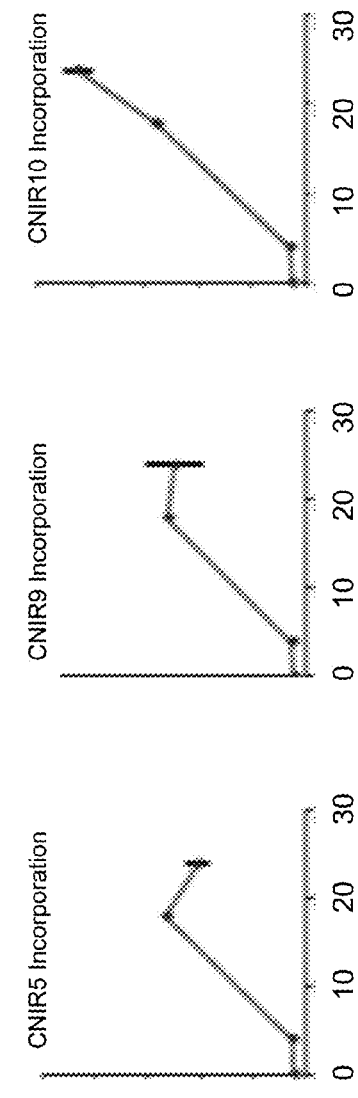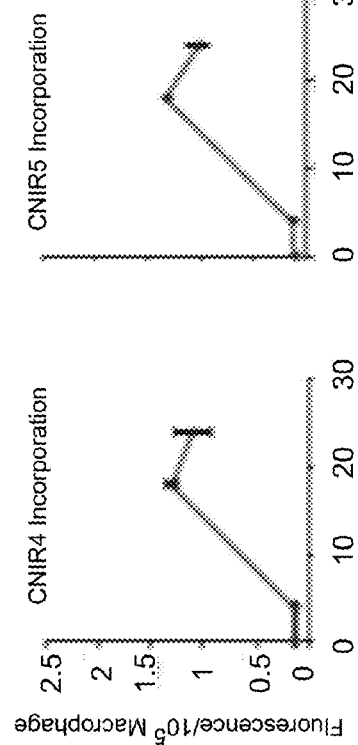

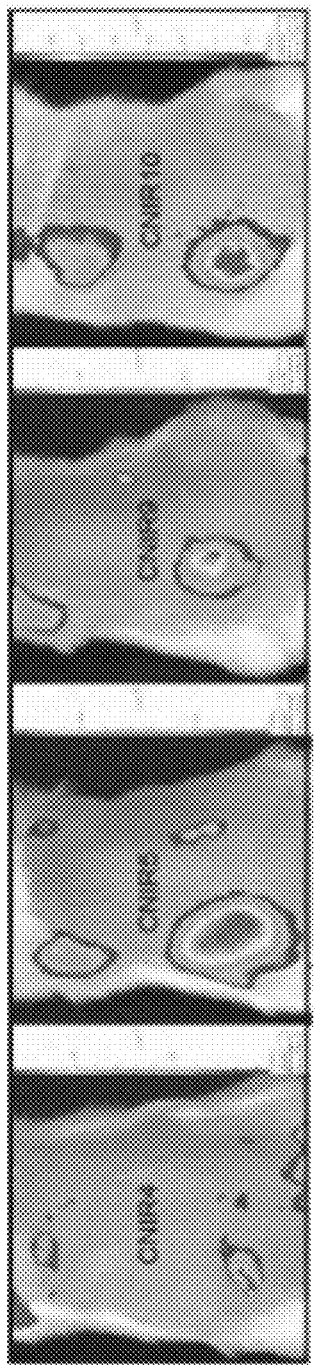
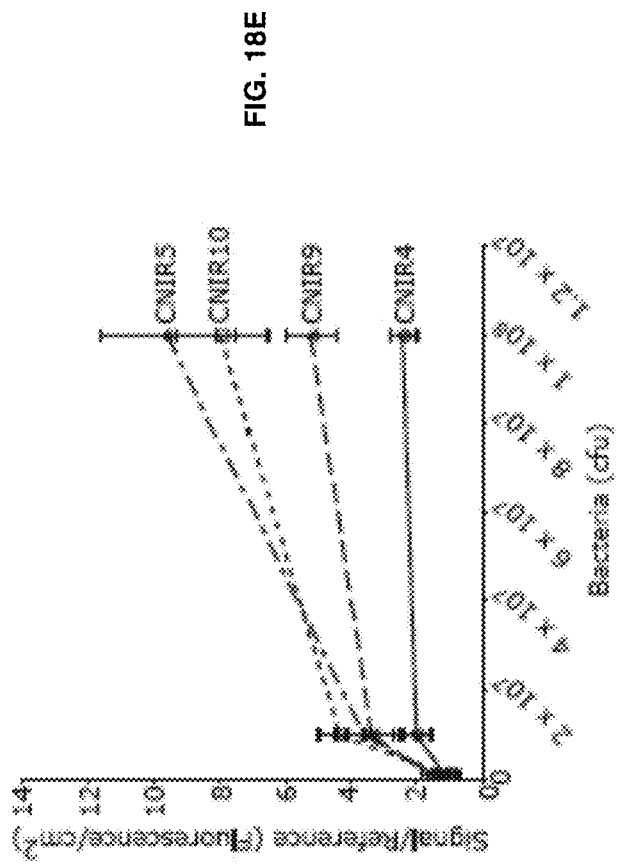
FIG. 18A  FIG. 18B  FIG. 18C  FIG. 18D
FIG. 18E

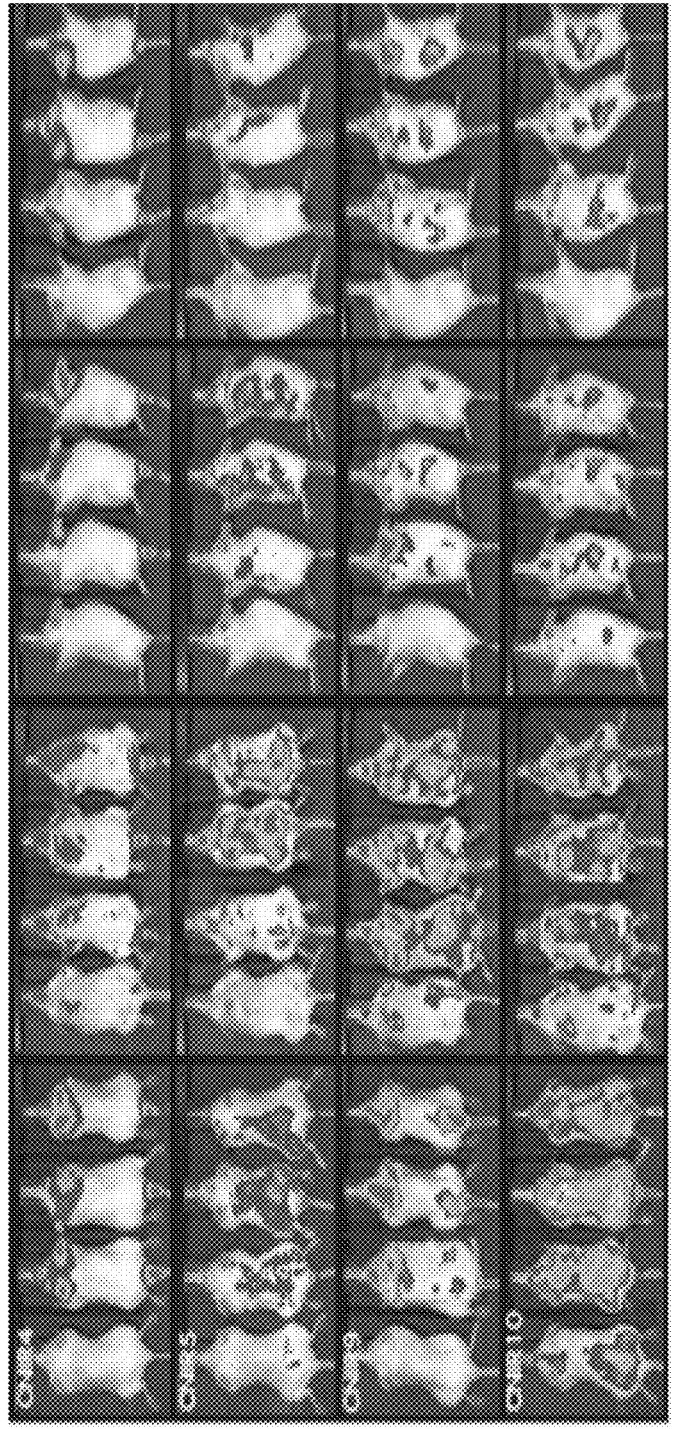

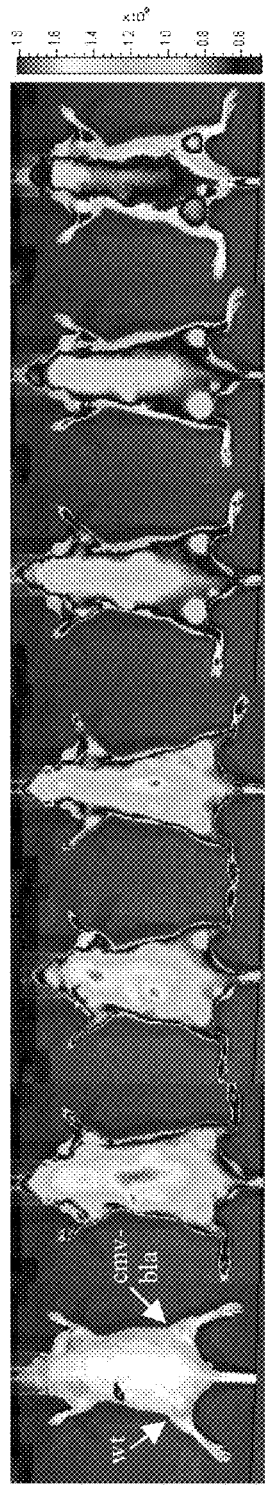
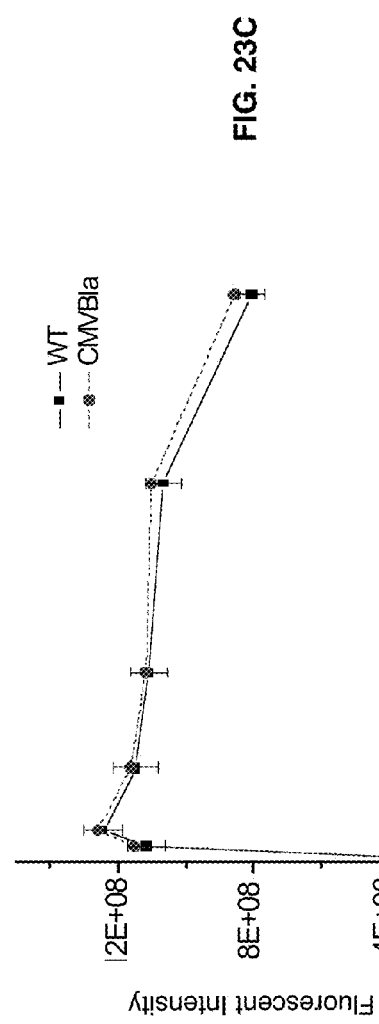
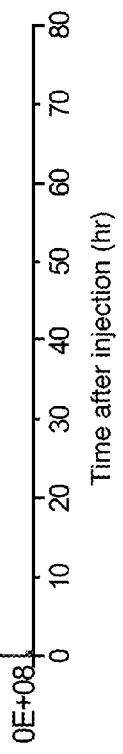
FIG. 23B
FIG. 23C

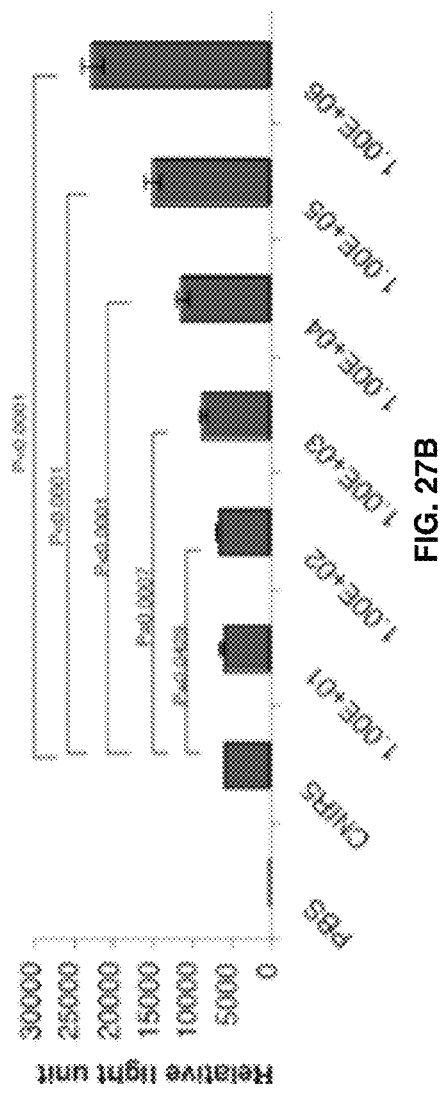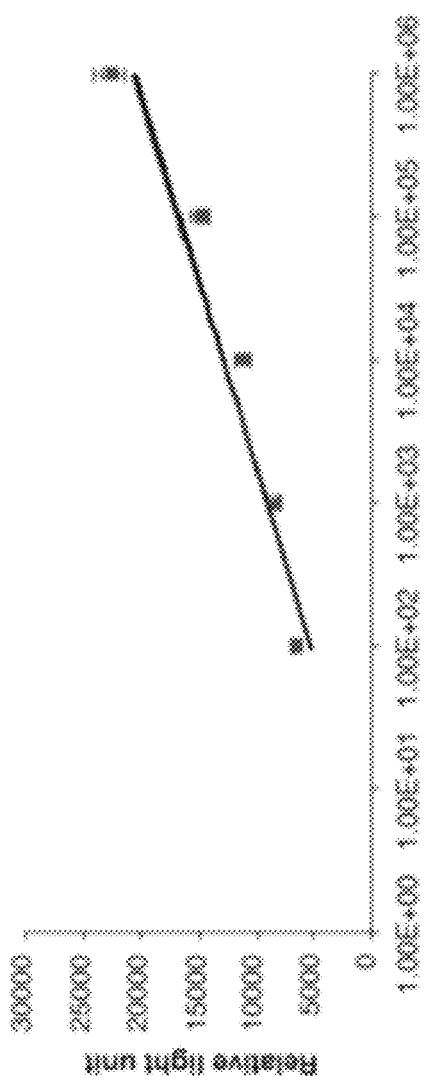
FIG. 27B
FIG. 27C

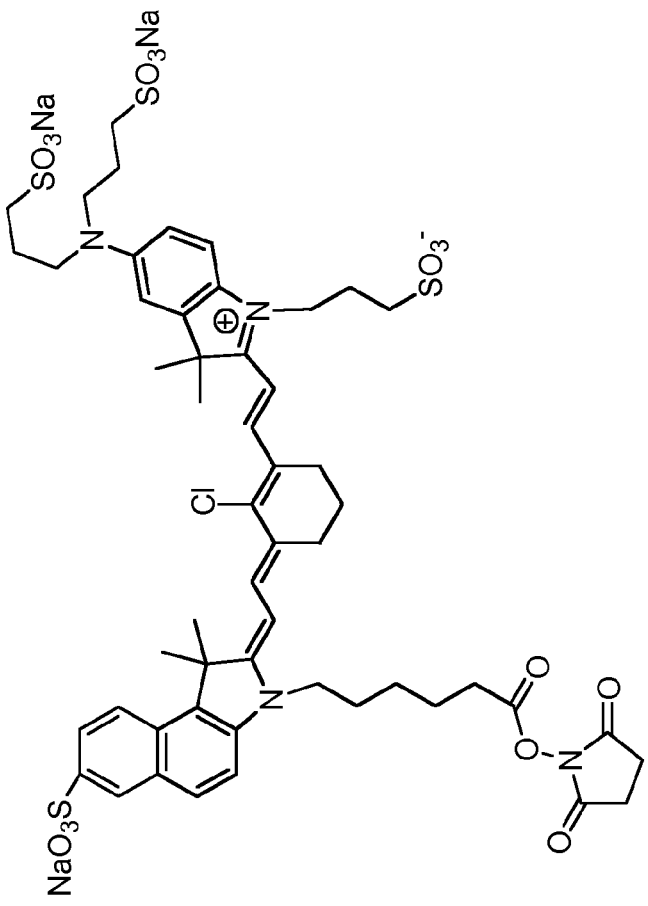
IRDYE QC-1 NHS ester
FIG. 28
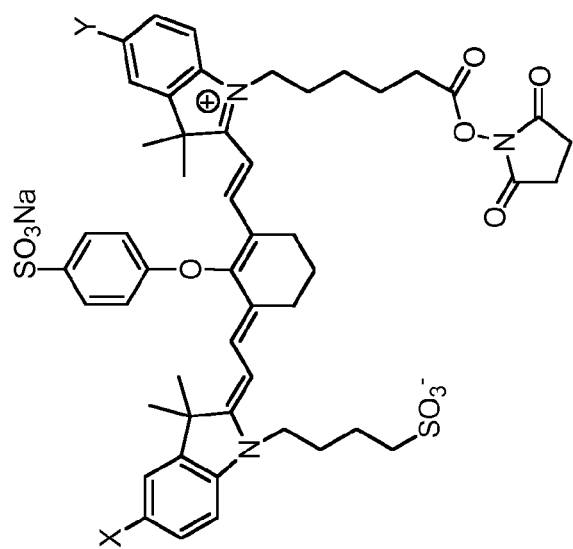
NHS ester of
IRDye 800 CW:   X= SO₃Na,   Y=SO₃Na
IRDye 800RS:    X=H,        Y=H

USE OF BACTERIAL BETA-LACTAMASE FOR IN VITRO DIAGNOSTICS AND IN VIVO IMAGING, DIAGNOSTICS AND THERAPEUTICS

CROSS-REFERENCE TO RELATED APPLICATIONS

This continuation application claims benefit of priority under 35 U.S.C. §120 of pending international application PCT/US2011/001018, filed Jun. 3, 2011, which claims benefit of priority under 35 U.S.C. §120 of pending continuation-in-part patent application U.S. Ser. No. 12/802,340, filed Jun. 4, 2010, which claims benefit of priority under 35 U.S.C. §120 of pending non-provisional U.S. Ser. No. 12/462,644, filed Aug. 6, 2009, which claims benefit of priority under 35 U.S.C. §119(e) of provisional U.S. Ser. No. 61/203,605, filed Dec. 24, 2008, and of provisional U.S. Ser. No. 61/188,112, filed Aug. 6, 2008, the entirety of all of which are herein incorporated by reference.

BACKGROUND OF THE INVENTION

1. Field of the Invention

The present invention relates generally to the fields of medicine, pathogenic microbiology and imaging technologies. More specifically, the present invention relates to compounds and reporters useful to detect and locate bacterial pathogens during in vitro or in vivo imaging of a subject.

2. Description of the Related Art

Numerous bacterial infections cause significant morbidity and mortality throughout the world and many of the most important bacterial species are beta-lactamase positive, making them resistant to standard penicillin-like antibiotics. Diagnosis of many of these infections and the presence of penicillin resistance is often difficult and requires extensive diagnostic laboratory culturing prior to susceptibility determination.

For example, tuberculosis currently affects nearly one-third of the world's population and remains a critical public health threat. Concern is greatly heightened when one considers the continued presence of multiple drug resistant and extensively drug resistant strains worldwide, which are not readily treatable. Current methods to quantify and assess the viability of tuberculosis in the laboratory, tissue culture cells and during infection in animal models and humans are limited to determination of colony forming units (CFU) and/or microscopy of tissues and sputum. These methods are time-consuming, often difficult to interpret and relatively insensitive. Most methods require invasive procedures that, in the case of animals and humans, must be carried out postmortem. These inadequacies make it difficult to follow disease progression, vaccine efficacy and therapeutic outcome, both in animal models and patients. Optical imaging methods would allow direct observation of tuberculosis viability during infection, efficacy of therapeutics and localization of bacteria during disease in real-time using live animals in a non-invasive manner.

Thus, there is a recognized need in the art for improved methods for imaging and diagnosing bacterial disease. More specifically, the prior art is deficient in sensitive and specific real-time optical imaging methods for beta-lactamase positive bacteria that can be used in vitro and in live subjects to diagnose and locate the bacterial infection, to rapidly screen for new therapeutics and to identify new drug targets. The present invention fulfills this long-standing need and desire in the art.

SUMMARY OF THE INVENTION

The present invention is directed to a method for detecting a pathogenic bacteria in real time in a subject. The method comprises introducing into the subject or a biological sample therefrom a fluorescent, luminescent or colorimetric substrate for a beta-lactamase of the pathogenic bacteria and imaging the subject or sample for a product from beta-lactamase activity on the substrate. Signals at a wavelength emitted by the beta-lactamase product are acquired thereby detecting the pathogenic bacteria in the subject. The present invention is directed to a related method further comprising producing a 3D reconstruction of the emitted signal to determine location of the pathogenic bacteria in the subject. The present invention is directed to another related method further comprising diagnosing in real time a pathophysiological condition associated with the pathogenic bacteria based on an emitted signal intensity greater than a measured control signal. For example the fluorescent, luminescent or colorimetric substrate is CNIR2, CNIR3, CNIR4, CNIR5, CNIR5-QSY22, CNIR7, CNIR9, CNIR10, CNIR7-TAT, a caged luciferin, a colorimetric reagent or a derivative or analog thereof.

The present invention is directed to a related method for detecting a pathogenic bacteria in real time. The method comprises introducing into a subject, or contacting a biological sample therefrom or obtained from a surface, with a substrate for a beta-lactamase of the pathogenic bacteria and imaging the subject or sample for a product from beta-lactamase activity on the substrate. Signals at a wavelength emitted by the beta-lactamase product are acquired thereby detecting the pathogenic bacteria in the subject. The present invention is directed to a related method further comprising one or both of the steps of quantifying and differentiating infected cells from non-infected cells in the biological sample. The present invention is directed to another related method further comprising producing a 3D reconstruction of the emitted signal to determine location of the pathogenic bacteria in the subject. For example the substrate may be a fluorogenic substrate CDC-1, CDC-2, CDC-3, CDC-4, CDC-5, CNIR5, CNIR5.2, CNIR5-QSY22, CNIR7, CNIR7-TAT, CNIR9, CNIR10, CNIR800, CNIR800.2, CNIR800-3, XHX2-81, XHX2-91, XHX3-1, XHX3-2, XHX3-26, or XHX3-32 or a derivative or analog thereof or that comprise a colored dye or a chemical reagent effective to produce a color or pH change upon beta-lactamase activity thereon.

The present invention also is directed to a method for diagnosing a pathophysiological condition associated with a pathogenic bacteria in a subject. The method comprises administering to the subject or contacting a biological sample derived therefrom with a fluorogenic or luminescent substrate for a beta-lactamase of the pathogenic bacteria and imaging the subject for a product of beta-lactamase activity on the substrate. A fluorescent, luminescent or colorimetric signal intensity is measured in real time at wavelength emitted by the product such that a fluorescent, luminescent or colorimetric signal intensity greater than a measured control signal correlates to a diagnosis of the pathophysiological condition. The present invention is directed to a related method further comprising producing a 3D reconstruction of the signal to determine location of the microbial pathogen. The present invention is directed to another related method further comprising administering one or more therapeutic compounds effective to treat the pathophysiological condition. The present invention is directed to a further related method comprising readministering the fluorogenic compound to the subject and reimaging the subject or contacting a biological sample derived therefrom with said fluorogenic substrate; and imaging the subject or said biological sample to monitor the efficacy of the therapeutic compound such that a decrease in emitted signal compared to the signal at diagnosis indicates a therapeutic effect on the pathophysiological condition. For example the fluorogenic or luminescent substrate is CNIR2, CNIR3, CNIR4, CNIR5, CNIR5-QSY22, CNIR7, CNIR9, CNIR10, CNIR7-TAT, a caged luciferin, a colorimetric reagent or a derivative or analog thereof.

The present invention is directed to a related method for diagnosing a pathophysiological condition associated with a pathogenic bacteria in a subject. The method comprises administering to the subject or contacting a biological sample derived therefrom with a substrate for a beta-lactamase of the pathogenic bacteria and imaging the subject for a product of beta-lactamase activity on the substrate. A signal intensity, e.g., a fluorescent, luminescent or colorimetric signal, is measured in real time at a wavelength emitted by the product; wherein a signal intensity greater than a measured control signal correlates to a diagnosis of the pathophysiological condition. The present invention is directed to a related method further comprising one or both of the steps of quantifying and differentiating infected cells from non-infected cells in the biological sample. The present invention is directed to another related method further comprising producing a 3D reconstruction of the signal to determine location of the microbial pathogen. Particularly, the substrate may be a fluorogenic substrate CDC-1, CDC-2, CDC-3, CDC-4, CDC-5, CNIR5, CNIR5.2, CNIR5-QSY22, CNIR7, CNIR7-TAT, CNIR9, CNIR10, CNIR800, CNIR800.2, CNIR800-3, XHX2-81, XHX2-91, XHX3-1, XHX3-2, XHX3-26, or XHX3-32 or a derivative or analog thereof comprises a colored dye or a chemical reagent effective to produce a color or pH change upon beta-lactamase activity thereon.

The present invention is directed further to a diagnostic method for detecting a mycobacterial infection in a subject. The method comprises obtaining a biological sample from the subject and contacting the biological sample with a substrate of a mycobacterial beta-lactamase enzyme. The biological sample is imaged to detect a product of beta-lactamase activity on the substrate and a signal intensity is measured at a wavelength emitted by the product, where a signal intensity greater than a measured control signal indicates the presence of the mycobacterial infection. The present invention is directed to a related method further comprising one or both of the steps of quantifying and differentiating infected cells from non-infected cells in the biological sample. The present invention is directed to another related method further comprising repeating these method steps one or more times to monitor therapeutic efficacy of a treatment regimen administered to the subject upon detection of the mycobacterial infection, where a decrease in the measured signal compared to control correlates to a positive response to the treatment regimen. The substrate may be a fluorogenic substrate CDC-1, CDC-2, CDC-3, CDC-4, CDC-5, CNIR5, CNIR5.2, CNIR5-QSY22, CNIR7, CNIR7-TAT, CNIR9, CNIR10, CNIR800, CNIR800.2, CNIR800-3, XHX2-81, XHX2-91, XHX3-1, XHX3-2, XHX3-26, or XHX3-32 or a derivative or analog thereof comprises a colored dye or a chemical reagent effective to produce a color or pH change upon beta-lactamase activity thereon.

The present invention is directed further still to a method for screening for therapeutic compounds effective for treating a pathophysiological condition associated with a pathogenic bacteria in a subject. The method comprises selecting a potential therapeutic compound for the pathogenic bacteria, contacting the bacterial cells or a biological sample comprising the same with a fluorescent, luminescent or colorimetric detection agent and contacting the bacterial cells with the potential therapeutic compound. A fluorescent, luminescent or colorimetric signal produced by the bacterial cells or a biological sample comprising the same is measured in the presence and absence of the potential therapeutic compound such that a decrease in signal in the presence of the therapeutic compound compared to the signal in the absence thereof indicates a therapeutic effect of the compound against the pathogenic bacteria. For example the fluorescent, luminescent or colorimetric detection agent is CNIR2, CNIR3, CNIR4, CNIR5, CNIR5-QSY22, CNIR7, CNIR9, CNIR10, CNIR7-TAT, a caged luciferin, a colorimetric reagent or a derivative thereof.

The present invention is directed to a related method for screening for therapeutic compounds effective for treating a pathophysiological condition associated with a pathogenic bacteria in a subject. The method comprises the steps described immediately supra using a fluorogenic substrate, as the detection agent, that is CDC-1, CDC-2, CDC-3, CDC-4, CDC-5, CNIR5, CNIR5.2, CNIR5-QSY22, CNIR7, CNIR7-TAT, CNIR9, CNIR10, CNIR800, CNIR800.2, CNIR800-3, XHX2-81, XHX2-91, XHX3-1, XHX3-2, XHX3-26, or XHX3-32 or a derivative or analog thereof or comprises a colored dye or a chemical reagent effective to produce a color or pH change upon beta-lactamase activity thereon.

The present invention is directed further still to a method for imaging a pathogenic bacteria. The method comprises contacting a pathogenic bacteria with a fluorogenic substrate for a beta-lactamase enzyme thereof, delivering to the pathogenic bacteria an excitation wavelength for a product of beta-lactamase activity on the substrate and acquiring fluorescent, luminescent or colorimetric signals emitted from the product. A 3D reconstruction of the acquired signals is produced thereby imaging the pathogenic bacteria.

The present invention is directed further still to a substrate for a bacterial beta-lactamase that produces a detectible fluorescent, luminescent or colorimetric signal upon beta-lactamase activity thereon. Representative substrates include but are not limited to CDC-1, CDC-2, CDC-3, CDC-4, CDC-5, CNIR5, CNIR5.2, CNIR5-QSY22, CNIR7, CNIR7-TAT, CNIR9, CNIR10, CNIR800, CNIR800.2, CNIR800-3, XHX2-81, XHX2-91, XHX3-1, XHX3-2, XHX3-26, or XHX3-32 or a derivative or analog thereof or that comprise a colored dye or a chemical reagent effective to produce a color or pH change upon beta-lactamase activity thereon. The present invention is directed to another related substrate further comprising a particle, microsphere or a biotin linked thereto.

The present invention is directed further still to a method for detecting a pathogenic bacteria in real time in a subject. The method comprises introducing into the subject a substrate radiolabeled with an isotope associated with gamma emission where the substrate is for a beta-lactamase or other enzyme or protein specific to the pathogenic bacteria. The subject is imaged for gamma emissions from the radiolabeled substrate during activity thereon and signals generated by the emitted gamma rays are acquired. A 3D reconstruction of the concentration in the subject of the radiolabel based on intensity of the gamma ray generated signals is produced thereby detecting the pathogenic bacteria. The present invention is directed to a related method further comprising diagnosing in real time a pathophysiological condition associated with the pathogenic bacteria based on detection thereof. The present invention is directed to another related method further comprising administering one or more therapeutic compounds effective to treat the pathophysiological condition. The present invention is directed to yet another related method further comprising readministering the radiolabeled substrate to the subject and reimaging the subject to monitor the efficacy of the therapeutic compound; wherein a decrease in gamma emission compared to gamma emission at diagnosis indicates a therapeutic effect on the pathophysiological condition.

The present invention is directed further still to a radiolabeled substrate for a bacterial beta-lactamase suitable for PET or SPECT imaging as described herein.

The present invention is directed further still to an assay device for visibly detecting a pathogenic bacteria in a biological sample. The assay device comprises a platform having means for receiving an incubation mixture comprising the biological sample and a color-producing substrate for a beta-lactamase enzyme associated with the pathogenic bacteria and means for capturing and concentrating a colored product produced by the beta-lactamase activity upon the substrate in fluid connection to the receiving means. The present invention is directed to a related invention further comprising means for allowing only the colored product to flow downstream from the receiving means. The present invention is directed to a related invention further comprising an internal control downstream from the receiving means. The present invention is directed to another related invention where the substrate comprises a chemical reagent and the device further comprises a second reagent as means to produce color from the chemical reagent. The present invention is directed to another related invention where the substrate is linked to biotin and the device further comprises avidin as means to capture the biotin-linked substrate.

Other and further objects, features, and advantages will be apparent from the following description of the presently preferred embodiments of the invention, which are given for the purpose of disclosure.

BRIEF DESCRIPTIONS OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A-1C show BlaC mutant crystals prior to soaking with CNIR4 (FIG. 1A) and BlaC mutant crystals retaining CNIR4 substrate (FIG. 1B). FIG. 1C illustrates catalysis of cefotazime by Mtb BlaC and the product formed by hydrolysis of the lactam ring.

Figure 8A:
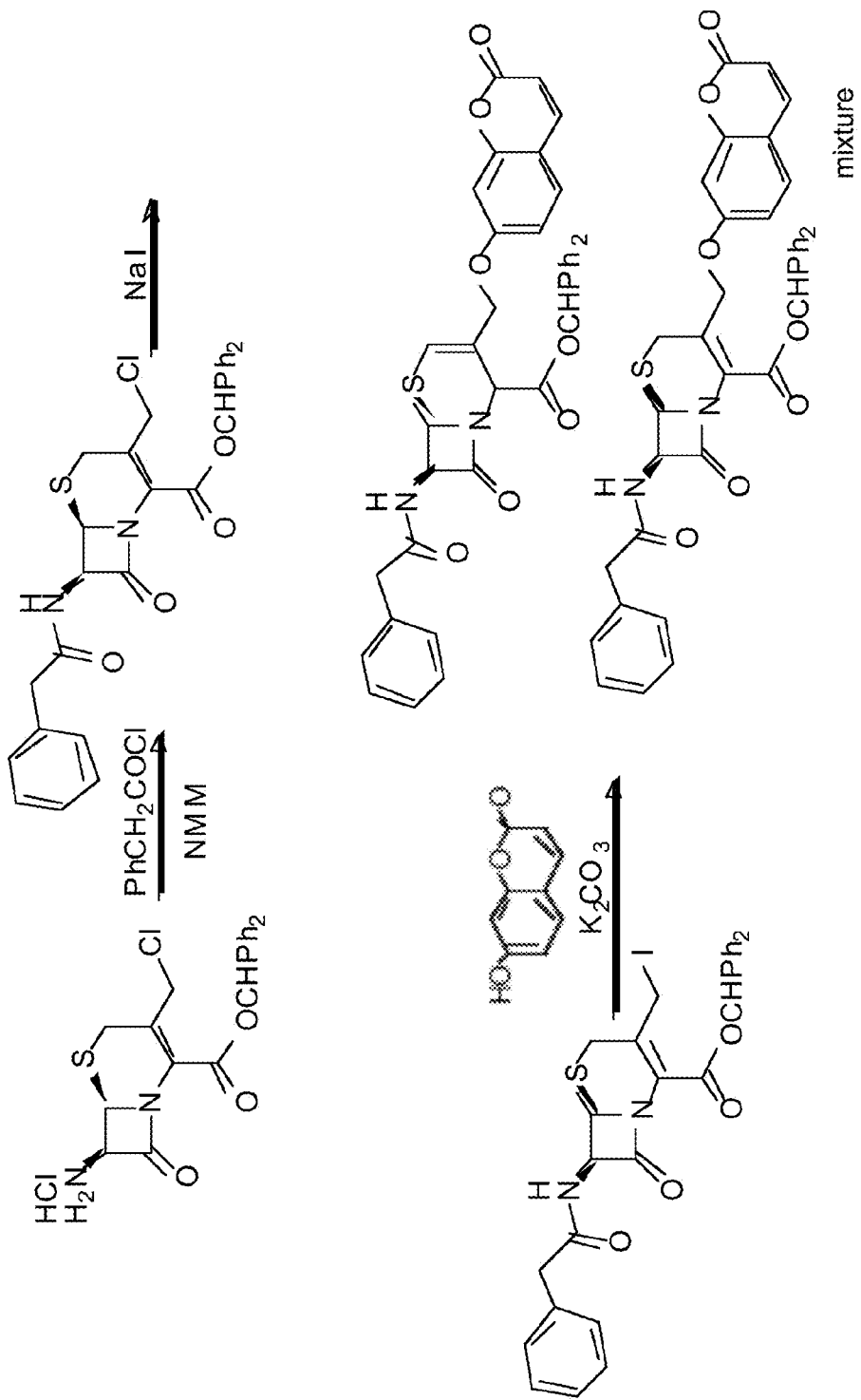
Figure 8B:
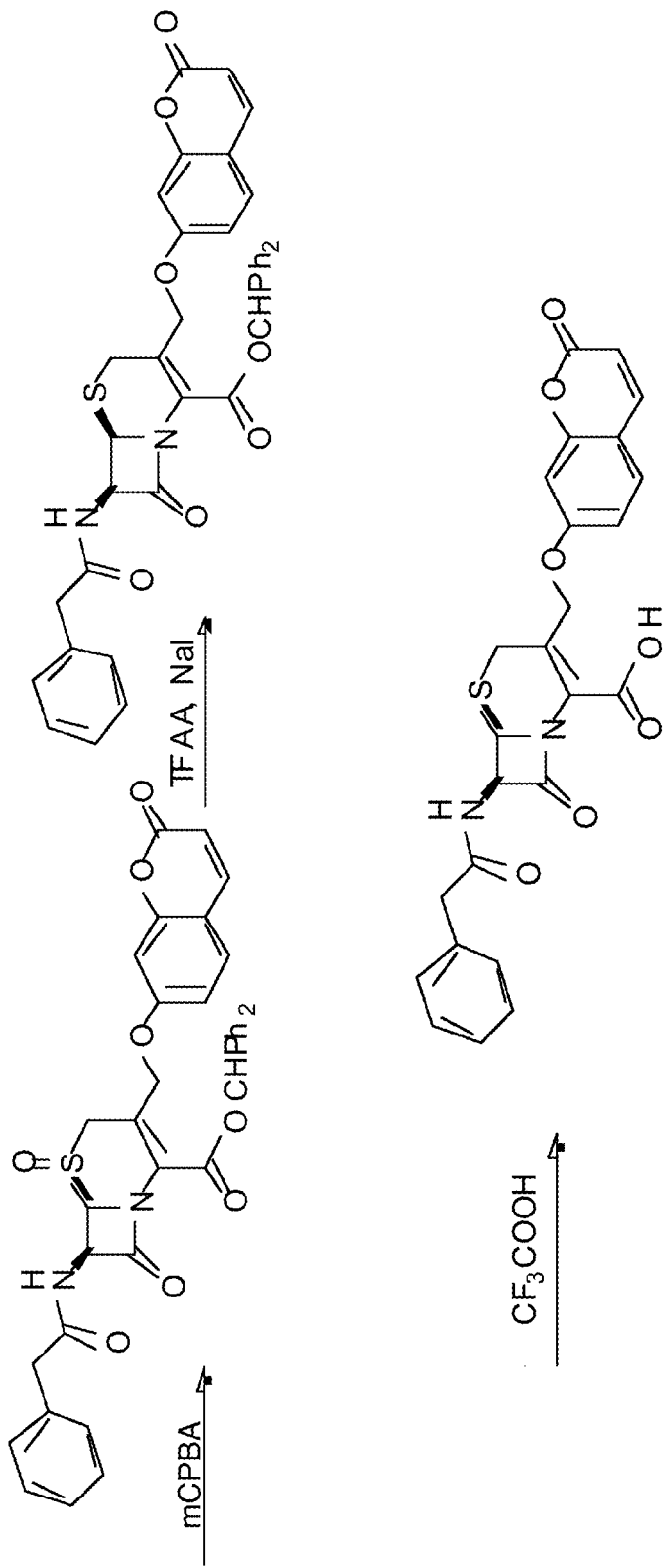
Figure 8C:
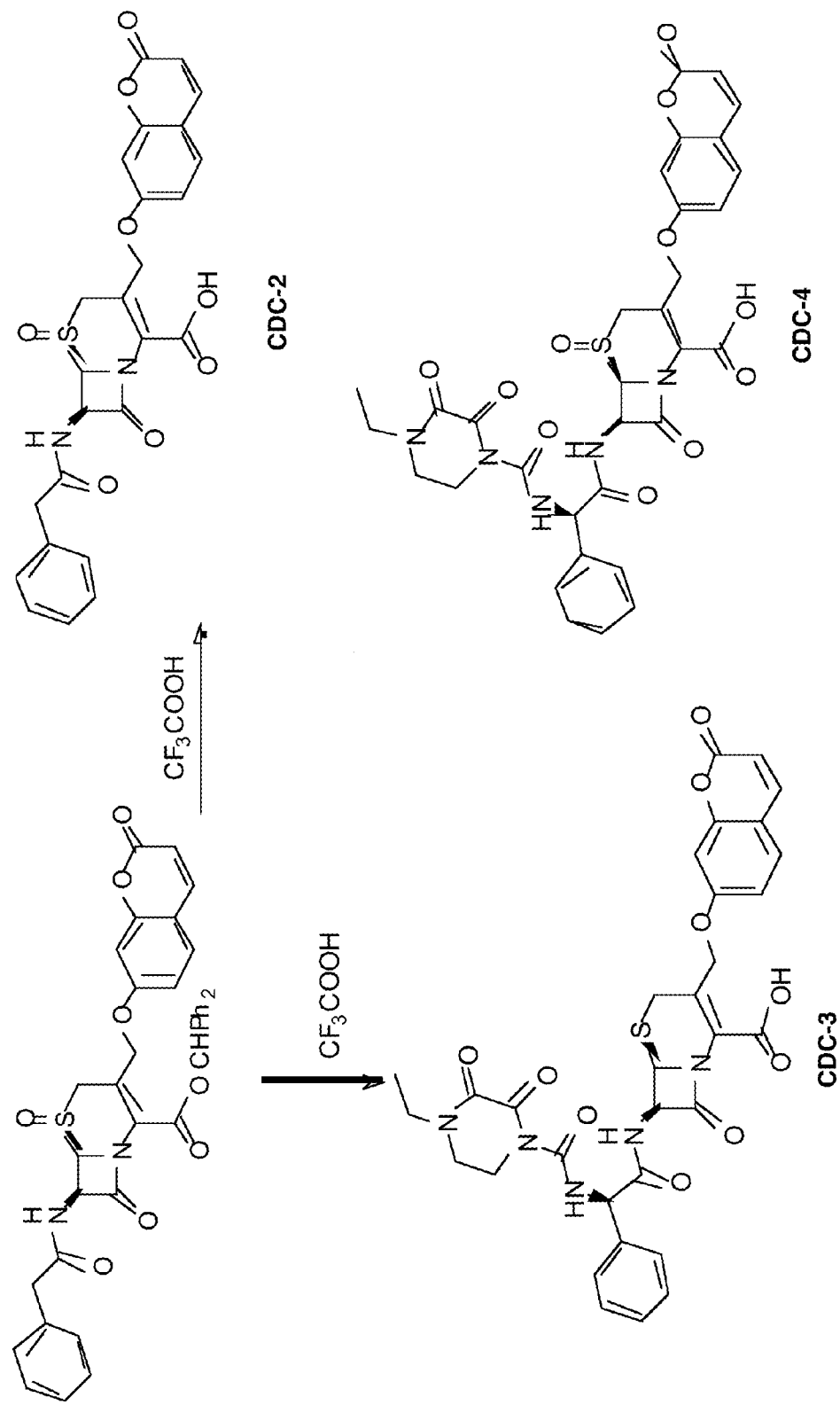

FIGS. 8A-8H depict the synthetic schema and hydrolysis kinetics of fluorogenic substrates CDC-1-5. FIGS. 8A-8C show the synthesis of CDC-1-4. FIGS. 8D-8E show the emission of probes CDC-1, 2, 3, 4 at 455 nm after treatment of TEM-1 Bla or Mtb BlaC, respectively, vs time. (Concentration of substrate: 5 mM; concentration of TEM-1 Bla is 2 nM in PBS (pH=7.4); concentration of Mtb BlaC is 10 nM in PBS (pH=7.4); excitation at 400 nm). FIG. 8F shows the synthesis of CDC-5. FIG. 8G show the mission of substrate CDC-1 at 455 nm after treatment of beta-lactamase vs. time (Solid line: treated with Mtb BlaC; dash line: treated with TEM-1 Bla; concentration of probe: 5 mM; concentration of TEM-1 Bla: 20 nM in PBS (pH=7.4); excitation at 400 nm). FIG. 8H shows the emission of probes CDC-5 at 455 nm after treatment of beta-lactamase vs. time (Solid line: treated with Mtb BlaC; dash line: treated with TEM-1 Bla; Concentration of probe: 5 mM; concentration of Mtb BlaC: 20 nM in PBS (pH=7.4); excitation at 400 nm).

Figure 9A:
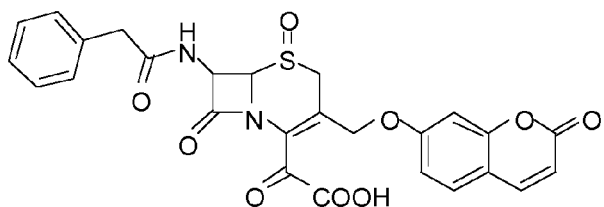
Figure 9B:
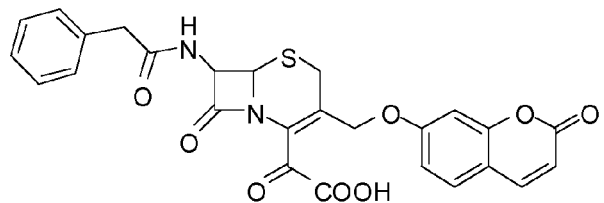
Figure 9D:
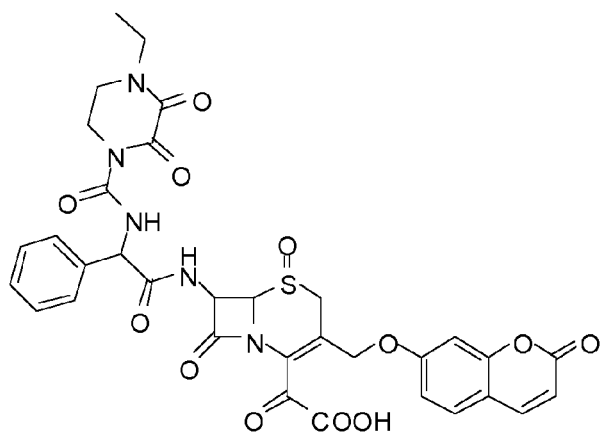
Figure 9E:
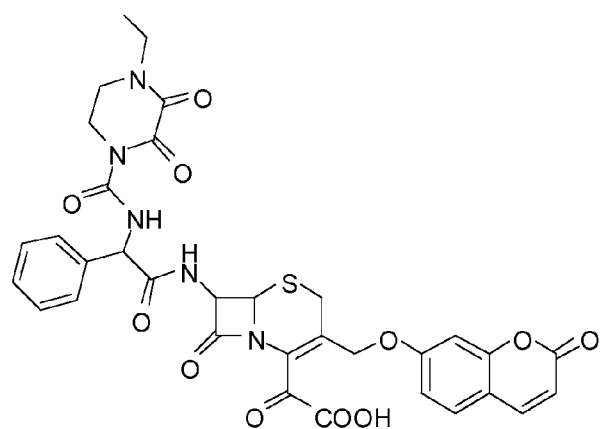
Figure 9C:
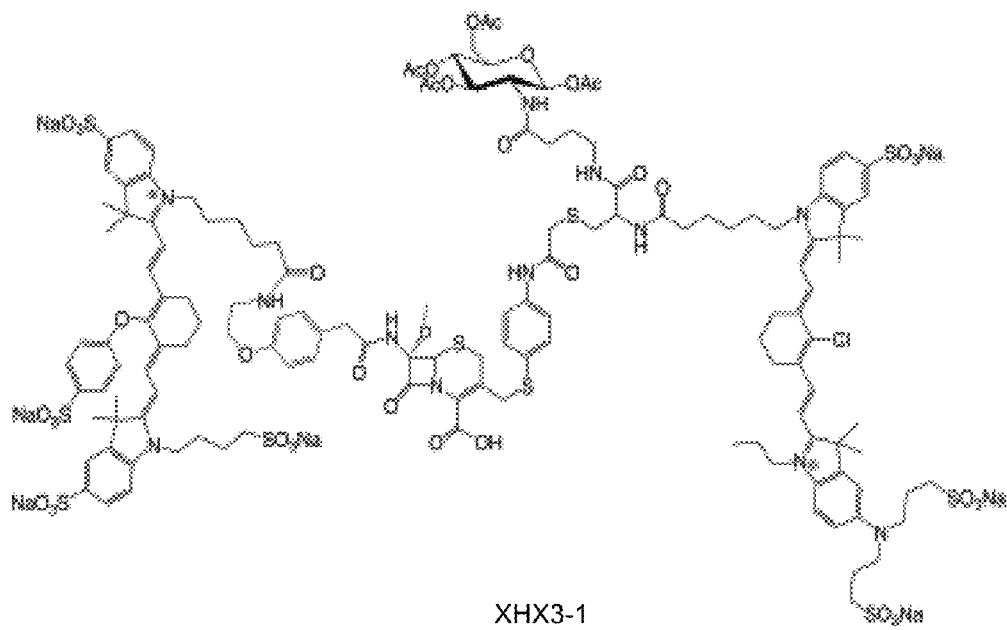
Figure 9F:
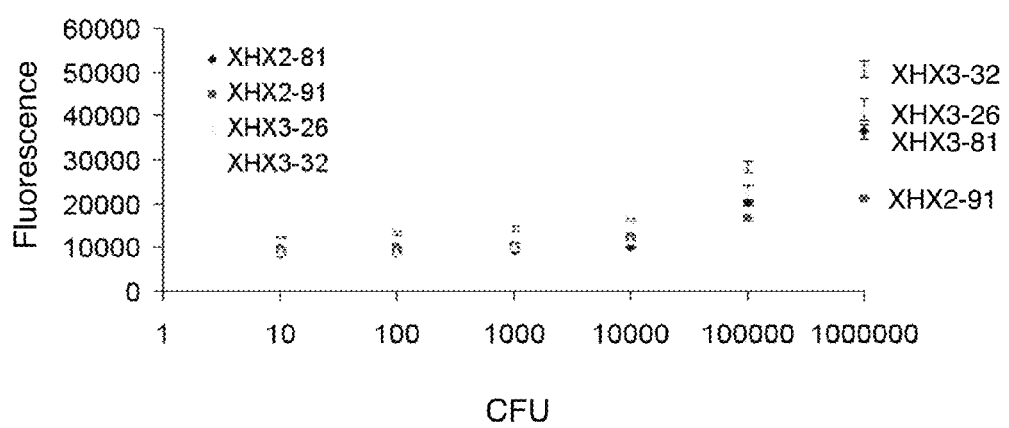

FIGS. 9A-9F depict the chemical structures of XHX2-81, XHX2-91, XHX3-1 XHX3-26, and XHX3-32 (FIGS. 9A-9E) and demonstrates correlation between bacterial numbers and fluorescent signal using XHX2-81, XHX2-91, XHX3-26, and XHX3-32 (FIG. 9F). Excitation: 360 nm (1×PBS); Emission Max: 453 nm (1×PBS); XHX-2-81 (10 mM in DMSO, 60 mL); XHX-2-91 (100 mM in DMSO, 10 mL); XHX-3-26 (20 mM in DMSO, 42 mL); XHX-3-32 (10 mM in DMSO, 100 mL).

Figure 10A:
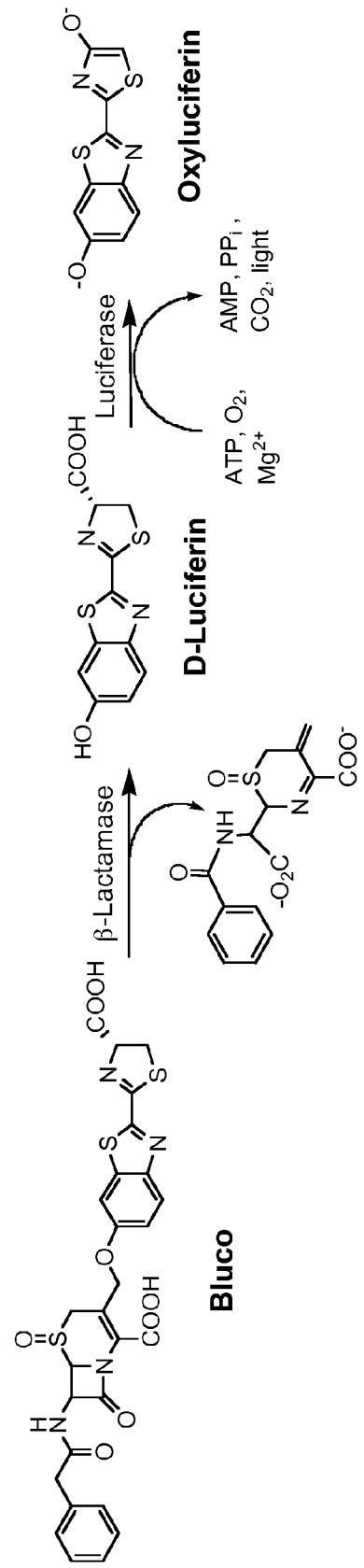
Figure 10B:
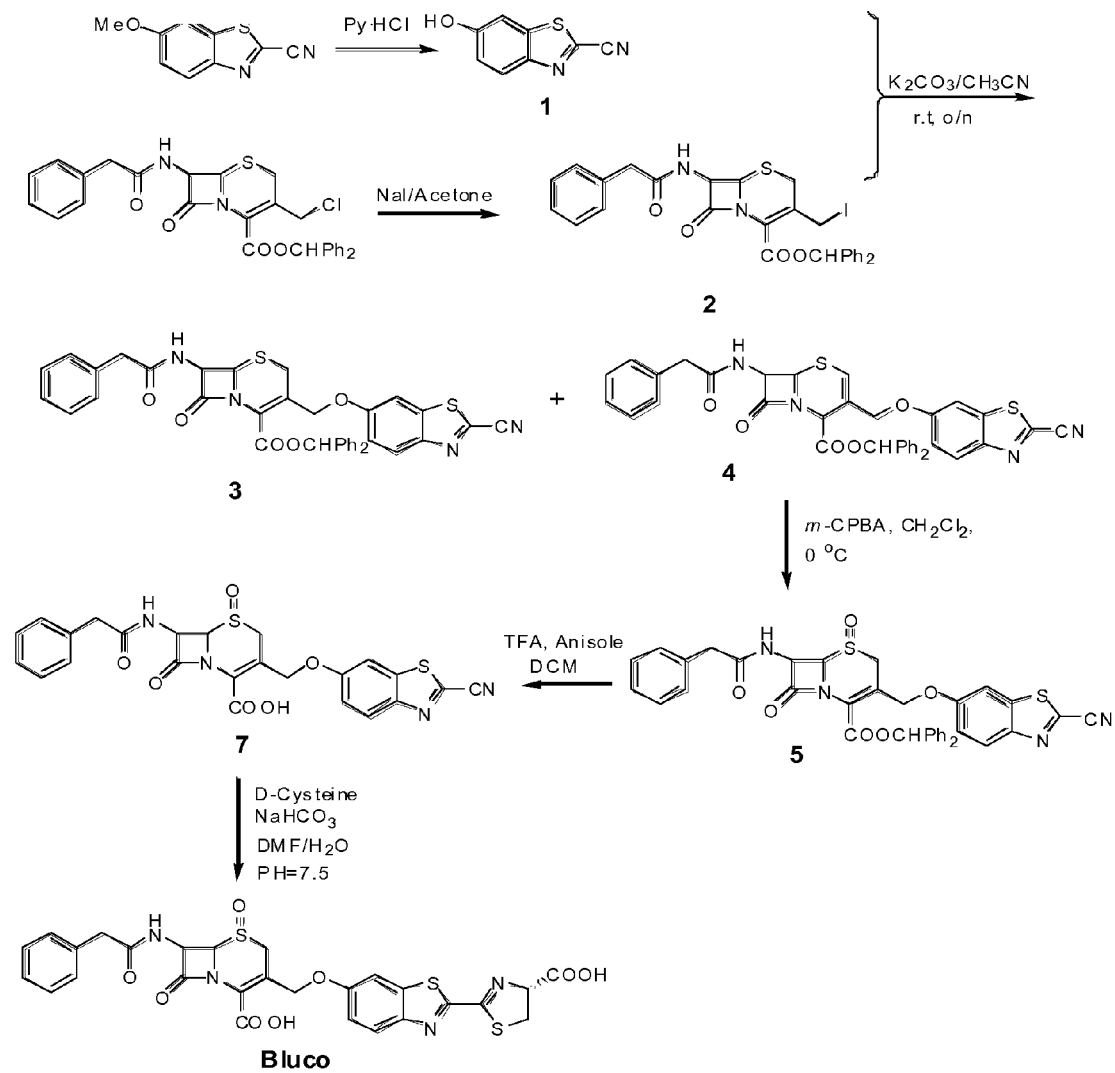

FIGS. 10A-10B depict the chemical synthesis of Bluco (FIG. 10A) and the use of Bluco for sequential reporter bioluminescent assay (SREL) imaging of beta-lactamase (FIG. 10B).

Figure 11A:
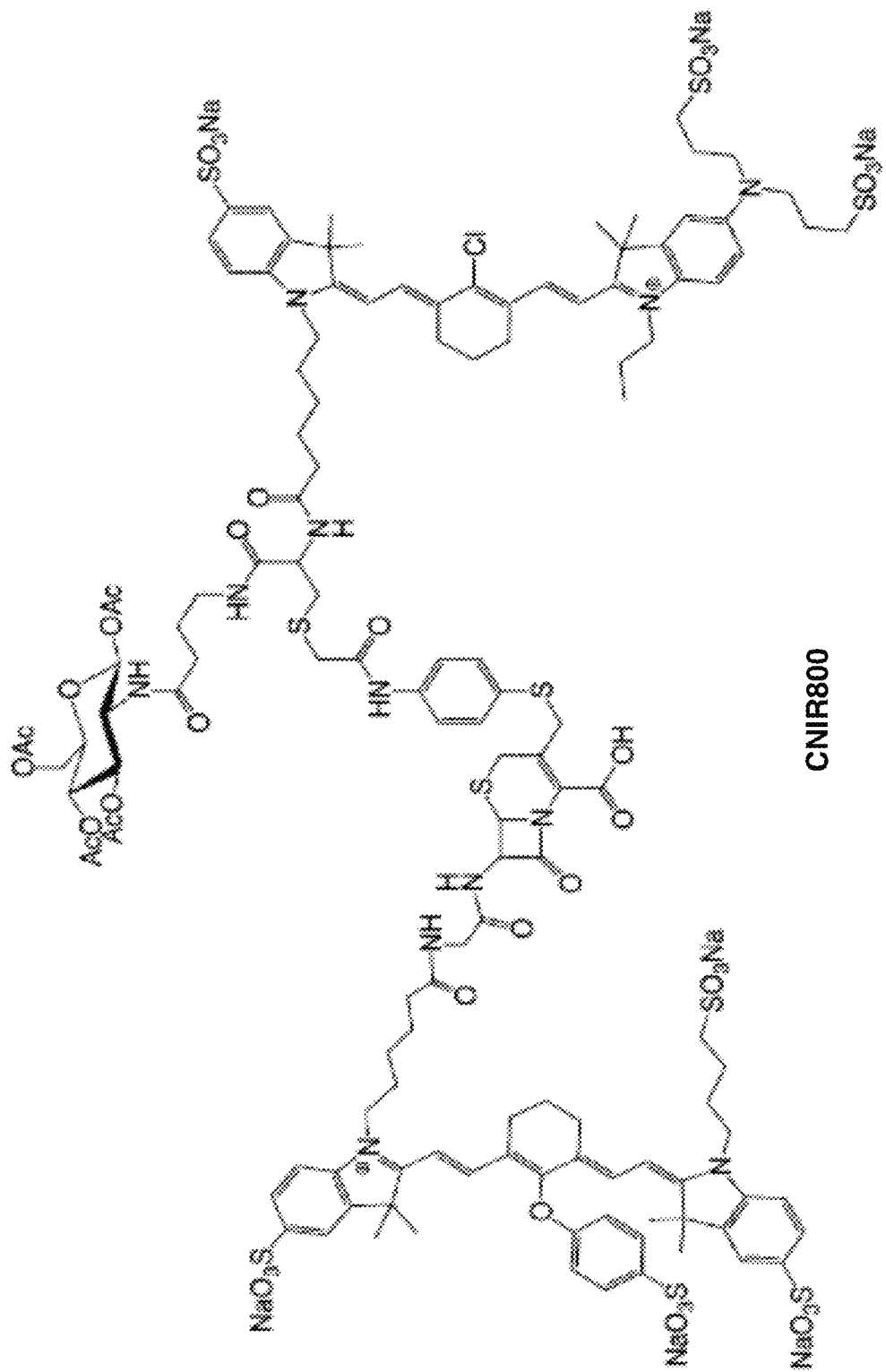
Figure 11D:
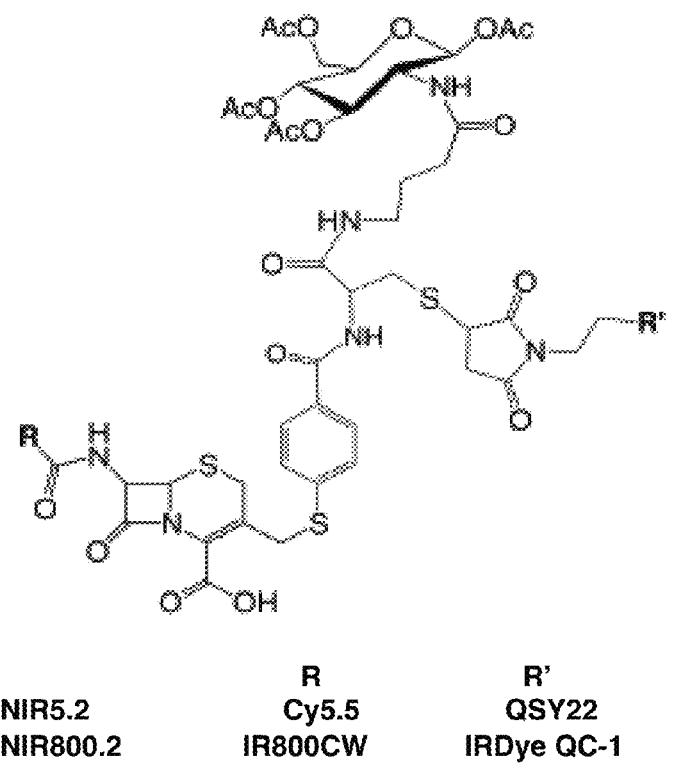
Figure 11E:
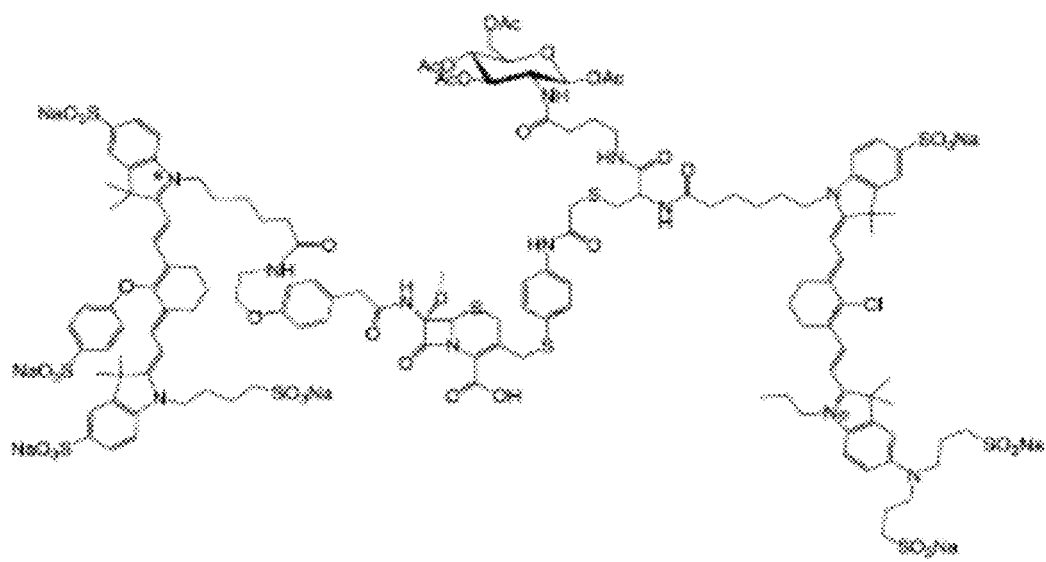

FIGS. 11A-11E depict CNIR800 (FIG. 11A), alternate chemical synthetic routes to preparing CNIR and CNIR-like probes and their derivatives and analogs (FIGS. 11B-11C) and structures of probes so synthesized, such as CNIR5.2 and CNIR800.2 (FIG. 11D) and CNIR800-3 (FIG. 11E).

FIGS. 12A-12B illustrate detection of Bla activity in *E. coli* (FIG. 12A) and *M. tuberculosis* (FIG. 12B) with CNIR5. Control contains LB media and CNIR5 without transformed *E. coli*.

FIGS. 13A-13H depict the fluorescence emission spectra (FIGS. 13A-13D) and kinetics of fluorescence label incorporation (FIGS. 13E-13H). Emission spectra for CNIR4 (FIG. 13A), CNIR5 (FIG. 13B), CNIR9 (FIG. 13C), and CNIR10 (FIG. 13D) are shown before (CNIR) and after (CNIR+Bla) cleavage with TEM-1 Bla for 10 min. The kinetics of CNIR4 (FIG. 13E), CNIR5 (FIG. 13F), CNIR9 (FIG. 13G), and CNIR10 (FIG. 13H) fluorescent label incorporation directly into wild type Mtb and the Mtb BlaC mutant (blaCm) is shown.

Figure 14A:
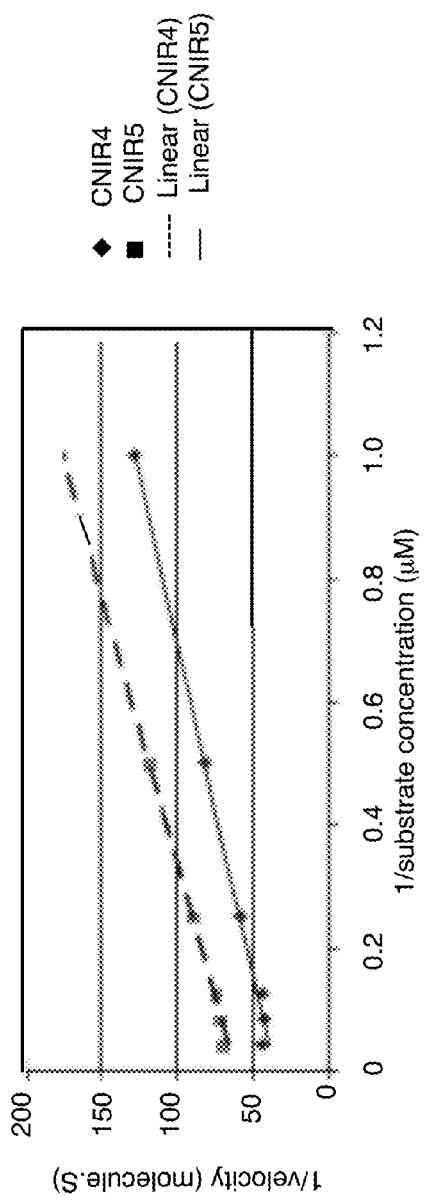
Figure 14B:
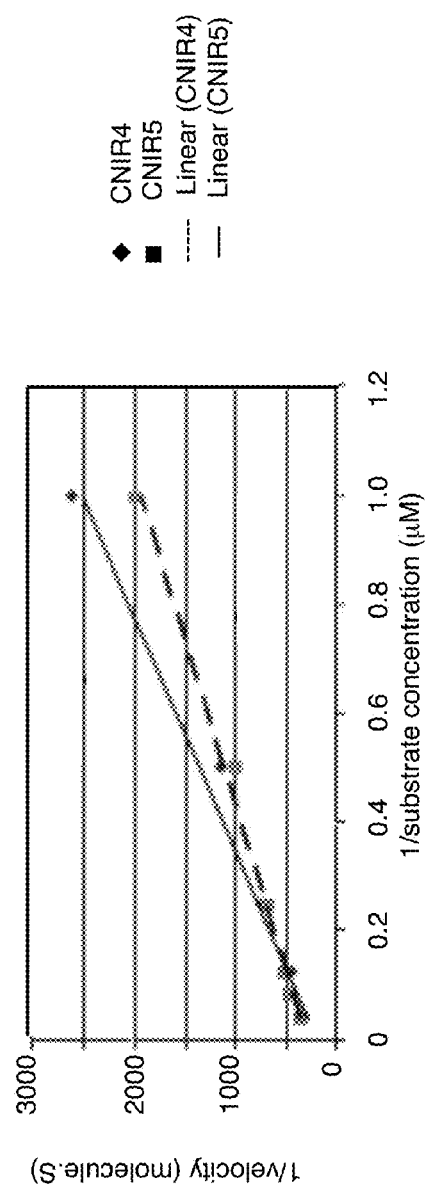

FIGS. 14A-14B depict kinetics of *E. coli* TEM-1 beta-lactamase and *Mycobacterium tuberculosis* Bla-C beta-lactamase with CNIR4 (FIG. 14A) and CNIR5 (FIG. 14B) substrates.

FIGS. 15A-15H depict the kinetics of fluorescent incorporation and distribution ratios therein (FIGS. 15A-15H) of

*Mycobacterium tuberculosis* bacteria alone in media with CNIR4 (FIGS. 15A, 15E), CNIR5 (FIGS. 15B, 15F), CNIR9 (FIGS. 15C, 15G), and CNIR10 (FIGS. 15D, 15H).

FIGS. 16A-16H depict the kinetics of fluorescent incorporation (FIGS. 16A-16D) and distribution ratios therein (FIGS. 16E-16H) of *Mycobacterium tuberculosis* bacteria infected macrophages with CNIR4 (FIGS. 16A, 16E), CNIR5 (FIGS. 16B, 16F), CNIR9 (FIGS. 16C, 16G), and CNIR10 (FIGS. 16D, 16H).

Figure 17:
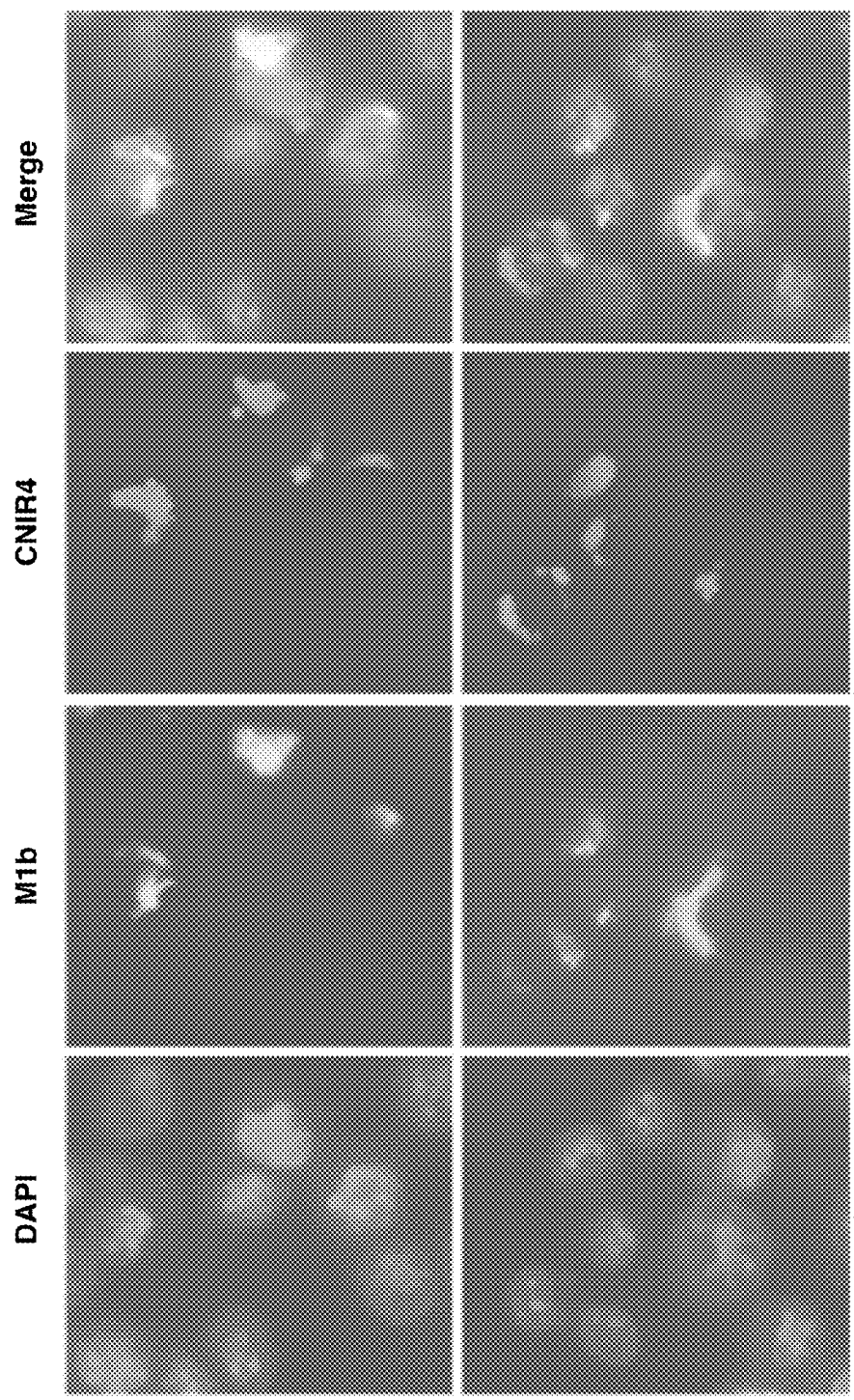

FIG. 17 depicts fluorescent confocal microscopy images showing intracellular incorporation of CNIR4 into *Mycobacterium tuberculosis* infected macrophages. DAPI stain (blue) indicates the nuclei of the infected cells, the green fluorescence is from GFP labeled *M. tuberculosis* and the red fluorescence is from cleaved CNIR4.

FIGS. 18A-18E depict the fluorescence from mice infected with *Mycobacterium tuberculosis* by intradermal inoculation of CNIR4 (FIG. 18A), CNIR5 (FIG. 18B), CNIR9 (FIG. 18C), and CNIR10 (FIG. 18D) at various concentrations from $10^8$ (lower left on each mouse), $10^7$ (upper left), $10^6$ (upper right). FIG. 18E compares signal versus background for each compound at each concentration of bacteria used for infection.

Figure 19E:
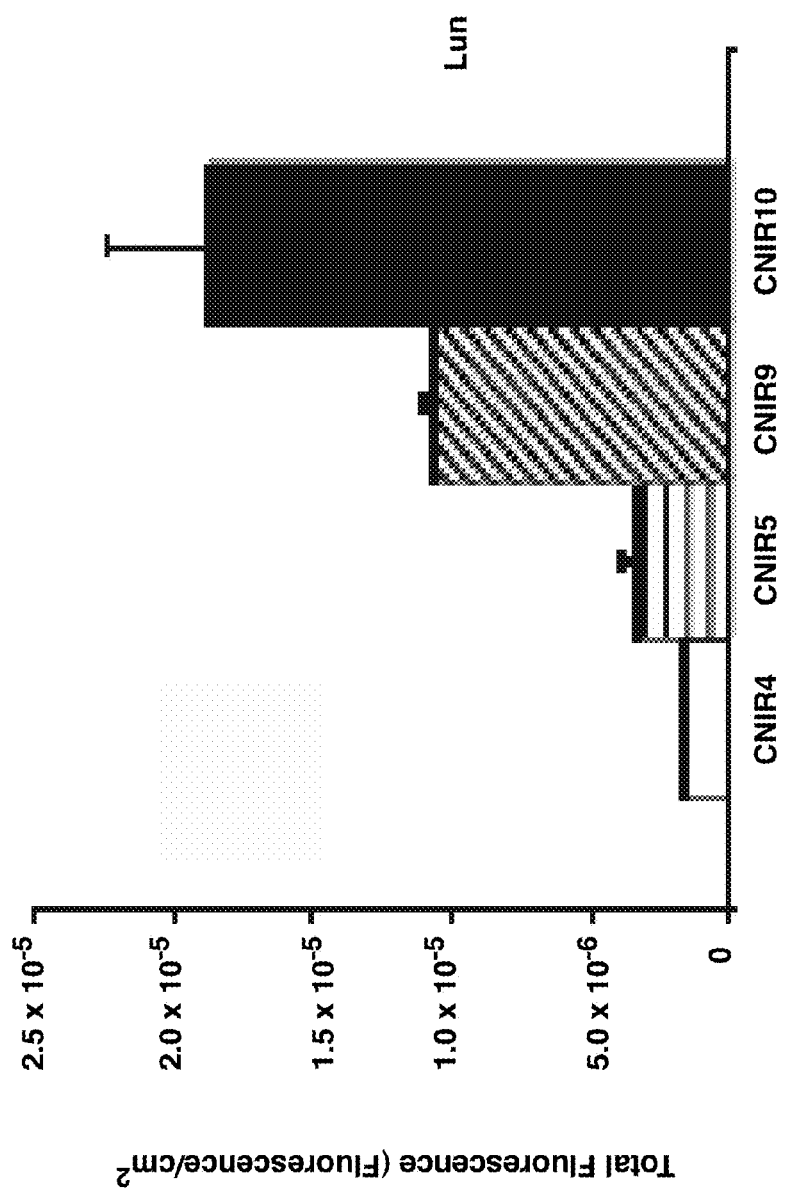

FIGS. 19A-19E are fluorescence images from mice that have been infected with *Mycobacterium tuberculosis* in the lungs by aerosol inoculation and fluorescence signal measured for CNIR4 (FIG. 19A), CNIR5 (FIG. 19B), CNIR9 (FIG. 19C), and CNIR10 (FIG. 19D). In each of FIGS. 19A-19D, the left mouse in each panel is uninfected, the second from left is infected with *M. tuberculosis* that has a mutation in the blaC gene and the two right side mice in each panel are infected with wild type *M. tuberculosis*. The three right mice in each panel were given CNIR4, CNIR5, CNIR9 or CNIR10 i.v. 24 h prior to imaging. FIG. 19E is a graph of signal vs. background for each compound in the pulmonary region in the dorsal image.

Figure 20F:
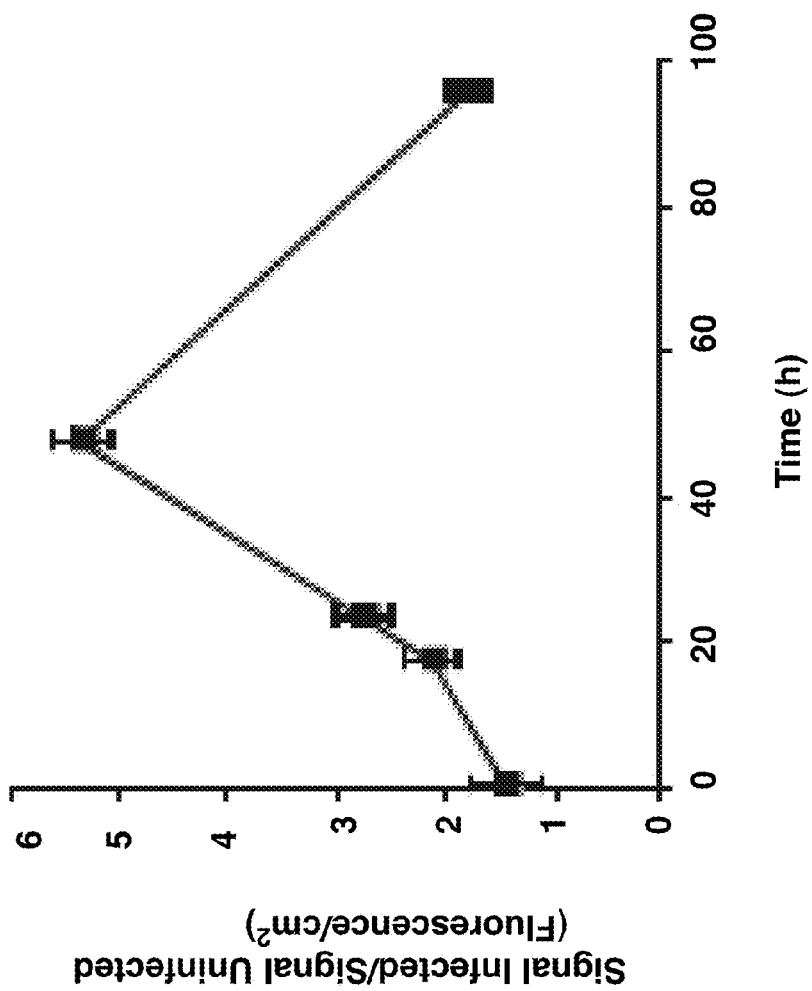

FIGS. 20A-20F are fluorescence images from mice infected by aerosol with *M. tuberculosis* and imaged using the substrate CNIR5 at 1 h (FIG. 20A), 18 h (FIG. 20B), 24 h (FIG. 20C), 48 h (FIG. 20D), and 60 h (FIG. 20E). In each panel of a dorsal, ventral or right and left side views, the mouse on the left is uninfected and the mouse on the right is infected. All mice were injected i.v. with CNIR5 prior to imaging at the time points noted. FIG. 20F is a graph quantifying the fluorescent signal obtained from the region of interest circled in the top panel of FIG. 19A.

Figures 21A, 21B:
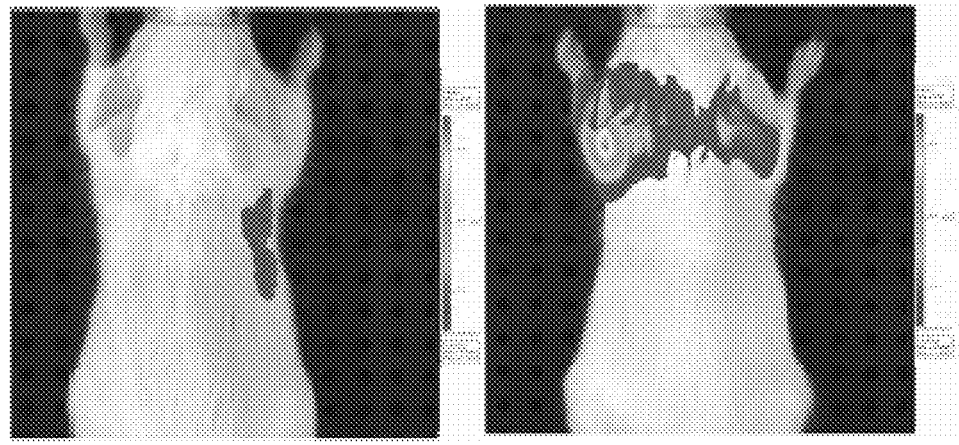

FIGS. 21A-21B depicts fluorescence imaging of mice infected with *M. tuberculosis* by aerosol (FIG. 21A) or uninfected (FIG. 21B) and imaged using transillumination, rather than reflectance, to reduce background signal.

Figure 22A:
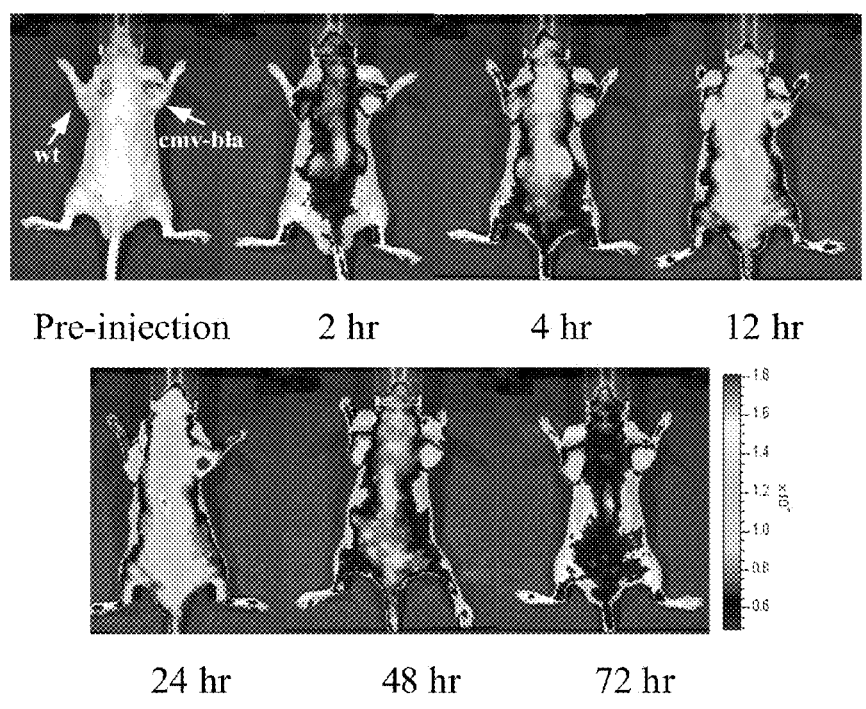
Figure 22C:
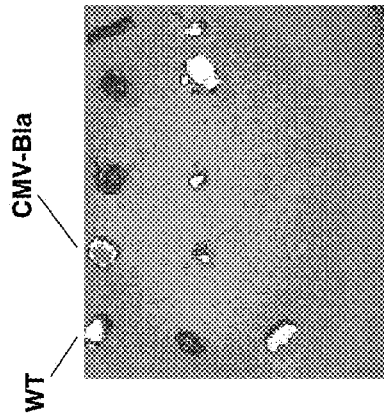
Figure 22B:
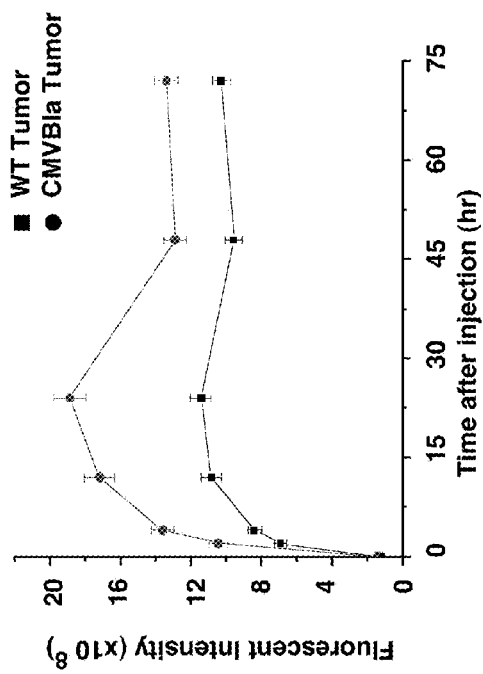
Figure 22D:
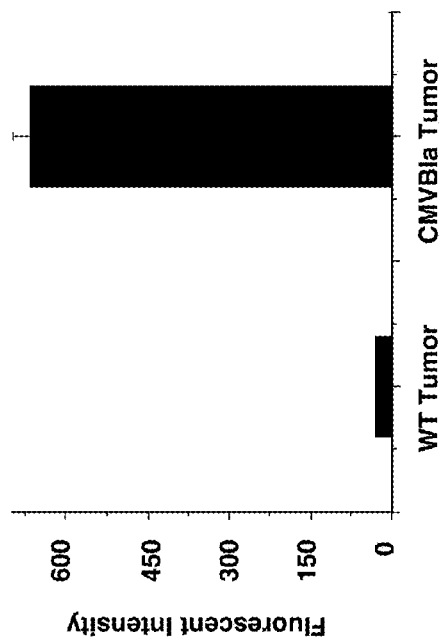

FIGS. 22A-22D illustrate imaging Bla expression with CNIR5 (7 nmol) in a nude mouse with a xenografted wild type C6 tumor at the left shoulder and a cmv-bla stably transfected C6 tumor at the right shoulder. FIG. 22A shows the overlaid fluorescence and bright field images at indicated time points. FIG. 22B shows a plot of the average intensity of each tumor vs. time. FIG. 22C shows images of excised tumors and organs. FIG. 22D shows results of a CC1 assay of Bla in extracts from both tumors.

Figure 23A:
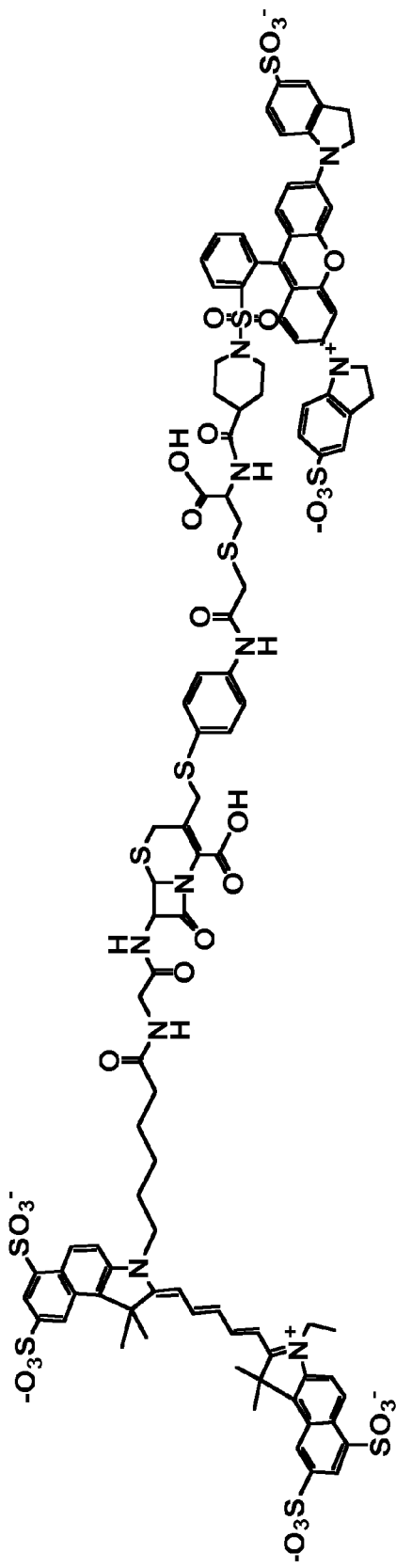

FIGS. 23A-23C illustrate imaging of Bla expression with CNIR6 (7 nmol) in a nude mouse with a xenografted wild type C6 tumor at the left shoulder and a cmv-bla stably transfected C6 tumor at the right shoulder. FIG. 23A is the chemical structure of CNIR6. FIG. 23B shows the overlaid fluorescence and bright field images at indicated time points. FIG. 23C shows plot of the average intensity of each tumor vs. time.

Figure 24A:
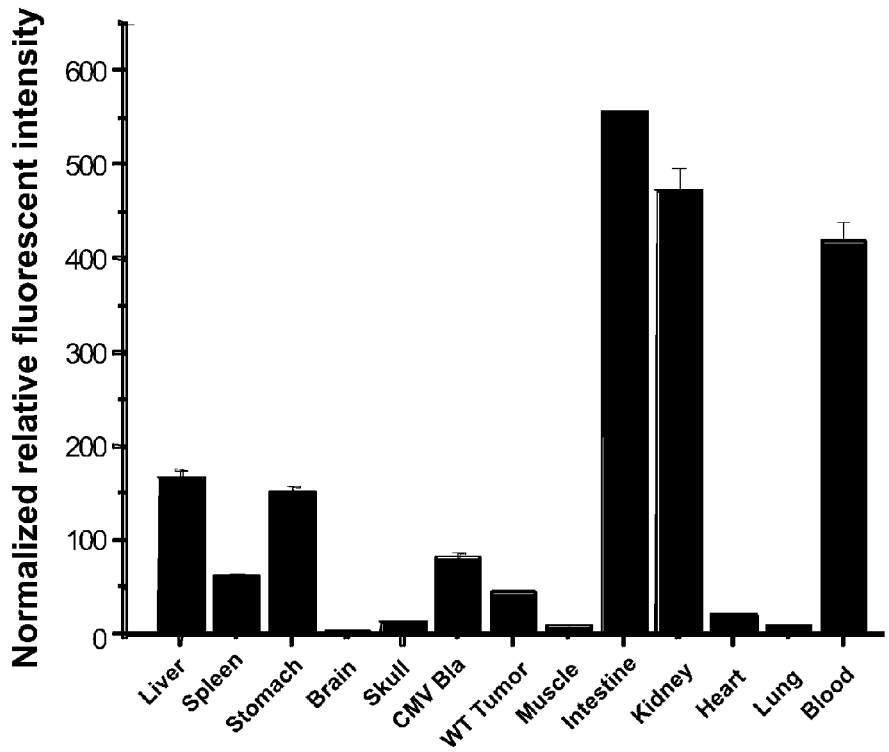
Figure 24B:
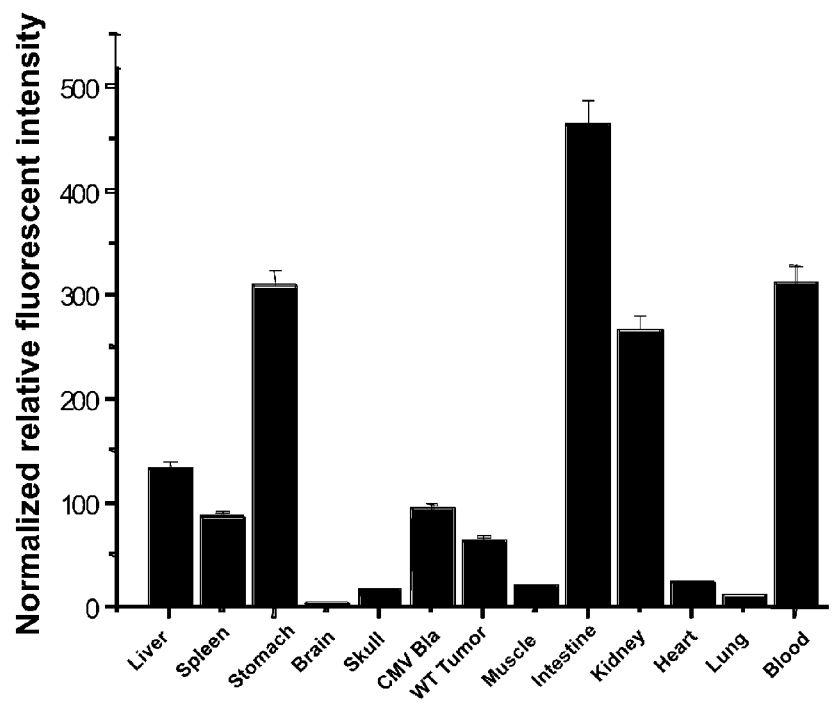

FIGS. 24A-24B illustrate the biodistribution of 7.5 nmoles of CNIR5 in various tissues after 4 hr (FIG. 24A) and 24 hr (FIG. 24B).

Figures 25A, 25B:
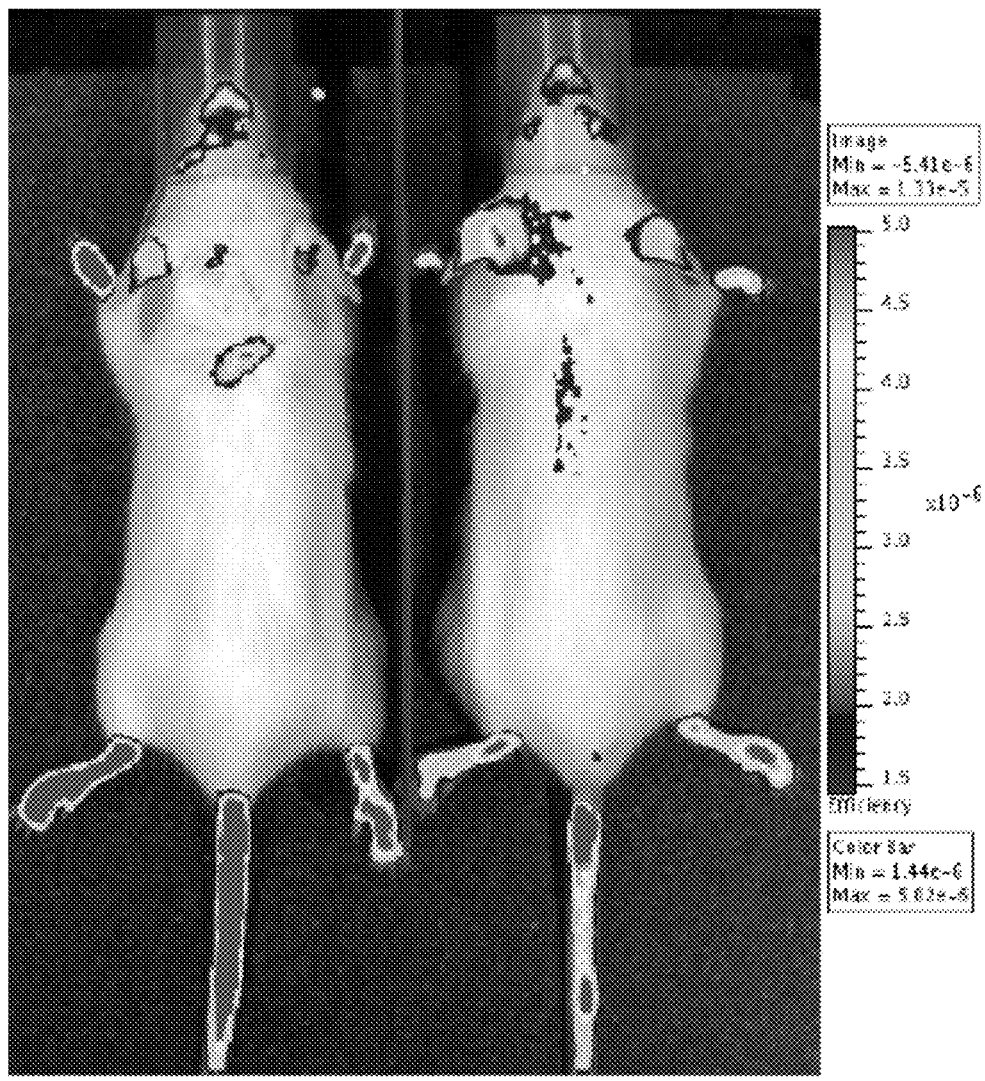

FIGS. 25A-25B are in vivo images of a mouse infected with *M. tuberculosis* (FIG. 25A) and a non-infected control mouse (FIG. 25B) using intravenous CNIR5 as imaging agent.

Figure 26A:
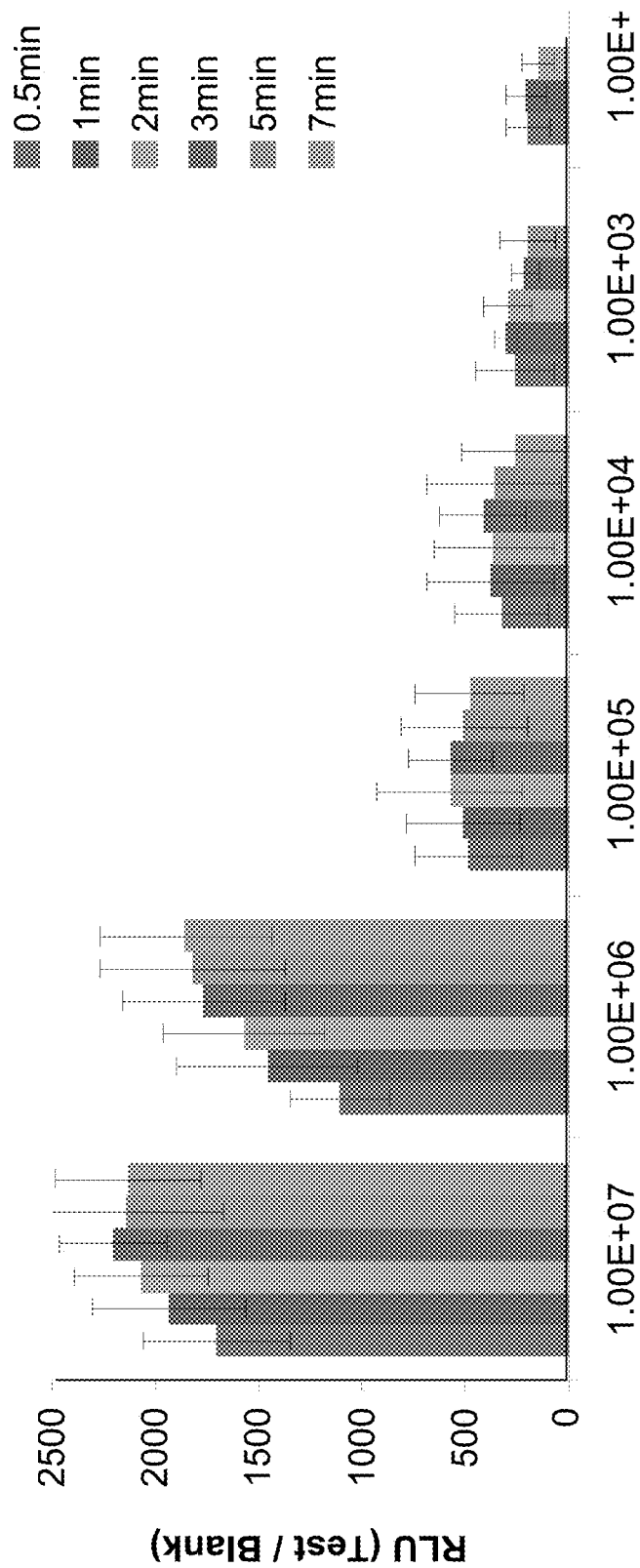
Figures 26B, 26C:
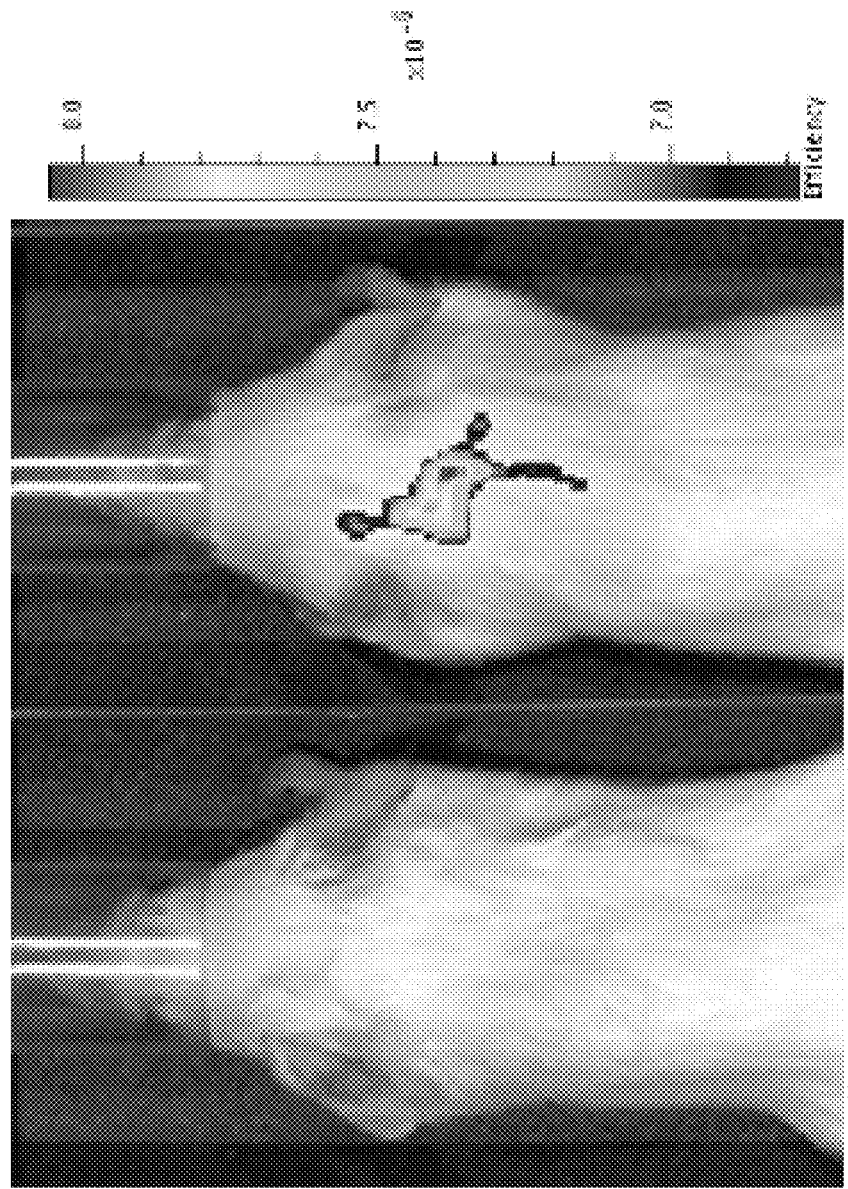

FIGS. 26A-26C illustrate the threshold of detection for SREL using a CNIR probe. FIG. 26A is a bar graph showing that less than 100 bacteria can be detected using a beta-lactamase CNIR probe with SREL imaging. FIGS. 26B-26C are in vivo images of live mice uninfected (FIG. 26B) or infected with *M. tuberculosis* (FIG. 26C).

Figure 27A:
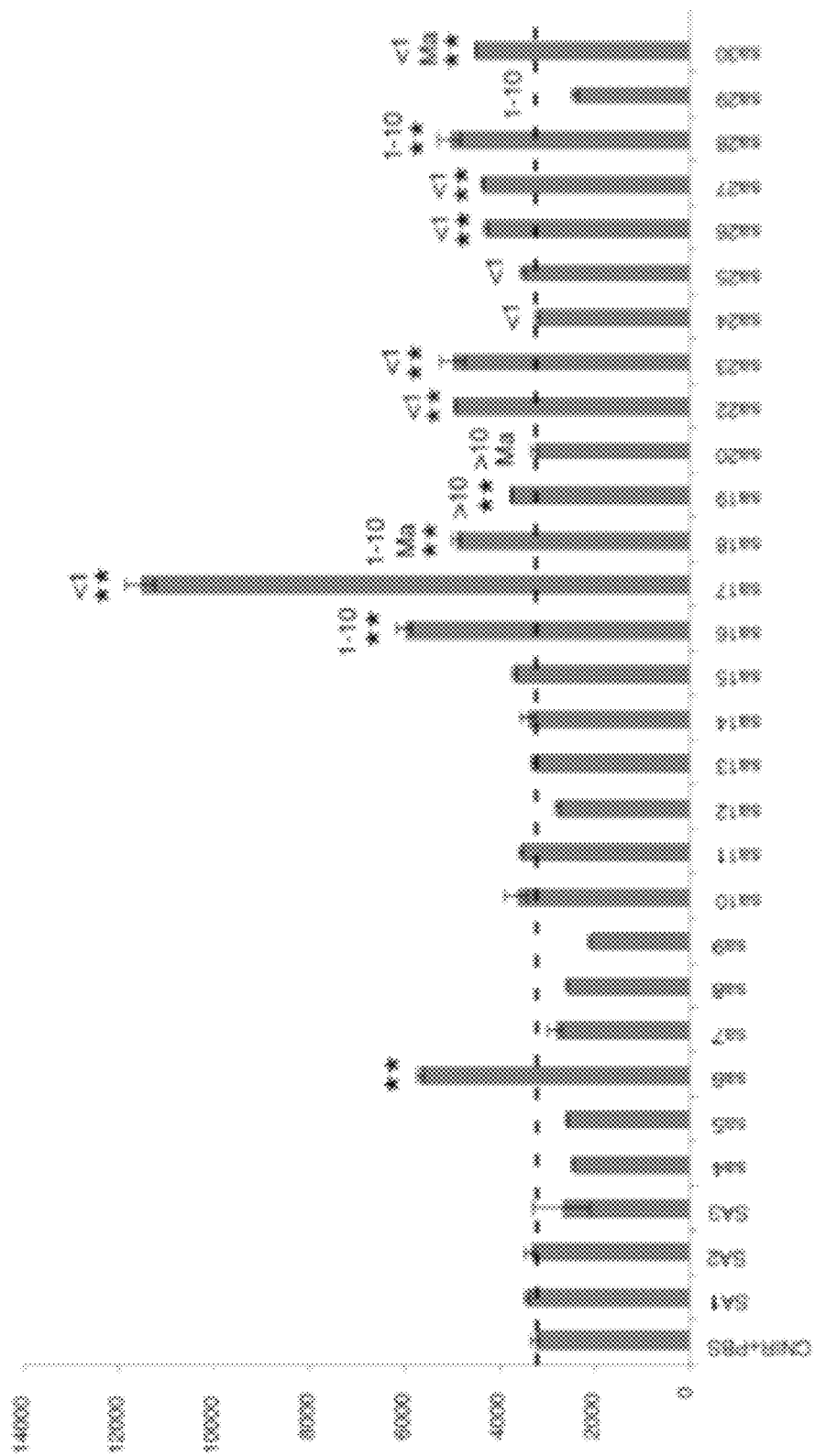
Figure 27D:
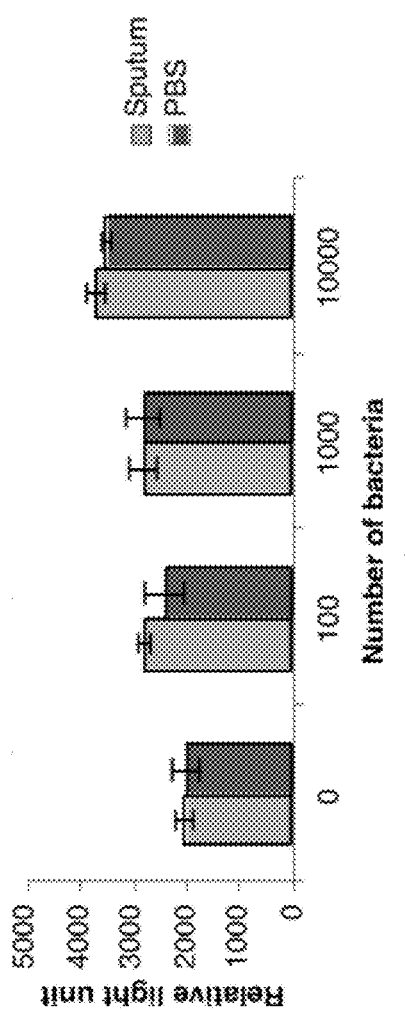
Figure 27E:
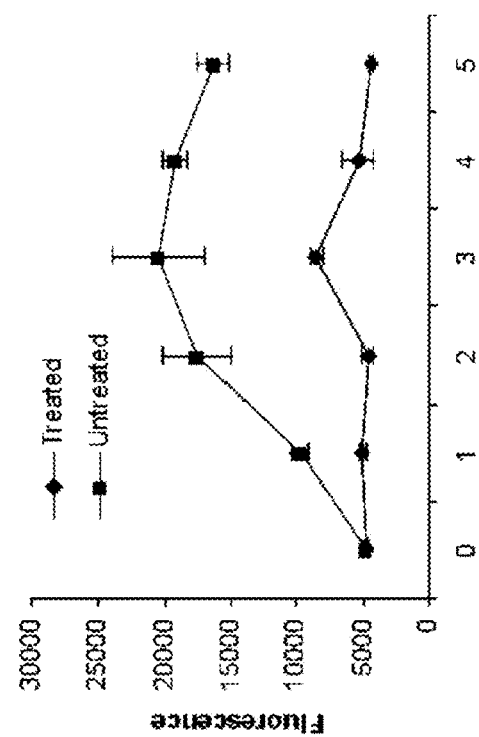

FIGS. 27A-27E depict the results from evaluating ability of CNIR5 to detect tuberculosis in clinical samples (FIG. 27A), the results from determining the tuberculosis detection threshold in sputum samples (FIG. 27B), the correlation between signal intensity and bacterial numbers in spiked sputum samples (FIG. 27C), the comparison between signal intensity and bacterial numbers in spiked sputum samples and PBS (FIG. 27D), and the evaluation of isoniazid+rifampin treatment in mycobacteria, including time to obtain measurable signal (FIG. 27E).

FIG. 28 depicts structures of IRDye800 series fluorophores.

Figure 29:
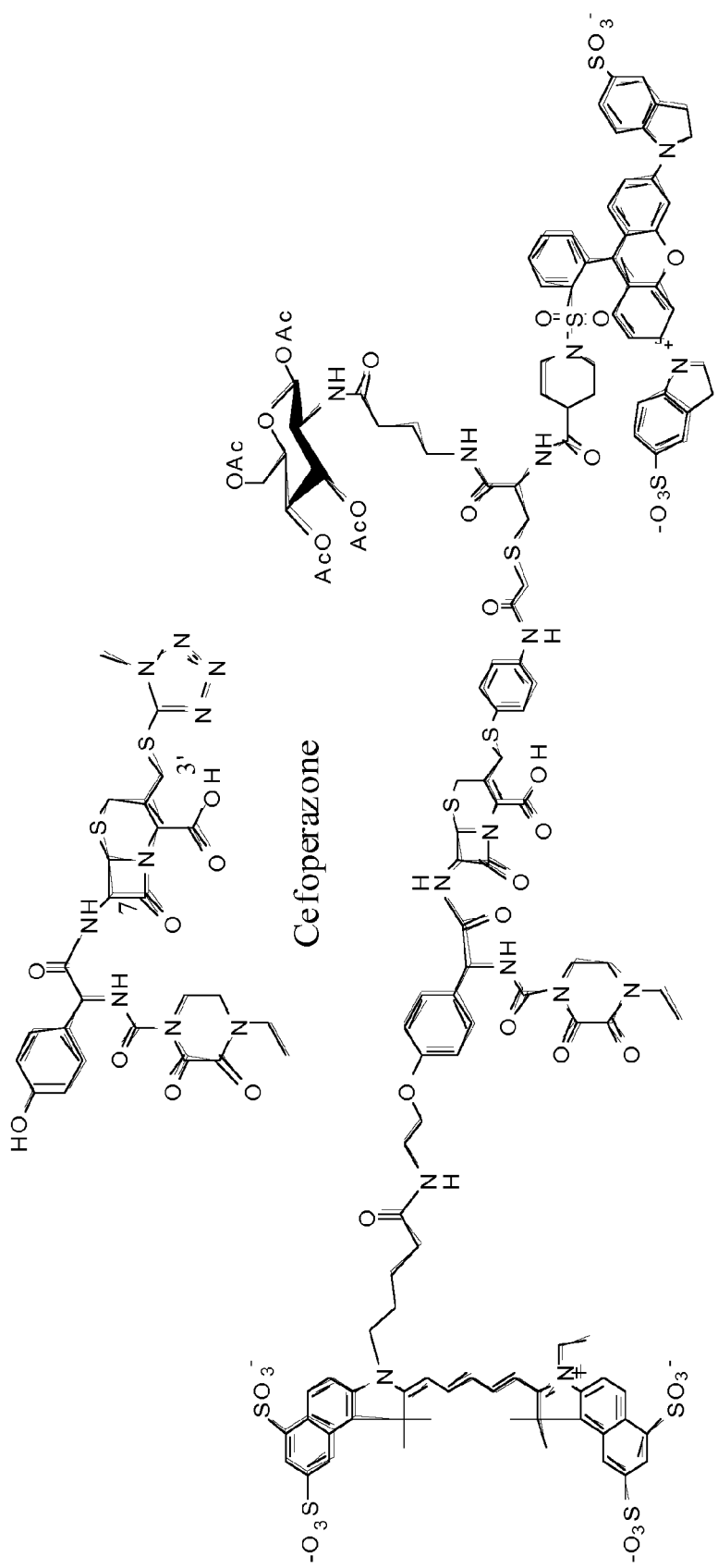

FIG. 29 depicts structures of cefoperazone and proposed CNIR probe.

Figure 30:
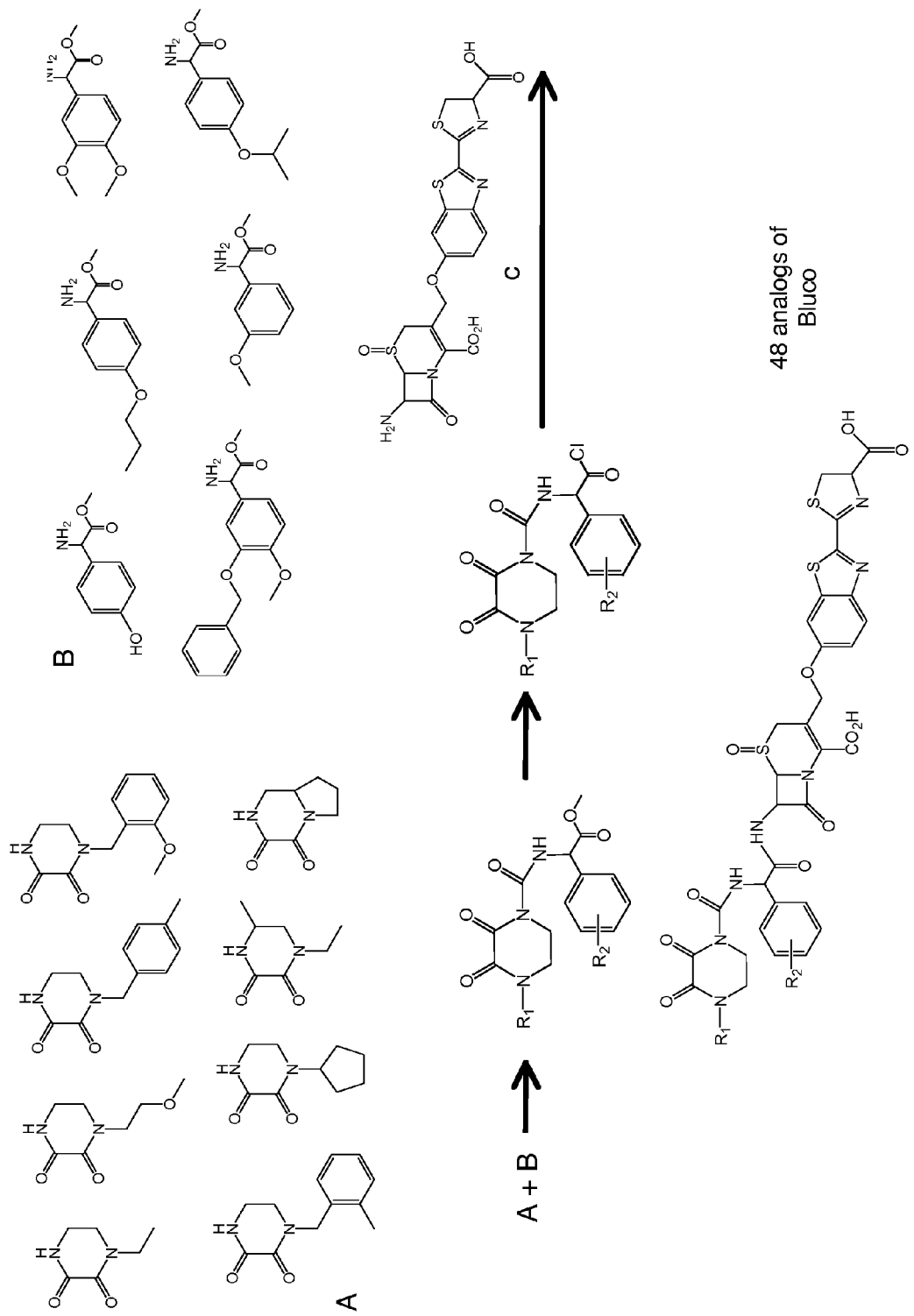

FIG. 30 depicts a scheme to build a small biased library of Bluco substrates.

Figure 31:
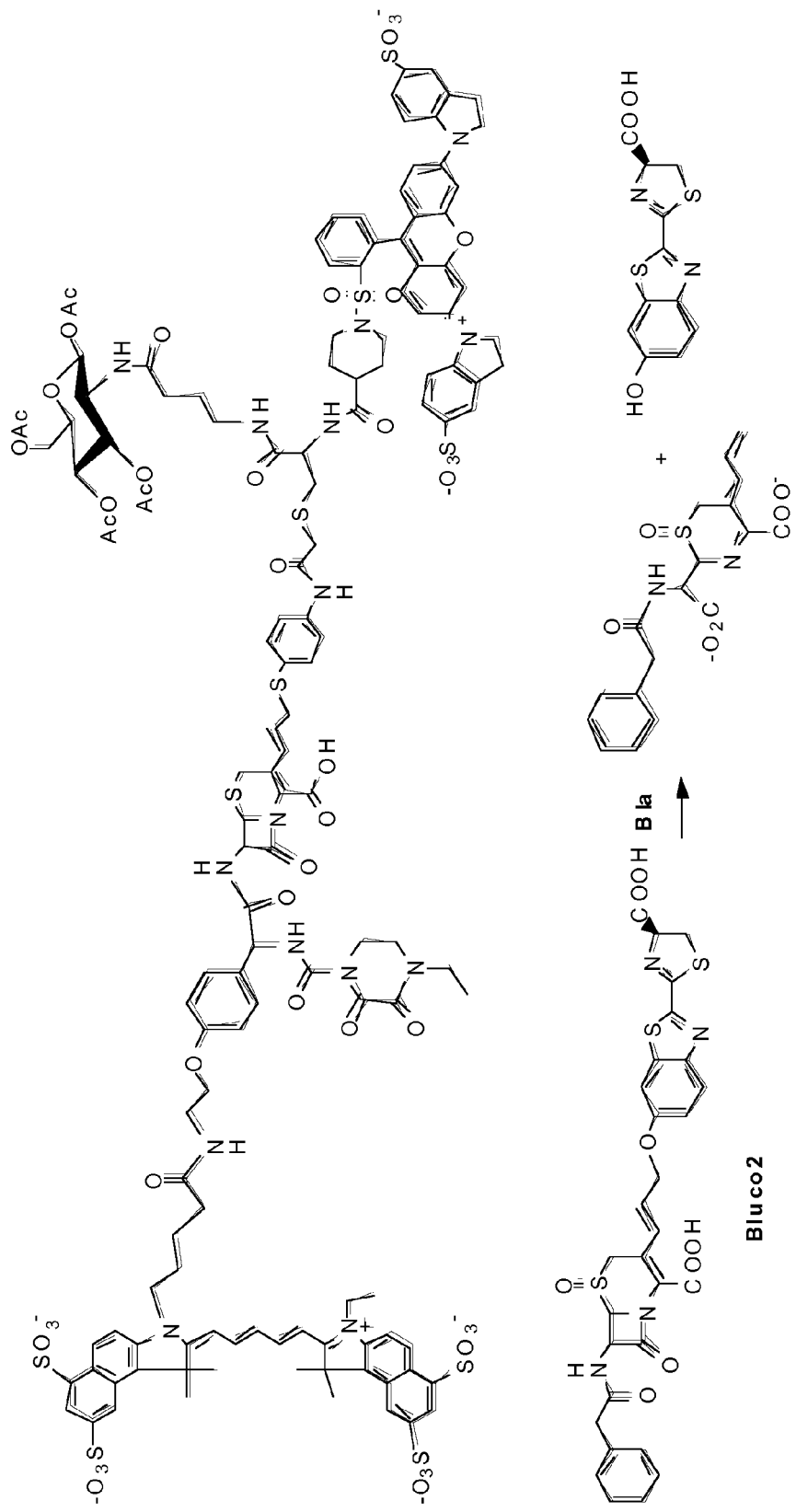

FIG. 31 displays structures of new probes containing an allylic linkage at the 3'-position.

Figure 32:
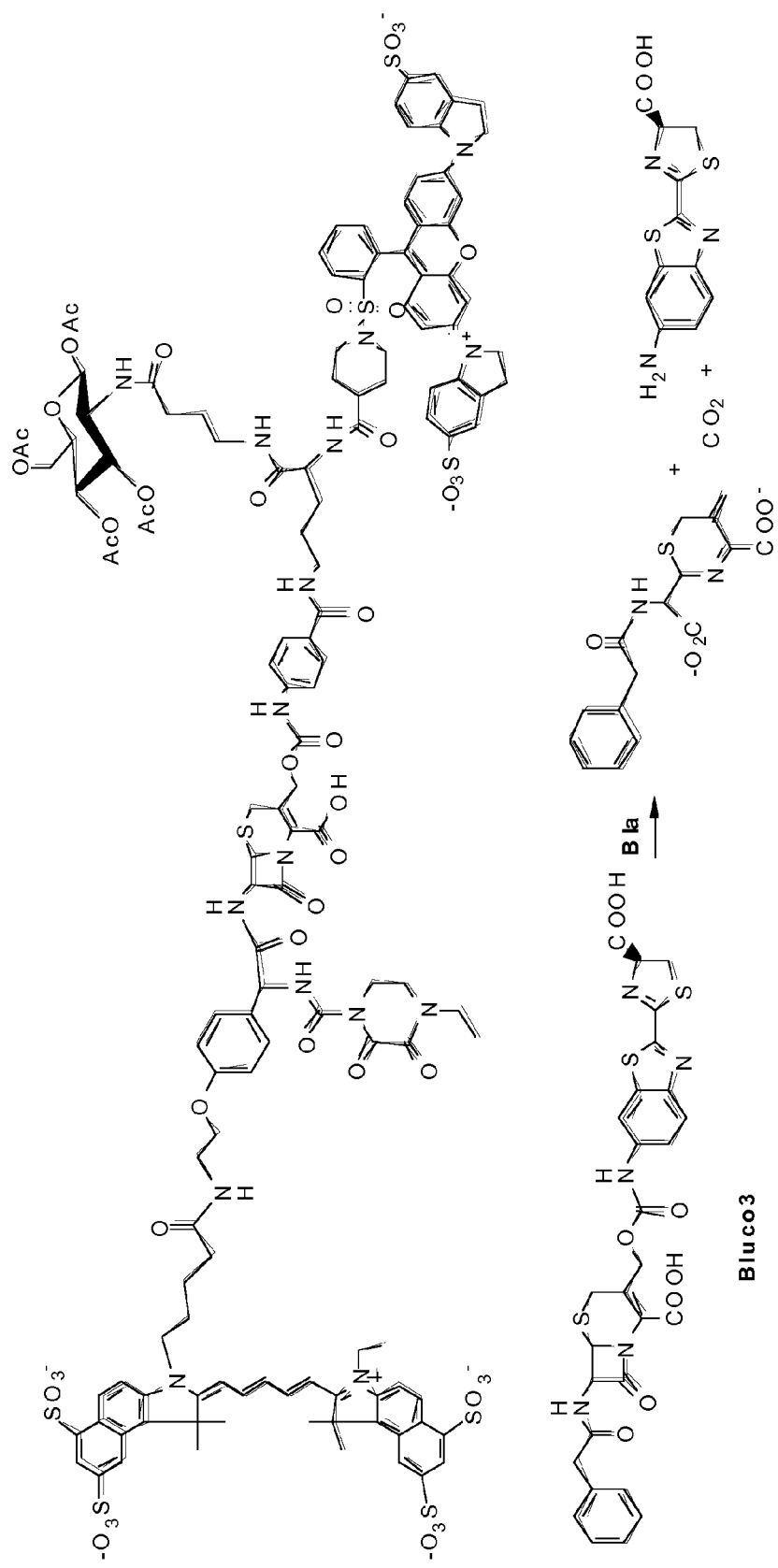
Figure 33A:
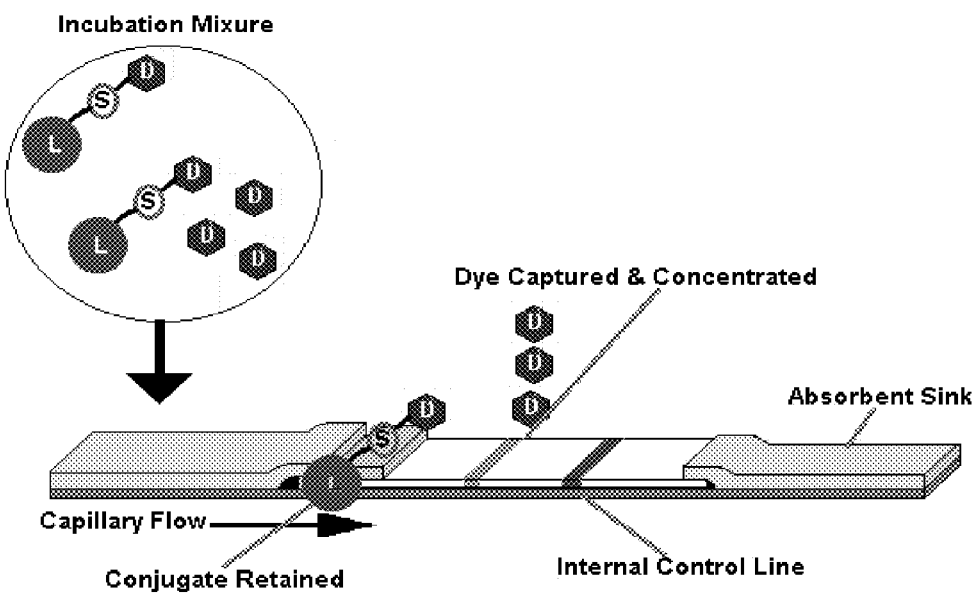
Figure 33B:
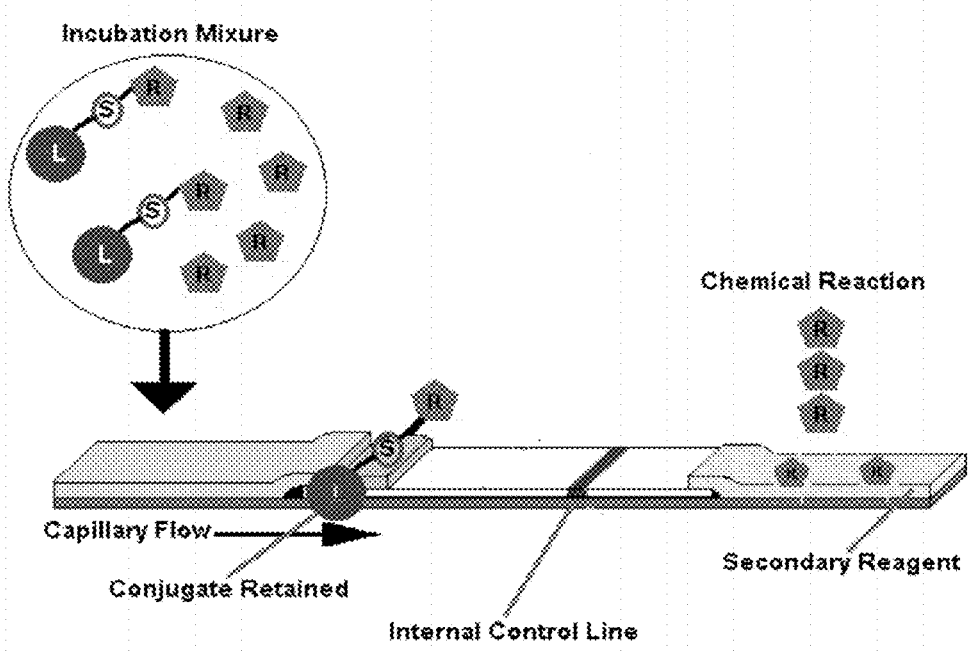
Figure 33C:
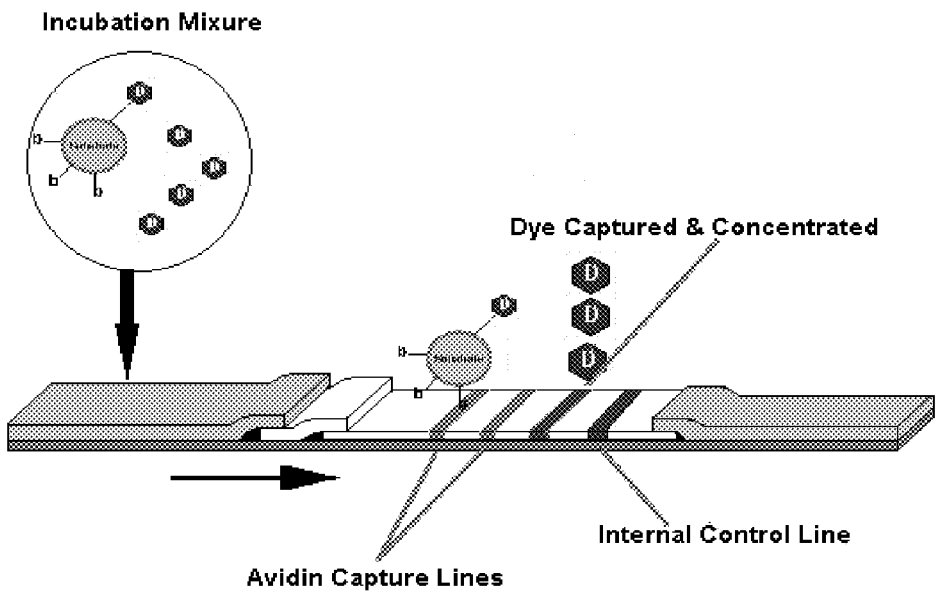
Figure 33D:
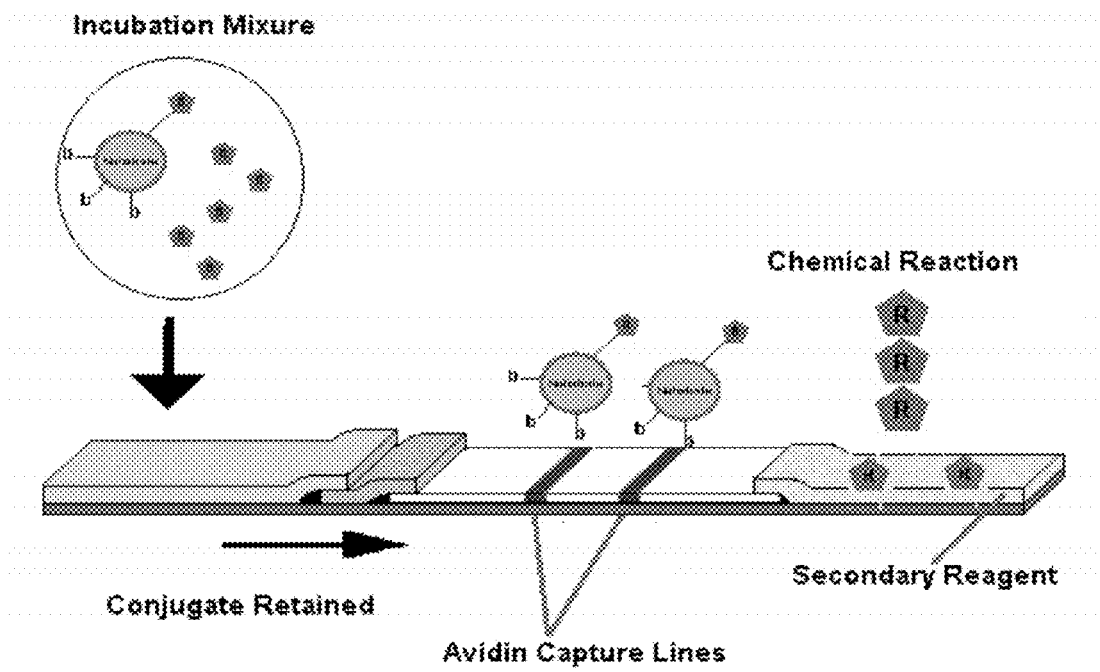

FIG. 32 depicts structures of new probes containing a carbamate linkage at the 3'-position.

FIGS. 33A-33D depict visible detection systems for diagnostic assays utilizing a conjugate/substrate/colored dye (FIG. 33A) or conjugate substrate/color producing chemical reagent (FIG. 33B) linked to a latex particle or microsphere and a conjugate/substrate/colored dye (FIG. 33C) or conjugate substrate/color producing chemical reagent (FIG. 33D) linked to a biotin.

DETAILED DESCRIPTION OF THE INVENTION

As used herein the specification, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. Furthermore, unless otherwise required by context, singular terms shall include pluralities and plural terms shall include the singular.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, the term "contacting" refers to any suitable method of bringing a fluorogenic substrate, e.g., a fluorogenic compound, a fluorescent protein, a luminescent protein, or a colorimetric protein or other colorimetric reagent or derivative thereof or a radiolabeled substrate suitable for PET or SPECT imaging into contact with a pathogenic bacteria, e.g., but not limited to *Mycobacterium tuberculosis* (Mbt), *Mycobacterium bovis* (*M. bovis*), *Mycobacterium avium* (*M. avium*), *Mycobacterium tuberculosis* complex or *Mycobacterium avium* complex, or with a species of *Bacteroides, Clostridium, Streptococcus, Staphylococcus, Pseudomonas,*

Haemophilus, Legionella, Escherichia, Salmonella, Shigella, or Listeria or with the beta-lactamase or other enzyme or protein specific to the pathogenic bacteria in vivo or in vitro in a biological sample. In vitro or ex vivo this is achieved by exposing one or more of the bacterial cells or the beta-lactamase or other enzyme or protein to the fluorogenic substrate or fluorogenic compound or the fluorescent, the luminescent or the colorimetric protein or other colorimetric reagent or derivative thereof in a suitable medium. The bacterial cells or the beta-lactamase or other enzyme or protein are in samples obtained from the subject. The bacterial cells may or may not comprise a viable sample. The beta-lactamase or other enzymes or proteins may be contacted in viable bacterial cells, may be extracted by known and standard methods from bacterial cells, may be present per se in the biological sample, or may comprise a recombinant system transfected into the bacterial cells by known and standard methods. The samples may be inclusive of but not restricted to pleural fluid or sputum and other body fluids inclusive of, blood, saliva, urine and stool that may have the bacteria. Alternatively, for in vitro contact, the biological sample may be obtained, for example, by swabbing, from surfaces, such as, but not limited to instruments, utensils, facilities, work surfaces, clothing, or one or more areas of interest on a person. The sample so obtained may be transferred to a suitable medium for imaging by methods known and standard in the art. For in vivo applications, any known method of administration of the fluorogenic substrate, i.e., a fluorogenic compound, fluorescent, luminescent or colorimetric protein, other colorimetric reagent or derivative thereof, or a radiolabeled substrate is suitable as described herein.

As used herein, the phrase "fluorogenic substrate" refers to a chemical compound or protein or peptide or other biologically active molecule that in the presence of a suitable enzyme yields a product that emits or generates a fluorescent or luminescent signal upon excitation with an appropriate wavelength or may produce a product that yields a colorimetric signal. For example, and without being limiting, a fluorogenic substrate may produce a fluorescent, luminescent or colorimetric product in the presence of beta-lactamase, a luciferase or beta-galactosidase or other enzyme.

As used herein, the phrase "radiolabeled substrate" refers to compound or protein or peptide or other biologically active molecule attached to or linked to or otherwise incorporated with a short-lived radioisotope that emits positrons for Positron Emission Tomography (PET) or gamma rays for Single Photon Emission Computed Tomography (SPECT).

As used herein, the phrase "beta-lactamase positive bacteria" refers to pathogenic bacteria that naturally secrete beta-lactamase enzyme or acquire beta-lactamase during pathogenesis.

As used herein, the term "subject" refers to any target of the treatment or from which a biological sample is obtained. Preferably, the subject is a mammal, more preferably, the subject is one of either cattle or human.

In one embodiment of the present invention there is provided a method for detecting a pathogenic bacteria in real time in a subject, comprising introducing into the subject or a biological sample therefrom a fluorescent, luminescent or colorimetric substrate for a beta-lactamase of the pathogenic bacteria; imaging the subject or sample at an excitation wavelength for a product from beta-lactamase activity on the substrate; and acquiring signals at a wavelength emitted by the beta-lactamase product; thereby detecting the pathogenic bacteria in the subject.

Further to this embodiment the method comprises producing a 3D reconstruction of the emitted signal to determine location of the pathogenic bacteria in the subject. In another further embodiment the method comprises diagnosing in real time a pathophysiological condition associated with the pathogenic bacteria based on an emitted signal intensity greater than a measured control signal. An example of a pathophysiological condition is tuberculosis.

In certain embodiments of the present invention the fluorescent substrate may be a fluorogenic substrate. Examples of a fluorogenic substrate are CNIR2, CNIR3, CNIR4, CNIR5, CNIR5-QSY22, CNIR7, CNIR9, CNIR10, CNIR7-TAT, a caged luciferin, a colorimetric reagent or derivatives thereof. Also, in all embodiments the imaging or excitation wavelengths and the emission wavelength independently may be from about 300 nm to about 900 nm. In certain embodiments the imaging or excitation wavelength is from about 540 nm to about 730 nm and the emitted signals may be about 650 nm to about 800 nm. In certain embodiments, colorimetric indication may be visually identified by the human eye by a color change or measured by equipment to determine an assigned numerical value. Furthermore, the pathogenic bacteria may comprise a bacterial species of Bacteroides, Clostridium, Streptococcus, Staphylococcus, Pseudomonas, Haemophilus, Legionella, Mycobacterium, Escherichia, Salmonella, Shigella, or Listeria. Particularly, the pathogenic bacteria may comprise a Mycobacterium tuberculosis complex or a Mycobacterium avium complex.

In a related embodiment of the present invention there is provided a method for imaging a pathogenic bacteria, comprising introducing into a subject or contacting a biological sample therefrom or obtained from a surface with a fluorogenic substrate for a beta-lactamase of the pathogenic bacteria; delivering to the pathogenic bacteria an excitation wavelength for a product of beta-lactamase activity on the substrate; acquiring fluorescent, luminescent or colorimetric signals emitted from the product; and producing a 3D reconstruction of the acquired signals, thereby imaging the pathogenic bacteria. In aspects of this embodiment the pathogenic bacteria may be contacted in vivo or in vitro with the fluorogenic or luminescent substrates as described supra. Also, in all aspects of this embodiment the pathogenic bacteria and the excitation and emission wavelengths are as described supra.

In another related embodiment the present invention provides a method for detecting a pathogenic bacteria in real time, comprising introducing into the subject or a biological sample therefrom a substrate for a beta-lactamase of the pathogenic bacteria; imaging the subject or sample for a product from beta-lactamase activity on the substrate; and acquiring signals at a wavelength emitted by the beta-lactamase product; thereby detecting the pathogenic bacteria in the subject.

Further to this embodiment the method comprises producing a 3D reconstruction of the emitted signal to determine location of the pathogenic bacteria in the subject. In another further embodiment, the method may comprise quantifying and differentiating infected cells from non-infected cells in the biological sample. Particularly, in this further embodiment, the steps of differentiating and/or quantifying infected cells is performed by utilizing one or more of flow cytometry, confocal microscopy or fluorescent spectrometry.

In both embodiments the substrate may be a fluorogenic substrate CDC-1, CDC-2, CDC-3, CDC-4, CDC-5, CNIR5, CNIR5.2, CNIR5-QSY22, CNIR7, CNIR7-TAT, CNIR9, CNIR10, CNIR800, CNIR800.2, CNIR800-3, XHX2-81, XHX2-91, XHX3-1, XHX3-2, XHX3-26, or XHX3-32 or a derivative or analog thereof. Alternatively, the substrate may comprise a colored dye or a chemical reagent effective to induce a color or pH change. Furthermore, the substrate may be linked to a particle, microsphere or to biotin. Also, in both embodiments the biological sample may be a sputum, pleural fluid, urine, blood, saliva, stool, or a sample obtained by swabbing an area of interest on the subject. The acquired signal may be a fluorescent, luminescent or colorimetric signal. The pathogenic bacteria, the imaging wavelength and the emission wavelength are as described supra.

In another embodiment of the present invention there is provided a method for diagnosing a pathophysiological condition associated with pathogenic bacteria in a subject, comprising administering to the subject a fluorogenic or luminescent substrate for a beta-lactamase of the pathogenic bacteria; imaging the subject at an excitation wavelength for a product of beta-lactamase activity on the substrate; and measuring in real time a fluorescent, luminescent or colorimetric signal intensity at wavelength emitted by the product; wherein a fluorescent, luminescent or colorimetric signal intensity greater than a measured control signal correlates to a diagnosis of the pathophysiological condition.

Further to this embodiment the method comprises producing a 3D reconstruction of the signal to determine the location of the microbial pathogen. In another further embodiment the method comprises administering one or more therapeutic compounds effective to treat the pathophysiological condition. Further still the method comprises re-administering the fluorogenic or luminescent substrate to the subject; and re-imaging the subject to monitor the efficacy of the therapeutic compound; wherein a decrease in emitted signal compared to the signal at diagnosis indicates a therapeutic effect on the pathophysiological condition. In all embodiments the pathophysiological condition, the pathogenic bacteria, the fluorogenic substrates and the imaging or excitation and emission wavelengths are as described supra.

In a related embodiment of the present invention there is provided a method for diagnosing a pathophysiological condition associated with a pathogenic bacteria in a subject, comprising administering to the subject or contacting a biological sample derived therefrom with a substrate for a beta-lactamase of the pathogenic bacteria; imaging the subject for a product of beta-lactamase activity on the substrate; and measuring in real time a signal intensity at a wavelength emitted by the product; wherein a signal intensity greater than a measured control signal correlates to a diagnosis of the pathophysiological condition. Further to this embodiment the method comprises producing a 3D image and administering therapeutic compound(s) appropriate for the diagnosed pathophysiological condition and readministering the substrate are as described supra. In another further embodiment the method comprises one or both of quantifying and differentiating infected cells from non-infected cells in the biological sample, as described supra.

In these embodiments the substrate may be the fluorogenic substrate, colored dye or chemical reagent as described supra. Also, the pathophysiological condition may be tuberculosis and the biological sample may be a sputum, pleural fluid, urine, blood, saliva, stool, or a sample obtained by swabbing an area of interest on the subject. The measured signal may be a fluorescent, luminescent or colorimetric signal. The pathogenic bacteria, the imaging or excitation wavelength and the emission wavelength are as described supra.

In another related embodiment of the present invention there is provided a method of diagnosing a pathophysiological condition associated with a pathogenic bacteria in a subject, comprising contacting a sample obtained from said subject with a colorimetric substrate for a beta-lactamase of the pathogenic bacteria; wherein a product of beta-lactamase activity on the substrate causes a change of color visible to the naked eye, thus indicating diagnosis. The substrate may be placed on a strip, q-tip, background or other visible indicators. The color change may be visible to the naked eye and identifiable without any equipment or excitation from an external energy source.

In yet another embodiment of the present invention there is provided a diagnostic method for detecting a mycobacterial infection in a subject, comprising obtaining a biological sample from the subject; contacting the biological sample with a fluorogenic substrate of a mycobacterial beta-lactamase enzyme; imaging the biological sample for a product of beta-lactamase activity on the fluorogenic substrate; and measuring a signal intensity at a wavelength emitted by the product; wherein a signal intensity greater than a measured control signal indicates the presence of the mycobacterial infection. Further to this embodiment the method provides repeating the above method steps one or more times to monitor therapeutic efficacy of a treatment regimen administered to the subject upon detection of the mycobacterial infection; where a decrease in the measured fluorescent signal compared to control correlates to a positive response to the treatment regimen. In another further embodiment the method comprises one or both of quantifying and differentiating infected cells from non-infected cells in the biological sample, as described supra.

In aspects of both embodiments the substrate may be a fluorogenic substrate CDC-1, CDC-2, CDC-3, CDC-4, CDC-5, CNIR5, CNIR5.2, CNIR5-QSY22, CNIR7, CNIR7-TAT, CNIR9, CNIR10, CNIR800, CNIR800.2, CNIR800-3, XHX2-81, XHX2-91, XHX3-1, XHX3-2, XHX3-26, or XHX3-32 or a derivative or analog thereof. Alternatively, the substrate may comprise a colored dye or a chemical reagent effective to induce a color or pH change. Furthermore, the substrate may be linked to a particle, microsphere or to biotin. Also, the biological sample may be a sputum, pleural fluid, urine, blood, saliva, stool, or a sample obtained by swabbing an area of interest on the subject. In addition the mycobacterial infection may be caused by *Mycobacterium tuberculosis* or *Mycobacterium tuberculosis* complex or a *Mycobacterium avium* or *Mycobacterium avium* complex. Furthermore, the measured signal may be a fluorescent, luminescent or colorimetric signal. The imaging and emission wavelengths may be as described supra.

In yet another embodiment of the present invention there is provided a method for screening for therapeutic compounds effective for treating a pathophysiological condition associated with a pathogenic bacteria in a subject, comprising selecting a potential therapeutic compound for the pathogenic bacteria; contacting the bacterial cells with a fluorescent, luminescent or colorimetric detection agent; contacting the bacterial cells with the potential therapeutic compound; and measuring a fluorescent, luminescent or colorimetric signal produced by the bacterial cells in the presence and absence of the potential therapeutic compound; wherein a decrease in signal in the presence of the therapeutic compound compared to the signal in the absence thereof indicates a therapeutic effect of the compound against the pathogenic bacteria. In this embodiment the pathophysiological condition and the pathogenic bacteria are as described supra.

In one aspect of this embodiment the pathogenic bacteria may be recombinant bacteria where the step of contacting the bacteria with the fluorescent, luminescent or colorimetric detection agent comprises transforming wild type bacteria with an expression vector comprising the fluorescent, luminescent or colorimetric detection agent. In this aspect the fluorescent, luminescent or colorimetric detection agent may comprise a fluorescent protein. Examples of a fluorescent protein are mPlum, mKeima, Mcherry, or tdTomato. Also in this aspect the expression vector may comprise a beta-galactosidase gene where the method further comprising contacting the recombinant bacterial cells with a fluorophore effective to emit a fluorescent signal in the presence of beta-galactosidase enzyme. Examples of a fluorophore are C2FDG, C12RG or DDAOG. In addition, in this aspect the expression vector may comprise a luciferase gene where the method further comprises contacting the recombinant bacterial cells with D-luciferin. Examples of luciferase are firefly luciferase, click beetle red or rLuc8.

In another aspect of this embodiment the fluorescent detection agent may be a fluorogenic substrate of the bacterial beta-lactamase. In one example the pathogenic bacteria may be contacted in vivo with the fluorogenic substrate CNIR2, CNIR3, CNIR4, CNIR5, CNIR5-QSY22, CNIR7, CNIR9, CNIR10, CNIR7-TAT, a caged luciferin, a colorimetric reagent or a derivative thereof. In another example the pathogenic bacteria may be contacted in vitro with the fluorogenic substrate CC1, CC2, CHPQ, CR2, CNIR1, or CNIR6.

In a related embodiment of the present invention there is provided a method for screening for therapeutic compounds effective for treating a pathophysiological condition associated with a pathogenic bacteria in a subject, comprising selecting a potential therapeutic compound for the pathogenic bacteria; contacting the bacterial cells or a biological sample comprising the same with a substrate of a bacterial beta-lactamase thereof; contacting the bacterial cells or the biological sample comprising the same with the potential therapeutic compound; and measuring a fluorescent, luminescent or colorimetric signal produced by the bacterial cells in the presence and absence of the potential therapeutic compound; where a decrease in signal in the presence of the therapeutic compound compared to the signal in the absence thereof indicates a therapeutic effect of the compound against the pathogenic bacteria.

In an aspect of this embodiment the substrate may be a fluorogenic substrate CDC-1, CDC-2, CDC-3, CDC-4, CDC-5, CNIR5, CNIR5.2, CNIR5-QSY22, CNIR7, CNIR7-TAT, CNIR9, CNIR10, CNIR800, CNIR800.2, CNIR800-3, XHX2-81, XHX2-91, XHX3-1, XHX3-2, XHX3-26, or XHX3-32 or a derivative or analog thereof. Alternatively, the substrate may comprise a colored dye or a chemical reagent effective to induce a color or pH change. Furthermore, the substrate may be linked to a particle, microsphere or to biotin. Also the pathogenic bacteria and the pathophysiological condition may be as described supra. In addition the signal produced by the bacterial cells may have a wavelength from about 300 nm to about 900 nm. Particularly, the produced signal may have a wavelength from about 650 nm to about 800 nm.

In yet another embodiment of the present invention there is provided a substrate for a bacterial beta-lactamase that produces a detectible fluorescent, luminescent or colorimetric signal upon beta-lactamase activity thereon. In aspects of this embodiment, the substrate may be a fluorogenic substrate CDC-1, CDC-2, CDC-3, CDC-4, CDC-5, CNIR5, CNIR5.2, CNIR5-QSY22, CNIR7, CNIR7-TAT, CNIR9, CNIR10, CNIR800, CNIR800.2, CNIR800-3, XHX2-81, XHX2-91, XHX3-1, XHX3-2, XHX3-26, or XHX3-32 or a derivative or analog thereof or may comprise a colored dye or a chemical reagent effective to produce a color or pH change upon beta-lactamase activity thereon. Also, the substrate further may comprise a particle, microsphere or a biotin linked thereto.

In yet another embodiment of the present invention there is provided a method for detecting a pathogenic bacteria in real time in a subject, comprising introducing into the subject a substrate radiolabeled with an isotope associated with gamma emission; where the substrate is for a beta-lactamase or other enzyme or protein specific to the pathogenic bacteria; imaging the subject for gamma emissions from the radiolabeled substrate during activity thereon; acquiring signals generated by the emitted gamma rays; and producing a 3D reconstruction of the concentration in the subject of the radiolabel based on intensity of the gamma ray generated signals; thereby detecting the pathogenic bacteria.

Further to this embodiment the method comprises diagnosing in real time a pathophysiological condition associated with the pathogenic bacteria based on detection thereof. In another further embodiment the method comprises administering one or more therapeutic compounds effective to treat the pathophysiological condition. In yet another further embodiment the method comprises readministering the radiolabeled substrate to the subject; and reimaging the subject to monitor the efficacy of the therapeutic compound; where a decrease in gamma emission compared to gamma emission at diagnosis indicates a therapeutic effect on the pathophysiological condition. In these further embodiments the pathophysiological condition may be tuberculosis.

In one aspect of all these embodiments the radiolabel may be a positron-emitting isotope and imaging may be via positron emission tomography (PET). In another aspect the radiolabel may be an isotope directly emitting gamma rays and imaging may be via single photon emission computed tomography (SPECT). In all aspects of these embodiments the other enzyme or protein may be a beta-lactamase-like enzyme or a penicillin-binding protein. Also, in all embodiments bacterial species may be as described supra.

In yet another embodiment of the present invention there is provided a radiolabeled substrate for a bacterial beta-lactamase suitable for PET or SPECT imaging. In this embodiment the radiolabel may be fluorine-18, nitrogen-13, oxygen-18, carbon-11, technetium-99m, iodine-123, or indium-111.

In yet another embodiment of the present invention, there is provided an assay device for visibly detecting a pathogenic bacteria in a biological sample, comprising a platform having means for receiving an incubation mixture comprising the biological sample and a color-producing substrate for a beta-lactamase enzyme associated with the pathogenic bacteria and means for capturing and concentrating a colored product produced by the beta-lactamase activity upon the substrate in fluid connection to the receiving means.

Further to this embodiment the assay device may comprise a means for allowing only the colored product to flow downstream from the receiving means. In another further embodiment the assay device may comprise an internal control downstream from the receiving means. In yet another further embodiment the assay device may comprise means for absorbing fluid downstream from the receiving means.

In all embodiments the substrate may comprise a colored dye or a chemical reagent. Also in all embodiments the substrate may be linked to a particle or a microsphere. In one aspect of these embodiments the substrate comprises a chemical reagent and the device further comprises a second reagent as means to produce color from the chemical reagent. In another aspect of these embodiments the substrate is linked to biotin and the device further comprises avidin as means to capture the biotin-linked substrate.

Provided herein are systems and methods for optical imaging of bacterial disease and/or infection. These systems and methods are extremely sensitive tools for quantification and localization of the bacteria during disease and for real-time in vivo analysis of antimicrobial drug activity. It is contemplated that these systems are effective to detect bacterial pathogens at a single cell level. These in vivo imaging (IVI) systems and methods can be applied directly to patients in a clinical setting.

The systems and methods herein are applicable to bacterial species naturally possessing or acquiring beta-lactamase activity. Without being limiting, examples of beta-lactamase positive bacterial species are *Bacteroides, Clostridium, Streptococcus, Staphylococcus, Pseudomonas, Legionella, Mycobacterium, Haemophilus, Escherichia, Salmonella, Shigella*, or *Listeria*. Particularly contemplated is the diagnosis, location and quantitation of *Mycobacterium*, such as, *Mycobacterium tuberculosis* and *Mycobacterium bovis*. Although an advantage of the systems and methods described herein is that it does not require engineering of the bacterial strain for it to be detected, it is contemplated that methods of improving expression, activity and/or secretion of the beta-lactamase to improve sensitivity of detection. As such, it is contemplated that beta-lactamase bacterial species may be detected by introducing beta-lactamase into any bacterial species or strain of interest by any applicable method that allows beta-lactamase expression and secretion at sufficient levels to allow sensitive detection thereof. This may be accomplished in vitro or in vivo using known and standard delivery methods, including using phage that are suitable delivery vehicles into mammals.

The in vivo imaging systems of the present invention may detect a fluorescent, a luminescent or a colorimetric signal produced by a compound or reporter that acts as a substrate for beta-lactamase activity. Imaging systems are well-known in the art and commercially available. For example, a sequential reporter-enzyme fluorescence (SREF) system, a sequential reporter-enzyme luminescence (SREL) system or a bioluminescent system may be used to detect products of beta-lactamase activity. Furthermore, the acquired signals may be used to produce a 3D representation useful to locate the bacterial pathogen. For these systems one of ordinary skill in the imaging arts is well able to select excitation and emission wavelengths based on the compound and/or reporter used and the type of signal to be detected. Generally, both the excitation or imaging wavelength and the emission wavelength may be about 300 nm to about 900 nm. An example of an excitation signal may be within a range of about 540 nm to about 730 nm and an emission signal within about 650 nm to about 800 nm. It also is contemplated that in vivo imaging systems of the present invention may also detect other signals, such as produced by radiation, or any detectable or readable signal produced by beta-lactamase activity upon a suitable substrate or other detection agents.

The beta-lactamase substrates of the present invention may be chemical substrates or quantum dot substrates. Substrates for imaging using SREL or SREF, for example, may be a fluorophore, a caged luciferin or other fluorescent, luminescent or colorimetric compound, reporter or other detection reagents that gives the best signal for the application needed. The substrate has very low or no toxicity at levels that allow good penetration into any tissue and a high signal to noise ratio. The signal may be a near infrared, infrared or red light signal, for example, from about 650 nm to about 800 nm.

For example, the substrates may be fluorogenic substrates or quantum dot substrates that produce a signal upon cleavage by the beta-lactamase in vitro or in vivo. Fluorogenic substrates may comprise a FRET donor, such as an indocyanine dye, e.g., Cy5, Cy5.5 or Cy7 or IRDye800 and a FRET quencher, such as a quenching group QSY21, QSY21 disulfonate, QSY22, QSY22 disulfonate or IRDyeQC-1. In addition, fluorogenic substrates may comprise peracetylated D-glucosamine to improve cell permeability and/or may be linked to a small peptide, such as, but not limited to TAT. Moreover, the substrate may be modified to improve its signal intensity, tissue penetration ability, specificity or ability to be well distributed in all tissues. Furthermore, it is contemplated that other labeling methods for tissue, cells or other compounds in combination with these substrates are useful to improve sensitivity and detection of bacterial pathogens. For example, fluorogenic substrates may comprise, but are not limited to comprising, methyl, methoxy or benzyl moieties and/or may contain cis or trans double bonds for greater release of the leaving group.

Particularly, fluorogenic substrates may detect beta-lactamase activity in a bacterial cell culture or in a single cultured bacterial cell in vitro. Examples of chemical fluorogenic substrates are CC1, CC2, CHPQ, CR2, CNIR1, or CNIR6. Alternatively, for in vivo imaging applications, fluorogenic substrates may be CNIR2, CNIR3, CNIR4, CNIR5, CNIR5-QSY22, CNIR7, CNIR9, CNIR10, CNIR7-TAT or CNIR800 or derivates or analogs thereof or fluorogenic substrates similar to CNIR5, such as CNIR5.2, or similar to CNIR800, such as CNIR800.2 or CNIR800-3. Also provided are the fluorogenic substrates CDC-1, CDC-2, CDC-3, CDC-4, and CDC-5 or derivatives or analogs thereof that release 7-hydroxycoumarin as the fluorophore upon hydrolysis with Mtb BlaC or the fluorogenic compounds similar to CDC-1, CDC-2, CDC-3, CDC-4, and CDC-5, particularly CDC-5, such as, but not limited to, XHX2-81, XHX2-91, XHX3-1, XHX3-2, XHX3-26, or XHX3-32 or derivatives or analogs thereof for in vitro and in vivo imaging. These fluorogenic substrates are useful in a sequential reporter-enzyme fluorescence (SREF) system. It is contemplated the beta-lactamase substrates are effective to detect a single bacterial cell in vitro or in vivo.

Another example of a fluorogenic substrate for in vivo detection of beta-lactamase is a caged luciferin, such as, but not limited to Bluco, Bluco2 or Bluco3. This substrate comprises D-luciferin, the substrate of firefly luciferase (Fluc), and beta-lactam, the substrate of beta-lactamase. Cleavage of beta-lactam by the enzyme releases the D-luciferin, which luminesces upon oxidation by Fluc. Caged luciferins are useful in a sequential reporter-enzyme luminescence (SREL) system or other bioluminescent imaging systems.

Fluorescent proteins also may be useful for detection of bacterial pathogens in vitro and in vivo. Fluorescent proteins (FP) such as mPlum, mKeima, Mcherry and tdTomato are cloned into expression vectors. A bacterial pathogen of interest, such as *M. tuberculosis*, is transformed with the FP construct. Expression of the fluorescent protein by the bacteria results in a detectable signal upon imaging. Other imaging systems may utilize recombinant bacteria transformed to secrete other enzymes, such as beta-galactosidase, which in the presence of fluorophores, e.g., C2FDG, C12RG or DDAOG, yields a fluorescent signal. Still other imaging systems utilize other recombinant systems expressing other luciferases, such as click beetle red or rLuc8 which produce a signal in the presence of a substrate, for example, D-luciferin.

In addition substrates may comprise a colored or visible dye. Colored or visible dyes, may be, but are not limited to Texas Red, rhodamine, bromocresol dyes (multiple colors), cyanine dyes. Furthermore, substrates may comprise a chemical reagent that produces a color change upon beta-lactamase activity, such as from a change in pH or other chemically induced color change.

Alternatively, positron emission tomography (PET) or single photon emission computed tomography (SPECT) imaging systems may be used. Probes may comprise substrates for a beta-lactamase, a beta-lactamase-like enzyme or other similar enzyme or protein of the pathogenic bacteria described herein. PET and SPECT imaging techniques are well-known in the art. For PET imaging substrate probes may be labeled with a positron-emitting radioisotope, such as, but not limited to, fluorine-18, oxygen-18, carbon-11, or nitrogen-13. For SPECT imaging, substrate probes may be labeled with a gamma-emitting radioisotope, such as, but not limited to, technetium-99m, iodine-123, or indium-111. PET and SPECT probes may be synthesized and labeled using standard and well-known chemical and radiochemical synthetic techniques.

It is contemplated that the design and specificity of probes may be maximized using small molecules, such as ceferoperazone, to model the beta-lactamase enzyme pocket. Thus, using this high-throughput small molecule system, substrates may be designed that are the most sensitive for diagnostic purposes and suitable to generate a signal effective to penetrate from deep tissue that is detectable with existing imaging equipment and to prevent cross-reactivity with other bacterial species. Also, such sensitive and specific substrate probes are effective at the level of a single bacterium and can increase the amount of signal obtained therefrom between 100- to 1000-fold. Also, it is contemplated that beta-lactamase-like enzymes and penicillin-binding proteins other than beta-lactamase in *M. tuberculosis* can be designed to improve probe specificity.

The systems and methods described herein are effective to detect, locate, quantify, and determine viability of a bacterial pathogen in real time. Imaging may be performed in vitro with a cell culture or single cultured cell or ex vivo with a clinical sample or specimen using the SREL or SREF or in vivo within a subject using any of the disclosed imaging systems. Samples used in vitro may include, but are not restricted to biopsies, pleural fluid, sputum and other body fluids inclusive of blood, saliva, urine and stool that may have the bacterial pathogen. Thus, the systems and methods provided herein are effective to diagnose a pathophysiological condition, such as a disease or infection, associated with a bacterial pathogen. Because very low levels, including a single bacterium, can be detected, diagnosis can be immediate and at an earlier point of infection than current diagnostic methods. The systems and methods described herein may be utilized for testing and regular screening of health care workers who may be at risk of bacterial infection. Additionally, these systems and methods can also be used for screening and detecting contamination on instruments, utensils, facilities, work surfaces, clothing and people. Since methicillin-resistant *Staphylococcus aureus* (MRSA) infections are present on up to 40% of health care workers and major areas of infection are nasal passages and cracks in hands caused by over washing, the instant invention is useful as a screening method for bacterial pathogens in health care centers and workers. These systems and methods may be used in agricultural and zoological applications for detection of beta-lactamase as necessary.

Also, correlation of signal strength to quantity of bacteria is well within the limits of current imaging technology. Thus, efficacy of compounds, drugs, pharmaceutical compositions or other therapeutic agents can be monitored in real time. The systems and methods described herein thus provide a high-throughput system for screening antibacterial agents. Because the detection of beta-lactamase requires bacterial viability, enzyme levels in the presence of one or more therapeutic agents provide a measure of antimicrobial activity. Use of substrates appropriate for the particular bacteria allows rapid measurement of changes in beta-lactamase levels and nearly immediate determination of the effectiveness of the therapeutic agent. Throughput systems are useful for single samples to thousands at a time in microplates.

More particularly, the REF systems described herein are useful for many other in vitro methods for detecting and quantifying infected cells, using flow cytometer, confocal microscopy, and or fluorescent spectrometer. Once the beta-lactamase substrate is in cells, beta-lactamase secreted by the intracellular bacteria cleaves the beta-lactam ring thus labeling the infected cells with the near infrared fluorescent color. Using flow-cytometry, the infected and non-infected cells can be differentiated and quantified. Also, using a different color labeled bacterium, for example, but not limited to, a green fluorescent protein labeled bacterium and cryosection, the infected tissue is visualized and analyzed with a fluorescent confocal microscope. Particularly, in a non-limiting example, if DAPI, which generates blue color, is utilized to stain the cell nuclei, one could see the green color bacteria and red color cleaved beta-lactamase substrate accumulated in the cytoplasm. In addition since the substrate of the beta-lactamase can label the infected cells, using the specific excitation and emission wavelengths of the cleaved substrate, the infected cells or homogenized infected tissues are quantified with a fluorescent spectrometer.

The following examples are given for the purpose of illustrating various embodiments of the invention and are not meant to limit the present invention in any fashion.

EXAMPLE 1

Detection of Bla in *M. tuberculosis* in Culture

Potential fluoregenic substrate compounds and known compounds, including Nitrocefin (Calbiochem), CENTA Bla substrate (Calbiochem), Fluorocillin Green (Molecular Probes), CCF2-AM (Invitrogen) and CCF4-AM (Invitrogen), are compared for detection of Bla in Mtb using whole cells and whole cell lysates grown to early log-phase. Dilutions are assayed for all of these samples to determine the minimal number of bacteria or amount of lysate that results in significant signal. Titers are carried out to determine the number of actual CFU used, before and after assays with intact cells and before lysis for lysates. Both the sensitivity and reproducibility are evaluated in quadruplicate spectrophotometrically using 96-well plates incubated at 37° C. in bacterial culture medium from 15-120 min. Initially, compounds are used at concentrations recommended by the manufacturer and for CNIR5, 2 nM, i.e., that used for in vivo imaging. Different concentrations of the most sensitive and reproducible compounds are evaluated in culture medium to determine minimal concentrations needed for maximal signal. Controls for these experiments include the positive controls *M. smegmatis* and commercially available Bla (Sigma) and the negative control is the Mtb blaC mutant (PM638, provided by Dr. M. Pavelka, University of Rochester) that lacks Bla (1). The production of Bla by BCG also is evaluated because in some cases BCG is used for IVI at BL2 where a wider range of imaging equipment are readily available.

Evaluate Recombinant Bla Constructs in blaC Mutant and Wild-Type Tuberculosis

Two multi-copy and two single-copy vectors are used for expression of Bla in Mtb. The multi-copy vectors are based on pJDC89 that carries the hsp60 promoter (Phsp60) from pMV262 which has been shown to express genes at moderate levels. This vector also carries hygromycin resistance, a polylinker downstream of Phsp60, an *E. coli* origin of replication and the mycobacterial pAL5000 origin of replication. In order to increase expression from this vector, Phsp60 is replaced with the L5 promoter (PL5), which expresses genes at 50- to 100-fold higher levels than Phsp60. Both promoters are relatively constitutive and should be expressed under most in vivo conditions. Most cloning, unless otherwise mentioned, is carried out using the In-Fusion 2.0 PCR cloning system (Clontech) that allows direct cloning of fragments into any linearized construct using 15 bp minimal regions of homology on primers used for PCR of a region of interest.

The two constructed vectors are modified to Gateway (Invitrogen) donor vectors by cloning a PCR fragment containing the ccdB gene and both left and right Gateway recombination sequences downstream of each promoter. Vectors that carry this region must be maintained in the ccdB Survivor strain that allows maintenance of this region; whereas, in other *E. coli* strains this region would be lethal and is used to prevent maintenance of non-recombinant vector during cloning. These promoters and associated Gateway regions are cloned into pYUB412, which carries hygromycin resistance, an *E. coli* origin of replication, a L5 phage attachment site (attP) and L5 recombinase so that it integrates in the attB site within the mycobacterial chromosome and is maintained by mycobacteria stably in single-copy. The Mtb Bla is cloned into each of these vectors by PCR using primers that carry the Gateway recombination sequences through the Gateway BP reaction (Invitrogen). These vectors are transformed into Mtb and the blaC mutant by electroporation as described (2). The resulting Mtb strains are evaluated for detection using the in vitro assays described for analysis of the endogenous Bla and signal intensity compared to that of the blaC mutant as a negative control and wild type with the appropriate vector backbone alone.

Although CNIR5 is highly membrane permeant, the strength of signal may be increased by targeting Bla to the host cell membrane that has a larger surface area for the reporter than the bacteria alone and improves access to the compound. Since the mycobacterial phagosome is not static, interacting with several lipid and receptor recycling pathways as well as having several markers present in recycling endosomes, properly targeted proteins should have access to the plasma membrane of the host cell via the mycobacterial phagosome. The Mtb Bla is secreted from the bacteria via the TAT signal located in its amino terminus, making a carboxy terminal tag directing this protein to the plasma membrane ideal. Glycosylphosphatidylinositol (GPI) anchored proteins, such as CD14 that is expressed well on the surface of macrophages, localize to the plasma membrane through a carboxy-terminal signal sequence.

A fusion (Bla::GPI) is constructed with the carboxy-terminal 24 amino acid GPI anchor protein signal sequence from CD14 and Bla from Mtb. This fusion protein then is placed into all four expression systems for Mtb using the Gateway system and transformed into both wild type Mtb and the blaC mutant. The resulting strains expressing Bla::GPI, the blaC mutant as a negative control and the original Bla are evaluated for their level of Bla on the surface of infected macrophages using the intracellular assays. Both intact infected macrophages and those lysed with 0.1% triton are examined.

Fluorescent Spectra of Substrates Before and after Hydrolysis

The excitation and emission spectra are collected in 1 mL of PBS solution at 1 μM concentration. To this solution, 10 nM of purified Bla is added, and excitation and emission spectra are collected again until there is no further change. The increase in the fluorescence signal of the probes after Bla hydrolysis is estimated by comparing the emission intensity at 690 nm which is the peak emission wavelength.

In Vitro Enzymatic Kinetics of Probes as Bla Substrate

The rate of increase (v) in fluorescence intensity at ~690 nm is used as a measure of the rate of probe hydrolysis. The rate (v) is measured at different concentrations of 5, 10, 20, 50, 80 μM at a concentration of 1 nM of Mtb Bla. A double-reciprocal plot of the hydrolysis rate of the substrate (1/v) versus substrate concentration (1/[probe]) is used to estimate the values of $k_{cat}$ and $K_m$ of the probe for Bla hydrolysis.

Biostability of the Substrate

The rate of spontaneous hydrolysis of the substrate under physiological conditions also can be estimated from the rate of increase in fluorescence intensity at ~690 nm. The stability of the substrate in aqueous buffer and in serum can thus be readily assessed by fluorescence quantitation after incubation for 1 hr at room temperature.

Imaging Bla Expression in Cultured Cells

Substrate is tested with Bla transfected (cmv-bla) and wild type Jurkat and C6 glioma cell lines, and image with a fluorescence microscope, using published imaging conditions (3).

Linear Correlation Between mRNA Levels and NIRF Signals

Wild-type and cmv-bla Jurkat cells are mixed at various ratios (10%, 20%, 40%, 60%, and 80% of cmv-bla cells) at a cell density of $5 \times 10^5$/mL. After incubation of 5 μM of substrate in each mixture of cells for 30 min, each sample is washed with cold PBS, centrifuged and lysed. Fluorescence measurements are taken on the final supernatants. The levels of mRNA and enzyme of Bla are quantified using northern analysis. A plot of the mRNA concentration vs. the Cy5.5 fluorescence intensity reveals whether there is a linear relationship between the two.

Localization and Regulation of Tuberculosis Beta-Lactamase in Culture

Transcription of Bla is examined by qRT-PCR throughout the Mtb growth curve inoculated at an O.D. of 0.05 and grown until stationary phase (O.D.=2). Transcript levels are evaluated by isolating RNA daily from aliquots of the same culture and all cultures are grown in triplicate. RNA isolation (4) and qRT-PCR using SYBR Green (5) are carried out as described previously. RNA levels are confirmed by Northern blot at one or two key points in the growth curve and all measurements are normalized against 16S rRNA. Data is compared to measurement of Bla activity with Nitrocefin under the same conditions using whole bacteria and whole cell lysates.

The ability of beta-lactams to induce blaC is examined. RNA transcripts are analyzed in the presence and absence of beta-lactams in the same manner as throughout the growth curve. 50, 250 and 500 μg/ml of carbenicillin, which kills Bla-negative Mtb, is co-incubated with Mtb grown to early log phase for two hours and the levels of blaC transcript are determined along with the Bla activity in whole cells and whole cell lysates. Levels of Bla are quantitated using a standard curve constructed using commercially available Bla (Sigma) and the Mtb blaC mutant grown in the same manner will be included as a negative control for Bla activity.

Bla Detection in Macrophages

Basically, J774A.1 cells are seeded at $1 \times 10^4$ cells/well in 96-well flat bottom plates and incubated overnight at 37° C. Single-cell suspensions of Mtb grown to early log phase are added at various multiplicities of infection from 1000 to 0.001 bacteria per cell and incubated at 37° C. for 30 min. The wells are then washed twice with PBS and fresh medium with 200 μg/ml amikacin added and incubated for 2 h at 37° C. to kill extracellular bacteria. The wells are then washed with PBS and incubated in fresh medium plus various concentrations of the test compound for between 60 and 180 min prior to measurement of the signal spectrophotometrically. Duplicate wells are lysed with 0.1% Triton X-100 prior to adding the compounds to evaluate the role of host cell permeability in the measurements obtained.

At all time points four untreated wells are used to determine the number of CFU associated with the cells. Localization of the signal is confirmed by fluorescent microscopy for those compounds that prove the most effective. Microscopy assays are carried out in a similar manner, but using eight-well chamber slides to locate the signal, determine the percentage of bacteria with a positive signal and to evaluate the intensity of localized signal.

Bioassay and Pharmacokinetics

Anesthetized mice are sacrificed by cervical dislocation at different time intervals (30 min, 240 min, 12 hr, 24 hr, 48 hr, and 72 hr) postinjection (three mice at each time point). Blood samples are collected by cardiac puncture and tissues (tumors, heart, kidney, liver, bladder, stomach, brain, pancreas, small and large intestine, lung, and spleen) are harvested rapidly to measure the near-infrared fluorescence by a fluorometer. Data is expressed as fluorescence unit (FU) of per gram of tissue [FU/(g tissue)].

Beta-Lactamase Activity Assay

The enzyme level of Bla in the xenografted tumors is measured using the following protocol: wash the harvested tumor twice with cold PBS; add lysis buffer from Promega (4 mL/g tissue), and homogenize the tissue solution; freeze and thaw the homogenate three times, and collect the supernatant by centrifugation; assay the Bla activity using the fluorogenic substrate CC1. The mRNA of Bla in cmv-bla tumors is verified by following RNA extraction protocol from Qiagen Inc. and running RT-PCR assay. These measurements validate whether the observed near-infrared signal in cmv-bla transfected tumors is correlated with Bla activity.

Determination of Bla RNA Expression In Vivo

Bla RNA expressed in vivo is extracted using a standard RNA extraction protocol for tuberculosis (6) and running qRT-PCR relative to the constitutive control rRNA gene. These measurements provide a means to evaluate the levels of expression of Bla in all tissues as compared to the levels of IVI signal observed. Should harvested RNA levels be below detectable levels by RT-PCR, yet quantifiable CFU are present in the tissues, the cDNA is amplified prior to RT-PCR using phi29 polymerase (Fidelity Systems) that has the ability to amplify DNA in a linear fashion at high fidelity, allowing true quantitation of levels of template post-amplification.

Expression, Stability and Virulence of Bla Strains In Vivo

Eight groups of four Balb/c mice are infected by aerosol with between 100-1000 cfu/lung. Bacterial strains are thawed from −80° C. stocks, passed through a 27 G syringe needle 2× to produce single cell suspensions and used for aerosol infections. Aerosol infections are carried out using the 'Madison' chamber constructed at the University of Wisconsin that is designed to deliver droplet nuclei directly to the alveolar spaces (7-10). Infections with Mtb are carried out in certified ABSL3 facilities designed to handle virulent tuberculosis strains. Infected mice are housed in ABSL3 containment at the Center for Comparative Medicine until necropsy. One group of four mice for each bacterial strain (blaC and WT) are necropsied at all time points (1, 14, 28 and 72 days) to determine CFU, RNA levels for blaC and Bla activity in lungs and spleen. RNA transcript levels and Bla activity using Nitrocefin as described herein.

Stability and effects on virulence of recombinant Bla expression in vivo is examined for two recombinant strains that display promise for IVI. Twelve groups of four Balb/c mice are infected by aerosol with between 100-1000 cfu/lung, as described above. One group of four mice for each bacterial strain (wild-type, construct 1 and construct 2) will be necropsied at all time points (1, 14, 28 and 72 days) to determine CFU, carry out histopathology, determine the presence of the appropriate construct and Bla activity in lungs and spleen. The percentage of the bacterial population that carry the construct is determined using Bla assays conducted on at least 20 individual colonies from the CFU titer plates. Bla activity assays are conducted on homogenized tissues to evaluate overall levels of Bla remaining Bla activity will be evaluated using Nitrocefin as described herein.

EXAMPLE 2

Intra-Vital Microscopy Imaging Using the Cell Transplantation Model

Universal donor Tr, CD8+ T cells, monocytes, macrophages and dendritic cells are transplanted into syngeneic mice infected with BCG, and the distribution of these cells over time are imaged with in vivo bioluminescence imaging (BLI) and image-guided intravital microscopy (IVM). A line of transgenic mice in which luciferase is produced by the beta-actin promoter, provide a source of tissues and cells that will emit light in non-transgenic animals (11-12). This mouse line (L2G85), shows bright bioluminescence from the firefly luciferase (Fluc), but weak GFP fluorescence, so it was mated with a separate line exhibiting strong GFP expression and fluorescence in lymphocytes. The spatial distribution of universal donor stem cells and other cells can thus be followed by BLI in the recipient as they expand, re-distribute or are cleared, and the cells detected can be subsequently visualized by IVM utilizing GFP.

The L2G85 mice are constructed in the FVB background, so FVB/NJ (Jackson Labs) wild type mice are used as recipients for cells from L2G85, preventing rejection of transplanted cells. A total of 80 FVB/NJ mice are infected intranasally with $10^4$ CFU of BCG in 20 μl saline. Four mice are sacrificed at 24 h to determine initial CFU in lungs post-infection. At 14 days post-infection four additional mice are sacrificed for histopathology and to determine CFU in lungs and spleens. Also at 14 days, the remaining 72 mice are divided into groups of 4 and have L2G85 Tr, CD8 T cells, monocytes, macrophages, dendritic cells or no cells (control) introduced by the tail vein I.V. At 28, 42 and 56 days six groups of four mice (including control) are imaged as described (12) in the presence of D-luciferin.

Imaging is followed up by more detailed examination of obvious lesions by intra-vital microscopy (IVM) using the fiber optic confocal fluorescent microscope (Cell-viZio, Mauna Kea). IVM uses a flexible mini-probe composed of tens of thousands of optical fibres. General anaesthesia is given and the region is probed via a small incision that rapidly heals, preventing the need to sacrifice animals after surgery and allowing visualization at the cellular level.

Control mice are sacrificed after imaging to determine CFU in lungs and other organs where signal is observed in the mice where cells have been introduced. Dorsal, ventral and two lateral images are obtained to better determine the origin of photon emission. Further confirmation is obtained in a subset of animals by dissecting the tissues, incubating fresh tissues in D-luciferin, and imaging them without the overlying tissues. A detailed histopathology is conducted on all apparently infected tissues for fluorescent microscopy to visualize GFP expressing transplant cells and carry out haemotoxylin and eosin and acid fast stains to identify bacteria and cells within tissues.

In Vivo Imaging for Individual Bacteria and Immune Cells During Granuloma Formation Using the transplantation model, two transplanted cell types that best allow visualization of granuloma formation are selected to use to visualize both the bacteria and host cells together in live mice. Three time points are chosen where lesions are just becoming visible, well formed and at the latest time point where signal can be observed from the transplanted cells. A total of 32 FVB/NJ mice are infected intranasally with $10^4$ CFU of BCG expressing an IVI reporter, e.g. tdTomato, in 20 μl saline. An additional group of four control mice are uninfected. Four experimental mice are sacrificed at 24 h to determine initial CFU in lungs post-infection. At 14 days post-infection four additional experimental mice are sacrificed for histopathology and to determine CFU in lungs and spleens. Also at 14 days, the remaining 24 mice are divided into groups of 4 and have L2G85 cells that allow visualization of granuloma formation introduced by the tail vein I.V. into 12 of them with 12 having no cells as controls. At three time points two groups of four mice (cells vs. no cells) are imaged as described (12) in the presence of D-luciferin.

Imaging is followed up by more detailed examination of obvious lesions by intra-vital microscopy (IVM) using the fiber optic confocal fluorescent microscope (Cell-viZio, Mauna Kea). General anaesthesia is given and the region is probed via a small incision. Control mice are sacrificed after imaging to determine CFU in lungs and other organs where signal is observed in the mice where cells have been introduced. Dorsal, ventral and two lateral images are obtained to better determine the origin of photon emission. In a subset of animals, further confirmation is obtained by dissecting the tissues, incubating fresh tissues in D-luciferin, and imaging them without the overlying tissues. Filter sets are used for both the transplant cells and the bacterial reporter signal in dissected tissues. A detailed histopathology is conducted on all apparently infected tissues for fluorescent microscopy to visualize GFP expressing transplant cells as well as the bacterial reporter signal and to carry out haemotoxylin and eosin and acid fast stains to identify bacteria and cells within tissues.

Imagine Analysis

The collected images are processed on a PC computer using commercially available software, Living Image, from Xenogen Inc. Regions of interest (ROI) are drawn over the tumors on whole-body fluorescence images. One of the key features of the IVIS Imaging system is that it is calibrated against a National Institute of Standards and Technology (NIST) traceable spectral radiance source. This calibration provides the conversion of CCD camera counts to radiance on the subject surface by taking into account loses through the optics and apertures (f/stop) and accounting for image time and binning. The resulting image is thus displayed in physical units of surface radiance (photons/sec/cm$^2$/sr). The integrated signal from ROI (at a unit of photons/sec) from the infected mice, control mice and normal tissues is compared across different mice (infected:control:normal tissues ratio). Statistical analysis will be performed using GraphPad Prism 3.0 ($P<0.05$, GraphPad Software, San Diego, Calif.).

EXAMPLE 3

Crystallization of M. Tuberculosis BlaC and BlaC Mutant Enzymes

Very good crystals of BlaC were obtained after a few months of crystallization. Co-crystals with penicillin were produced using crystallization conditions of 0.1M Tris-HCl, pH 8.0, 20.M $NH_4H_2PO_4$. These crystals allowed visualization of the intact protein active site and intermediate, but the initial bound substrate was not visible due to turnover in the crystal itself. To overcome this barrier, a Mtb BlaC mutant enzyme was constructed with the mutation in the Glu residue involved in hydrolysis (E166A) that allows trapping of the acy-intermediate on the enzyme and visualization of the specific interactions required for catalysis. This mutant has now been crystallized with a rapid, i.e., about two weeks, crystallization process yielding high quality crystals of Mtb BlaC mutant that are ready to be soaked with substrate (FIG. 1A). It is demonstrated that substrate can be incorporated into the Mtb BlaC mutant crystals with direct soaking overnight. After removal into fresh solution, the crystals retain the substrate, as shown for CNIR4 in FIG. 1B. Direct soaking provides for a more rapid analysis of multiple substrates. The crystallized BlaC mutant enzyme has enabled a first identification of the hydrolyzed intermediate structure of a lead compound, cefotaxime (FIG. 1C) which is useful in elucidating the mechanism of BlaC catalysis to improve the design of substrate compounds.

EXAMPLE 4

Fluorogenic Substrates for Beta-Lactamase Detection: CC1, CC2, CHPQ, and CR2

Figure 2C:
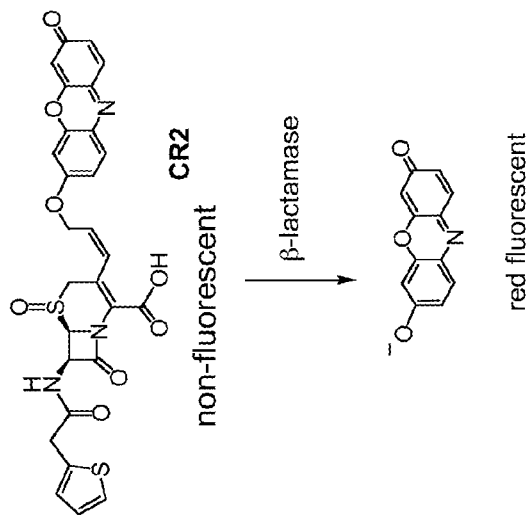
FIGS. 2A-2C depict the structures of CC1 and CC2 (FIG. 2A), CHPQ (FIG. 2B), and CR2 (FIG. 2C) before and after hydrolysis by beta-lactamase.
Figure 2B:
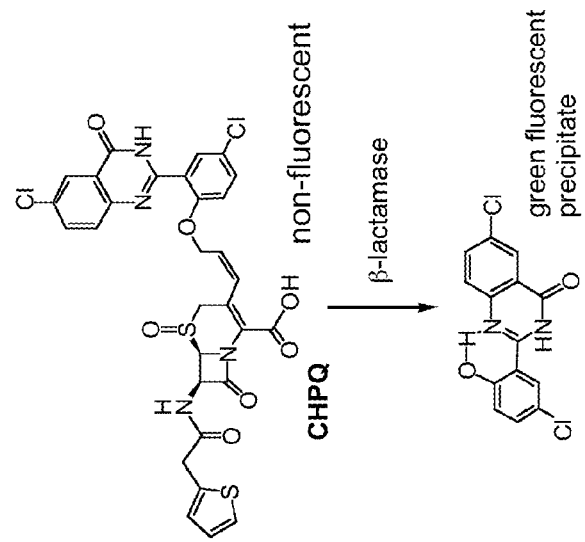
Figure 2A:
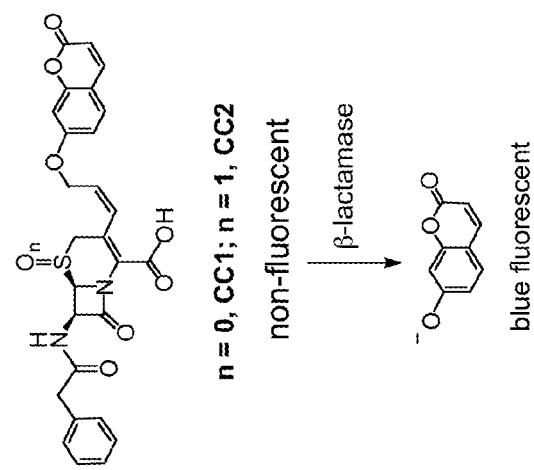

Fluorogenic compounds CC1, CC2, CHPQ, and CR2 are effective for detecting Bla activity in vitro and in single cultured cells. These probes are not fluorescent before the hydrolysis by Bla and become fluorescent after the Bla reaction (FIGS. 2A-2C). A range of different fluorescence emissions can be selected as needed to detect Bla: from blue with CC1 and CC2, green with CHPQ to red CR2). These new fluorogenic substrates are smaller than CCF2, easy to make, simple to use, have high sensitivity for detecting Bla activity and facilitate detection of Bla activity in diverse biological samples.

The insertion of an olefin group between the 3' carbon of the lactam and the leaving group helps improve the kinetic efficiency of hydrolysis by Bla. For example, for CC1, the value of $k_{cat}$ is 174 s$^{-1}$, but the value of $k_{cat}$ of its analog without the inserted double bond is just 35 s$^{-1}$. There is about a 5-fold increase in the catalytic efficiency. It is contemplated that this design can serve as a general strategy to create a wide variety of fluorogenic substrates for Bla, including near-infrared substrates for whole animal fluorescence imaging.

Also, it is contemplated that probes may be improved with a novel quencher QC-1 and near-infrared fluorophore IRDye 800CW. In addition, the IRDye-based probes may be modified by the addition of sulfonate groups.

CNIR1, CNIR2, CNIR3, CNIR4, CNIR 5, CNIR9, and CNIR10

Figure 3:
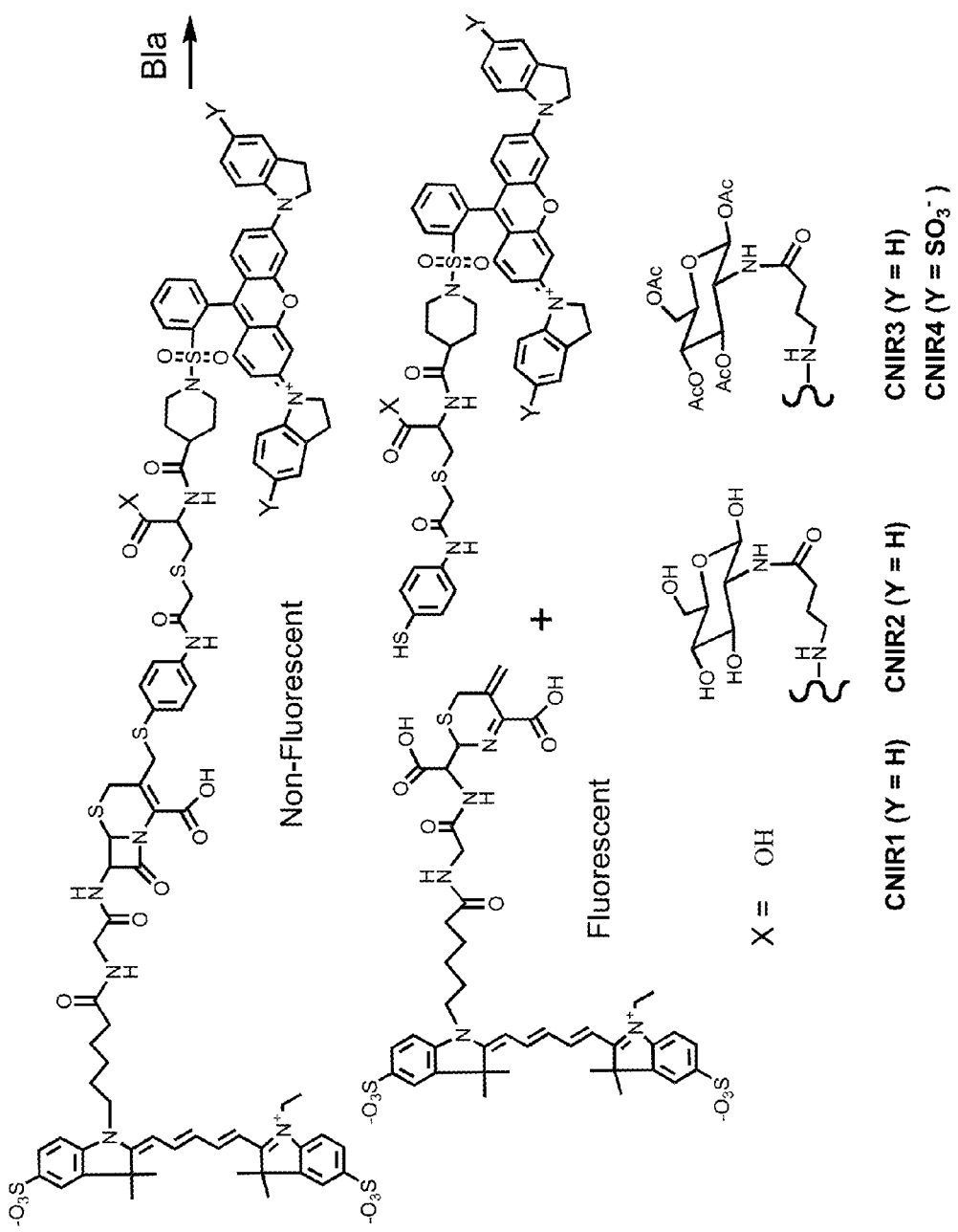
FIG. 3 depicts the structures of CNIR1, CNIR2, CNIR3, and CNIR4 and their hydrolysis by beta-lactamase.
Figure 6A:
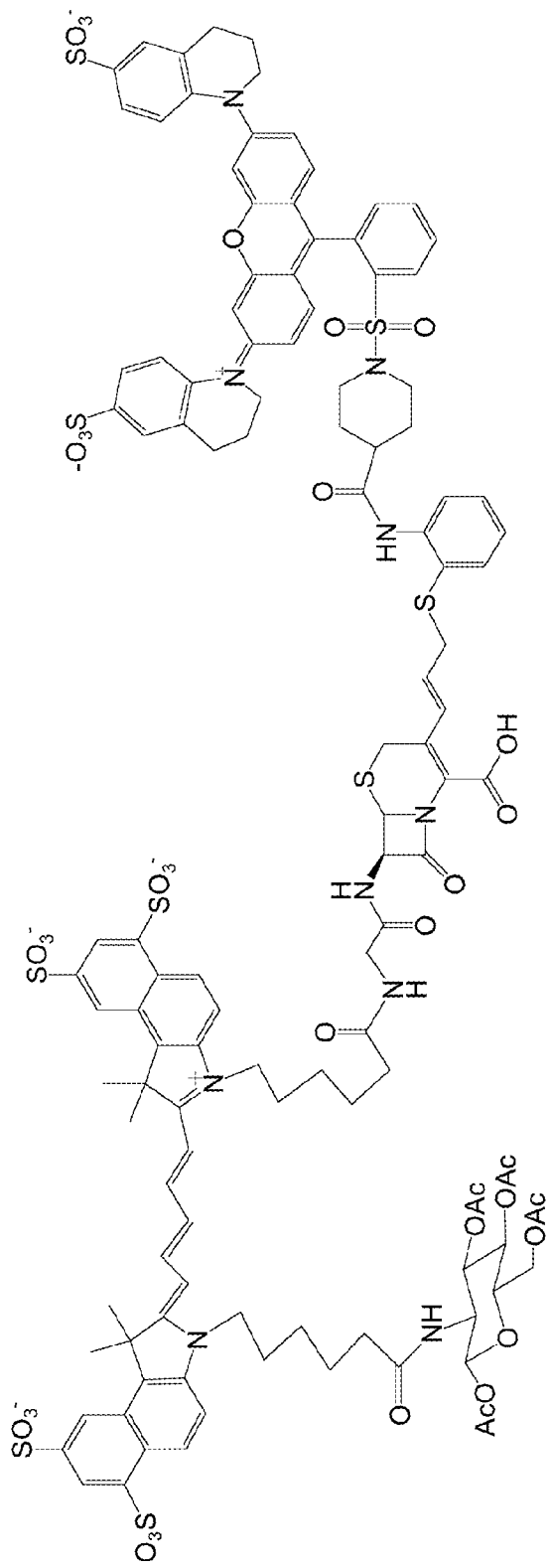
FIGS. 6A-6D depict the structure of CNIR7 (FIG. 6A) and its chemical synthesis (FIGS. 6B-6D).
Figure 6B:
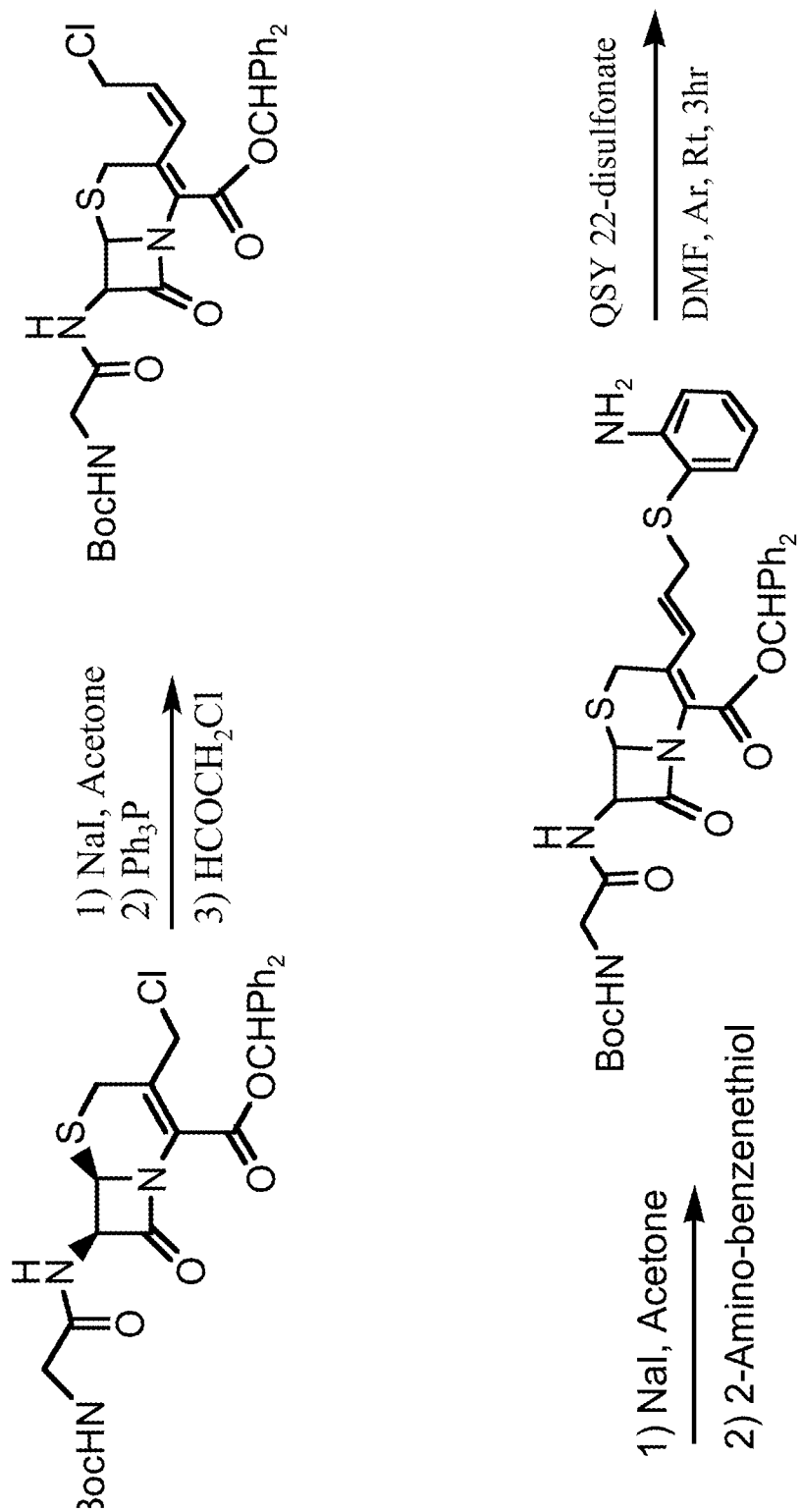
Figure 6C:
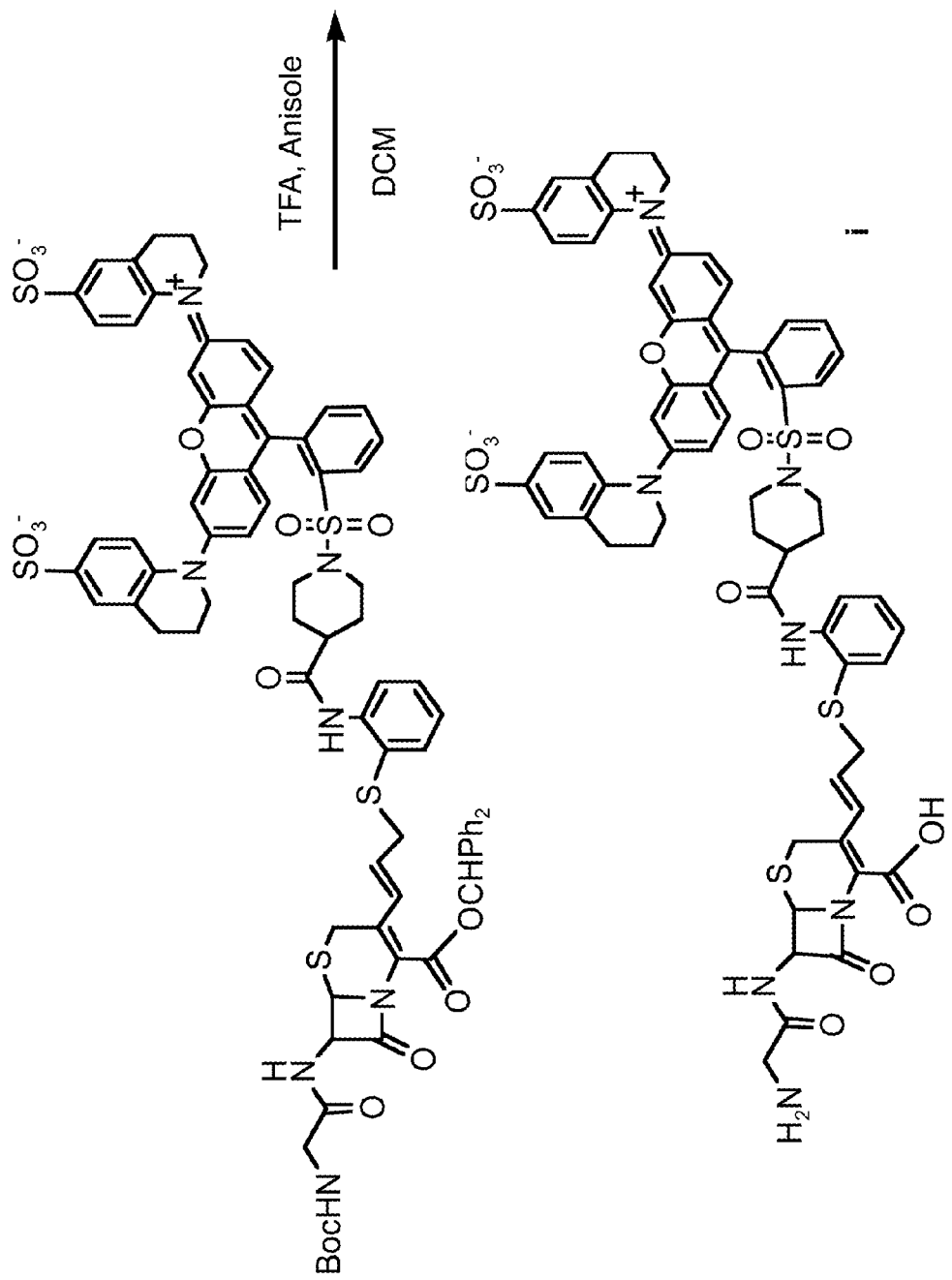
Figure 6D:
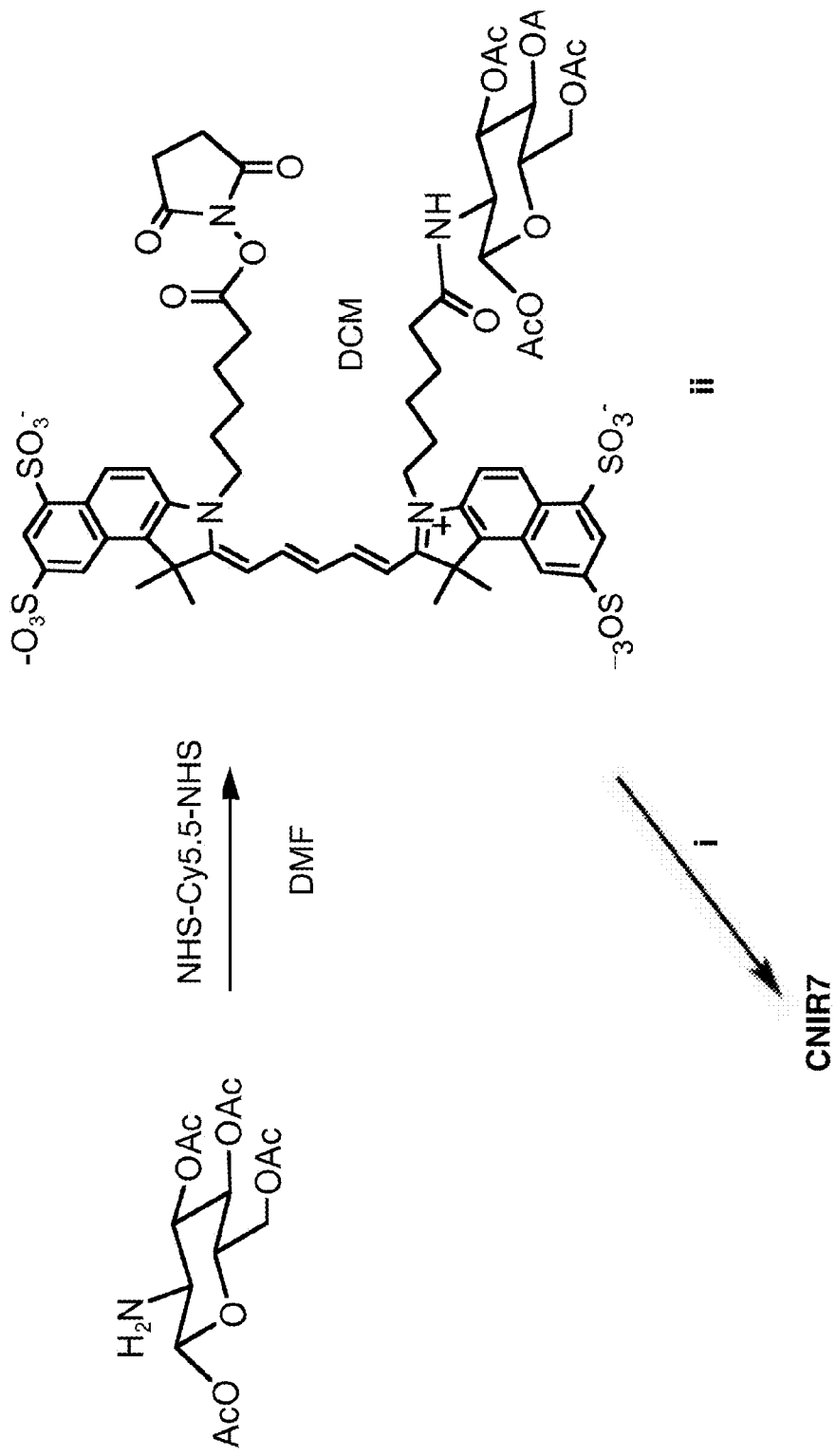

To image Bla expression in living animals with whole body fluorescence imaging, a near-infrared/infrared fluorogenic substrate is beneficial because infrared/near-infrared light has better tissue penetration and less light scattering than visible light and is much less absorbed by the hemoglobin (13). Compounds CNIR1, CNIR2, CNIR3, CNIR4, CNIR5, CNIR9, and CNIR10 are a series of near-infrared fluorogenic substrates for imaging Bla expression in cultured cells (FIGS. 3, 6A-6B). These compounds are useful as a framework for building a cell-permeable near-infrared fluorogenic substrate for Bla and can be used to examine the effects of charge on availability of the probe to the bacteria intracellularly or in animals.

Reporting Bla activity is based on fluorescence resonance energy transfer (FRET). The probes contain a FRET donor and a FRET quencher. In order for in vivo imaging, the fluorophore should ideally have an emission at more than 650 nm and low toxicity. Indocyanine dyes (Cy5, Cy5.5, and Cy7) have emission from 650 to 800 nm, and have been used in tens of thousands of patients with little reported side effects. Therefore, Cy5 is chosen as the FRET donor. It has been demonstrated that a quenching group, QSY21, not fluorescent itself with a wide absorption spectrum from 540 to 730 nm peaking at 660 nm, is an effective quencher for the emission of Cy5.

CNIR1, is essentially non-fluorescent, but produces a highly fluorescent product with 57-fold increase in the emission intensity at the wavelength of 660 nm upon treatment with Bla (14). However, CNIR1 itself is not cell-permeable and thus not able to image Bla in vivo. To improve membrane permeability of CNIR1, CNIR1 was conjugated with peracetylated D-glucosamine, CNIR3, has good cell-permeability and is able to image Bla expression in single living cells. Adding two sulfonate groups on QSY21 to improve the solubility yields CNIR4.

CNIR5 and CNIR6

Figure 4A:
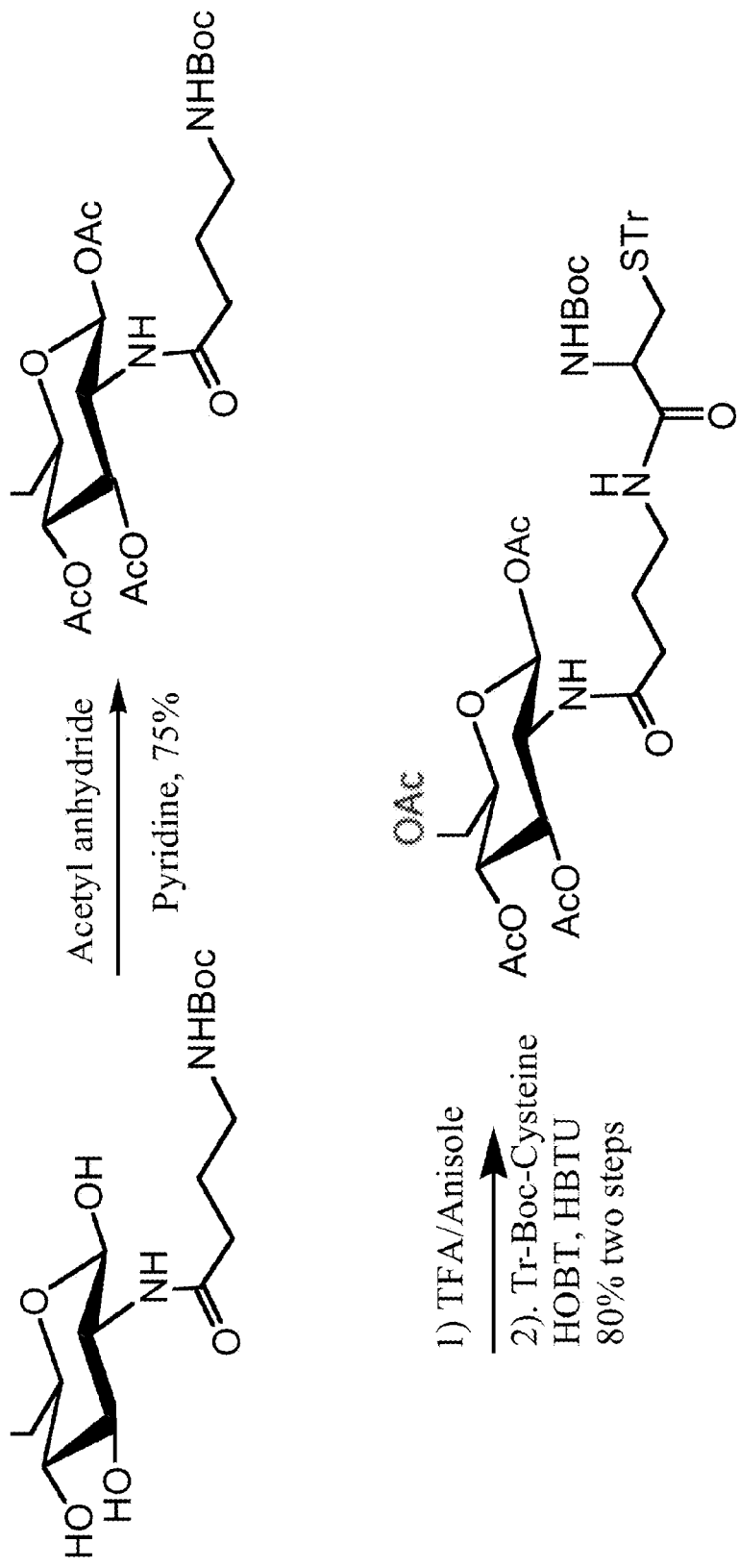
FIGS. 4A-4G depict a synthetic scheme for preparing near-infrared substrate CNIR5 (FIGS. 4A-4C), an alternative synthetic scheme for large-scale, commercial preparation of CNIR5 (FIGS. 4D-4E), the fluorescent intensity vs wavelength of CNIR5 in the presence and absence of beta-lactamase (FIG. 4F) and the structure of CNIR5-QSY22 (FIG. 4G).
Figure 4B:
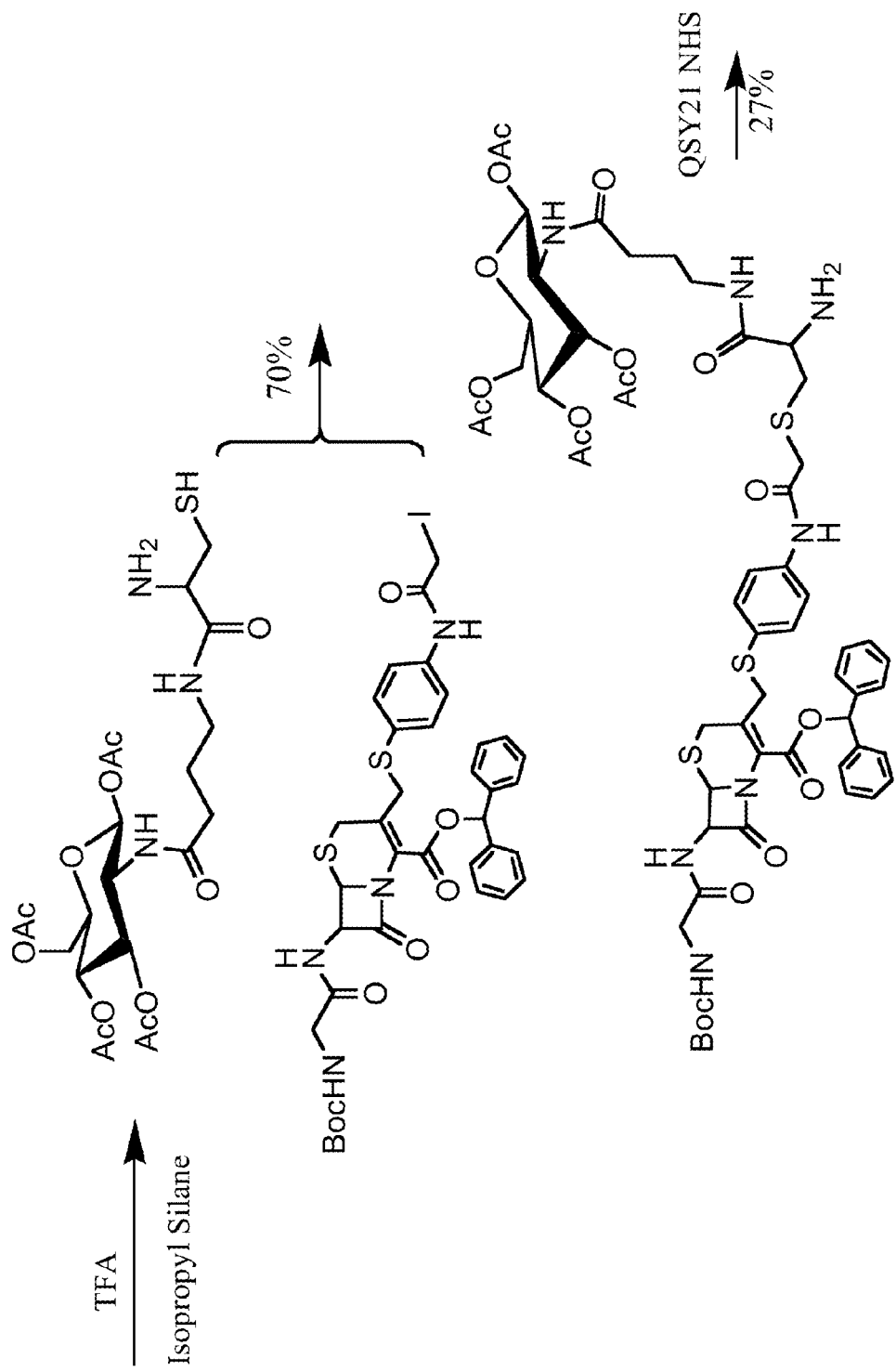
Figure 4C:
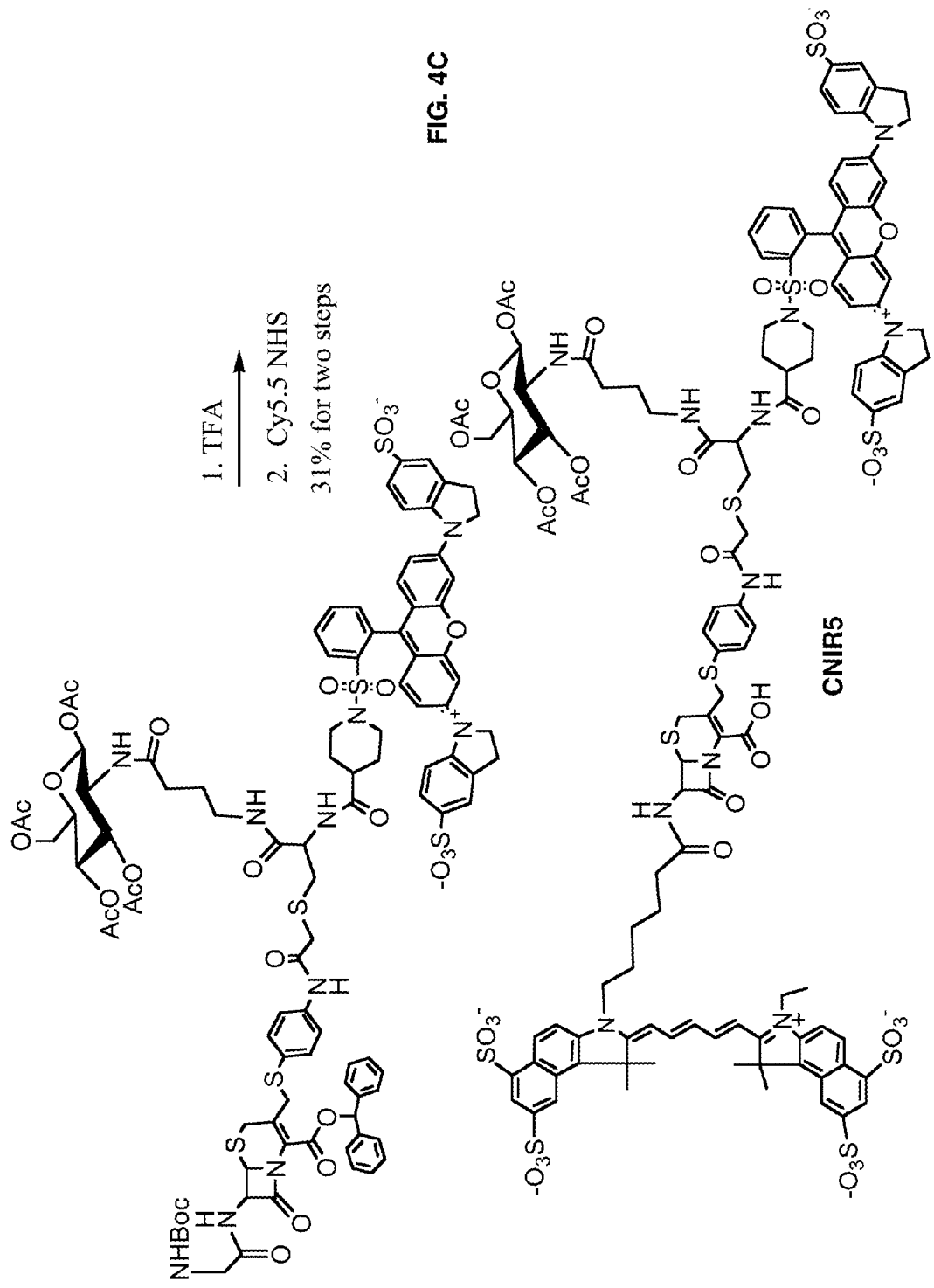
Figure 4D:
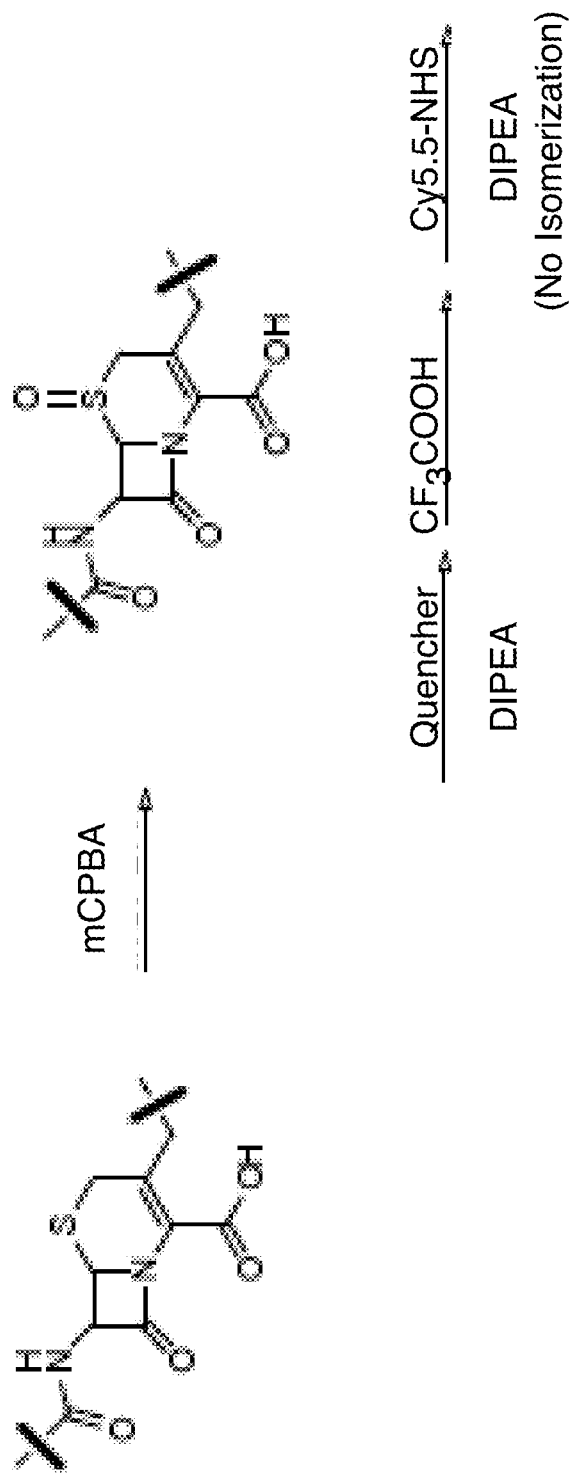
Figure 4E:
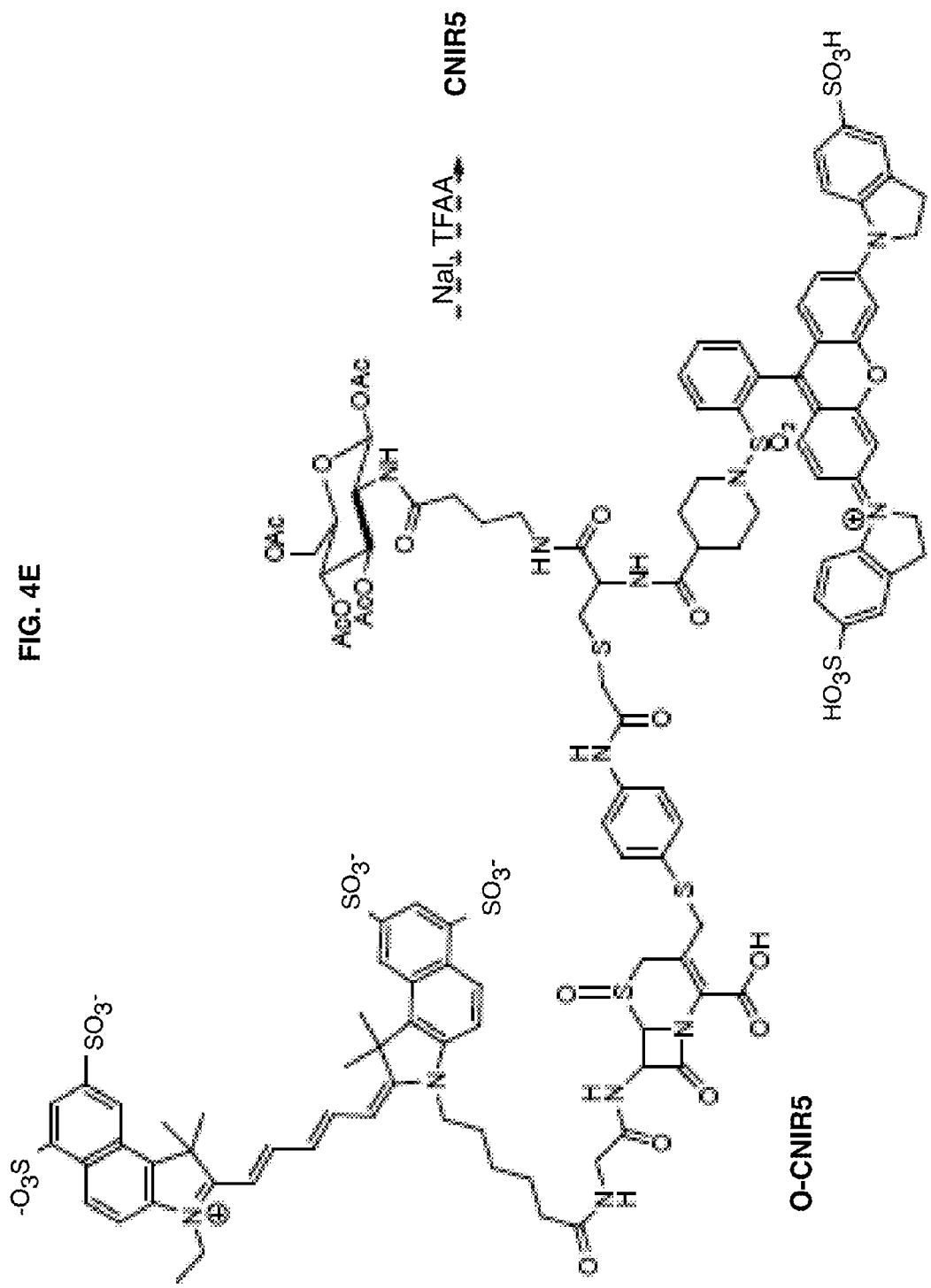
Figure 4F:
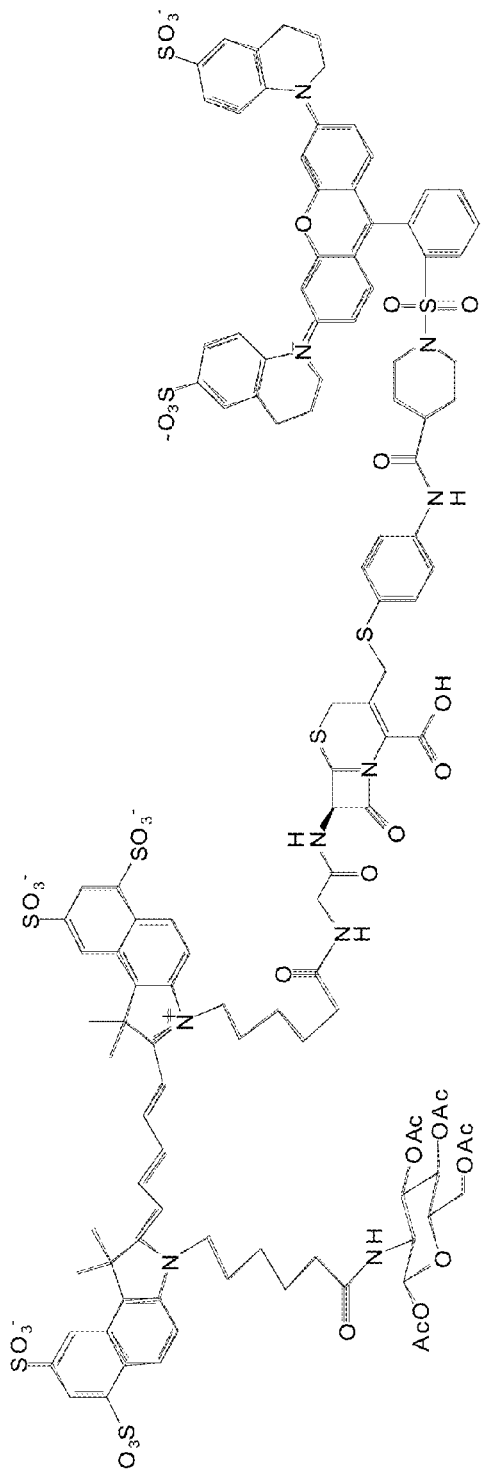
Figure 4G:
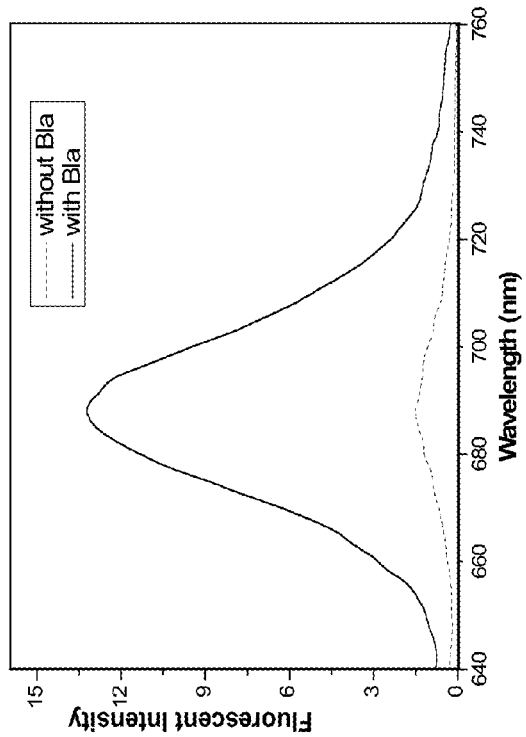

CNIR1 to CNIR4 are all based on Cy5. For in vivo animal imaging, Cy5.5 is more preferred because of its longer emission wavelength. Thus, Cy5 was replaced with Cy5.5 and CNIR5 was synthesized (FIGS. 4A-4C). The final product was purified by HPLC and characterized by mass spectrometer (calculated mass for $C_{122}H_{123}N_{11}O_{39}S_{10}$: 2687.98; MALDI-MS observed $[M+H]^+$: 2687.68). CNIR5 itself emits weak fluorescence at 690 nm when excited, but upon the treatment of Bla, the intensity increases by more than 9-fold (FIG. 4D). Its hydrolysis kinetics by Bla were measured in phosphate buffered saline (PBS) at pH 7.1: the catalytic constant $k_{cat}$=0.62±0.2 $s^{-1}$, and Michaelis constant $K_m$=4.6±1.2 µM (the values were obtained from weighted least-square fit of a double reciprocal plot of the hydrolysis rate versus the substrate concentration). Its catalytic efficiency ($k_{cat}/k_m$) was 1.36×10$^5$ $M^{-1}s^{-1}$. CNIR5 was very stable in the PBS with a spontaneous hydrolysis rate of 1.75×10$^{-7}$ $s^{-1}$, as well in mouse serum, i.e., little fluorescence increase was observed even after 12 hours incubation. Also CNIR5 may be synthesized by replacing QSY21 with QSY22 (FIGS. 4D-4E). This synthesis is very similar to that of CNIR5 and is not problematic. The synthesis of QSY22 is discussed below. CNIR6 is an analog of CNIR5 without the peracetylated D-glucosamine and is useful as a control.

CNIR5 also may be synthesized for large-scale, commercial use. The synthetic scheme depicted in FIG. 4A is not suitable for large-scale synthesis primarily because of the instability of the probe under basic conditions. N,N-diisopropyl ethylamine (DIPEA), an organic base that is necessary for the conjugation of both quencher and near-infrared cye Cy5.5 to the lactam, generally accelerates the migration of the carbon-carbon double bond on the beta-lactam ring which results in an isomer of CNIR5. This significantly increases the difficulty of the purification process. To avoid isomerization oxidizing the sulfide on the 6-membered ring of the lactam compound to sulfoxide at an early stage and reducing it back to sulfide at the late stage of the synthesis (FIG. 4C). No isomerization is detected during oxidation of the sulfide and conjugation of the quencher and the dye.

CNIR7

CNIR7 is a modification of CNIR5 that improves its sensitivity for in vivo imaging of Bla. The quenching group QSY21 disulfonate used in CNIR5 has a maximal absorption at 675 nm, but Cy5.5 emits maximally at 690 nm. Therefore, as with CNIR5, the quenching efficiency is just 90%, which contributes largely to the observed background fluorescence. In the FRET pair of QSY21 and Cy5 (CNIR1), because of better spectral overlap between QSY21 and Cy5, the quenching efficiency was more than 98%. Thus, a quenching group that can absorb at 690 nm would quench Cy5.5 better and decrease the background signal. It has been reported that for QSY21, when the indoline was replaced by a tetrahydroquinoline, the absorption maximum red-shifts by 14 nm.

Thus, a new structure QSY22 disulfonate (FIGS. 5A-5D) was synthesized by replacing the indoline groups in QSY21 with tetrahydroquinolines, which should similarly red-shift by 14 nm in the maximal absorption. Since the only structural difference between the two is that QSY22 uses tetrahydroquinoline which contains a six-member fused ring and the QSY21 uses a five-member indoline, the sulfonation chemistry is used and the same sulfonation position (para) on the benzene ring would be expected. QSY22 disulfonate, therefore, should quench Cy5.5 more efficiently and lead to a lower background signal.

Secondly, the value of $k_{cat}$ for CNIR5 is about 0.6 $s^{-1}$, which is much smaller than CC1 and CCF2. A double bond inserted between the quencher and Cy5.5, which should lead to an increase in $k_{cat}$ as well. Thirdly, the distance between the FRET donor, Cy5.5, and the quencher, QSY22 disulfonate, is decreased to improve the energy transfer efficiency. CNIR5, has a long linker group containing cysteine for the incorporation of the transporter. In the new CNIR7, the transporter is linked to the other coupling site on Cy5.5, therefore, there is no longer a need to include a long linker. Furthermore, a 2-amino thiophenol replaces the 4-amino thiophenol in CNIR5, and should further shorten the distance between Cy5.5 and the quencher. The final design of the NIR substrate, CNIR7, and its chemical synthesis are shown in FIGS. 6A-6D. Its synthesis can be completed in an even shorter route and should be easier than CNIR5.

CNIR7 also may comprise a short cationic peptide, such as a TAT sequence to replace the acetylated D-glucosamine. D-amino acids are used instead of L-amino acids to avoid peptidase hydrolysis. It has been demonstrated that short cationic peptides such as the third helix of the homeodomain of Antennapedia (15-16), HIV-1 Rev protein and HTLV-1 Rex protein basic domains, and HIV-1 Tat protein basic domains are capable of permeating the plasma membrane of cells.

CNIR9 and CNIR10

Figure 5C:
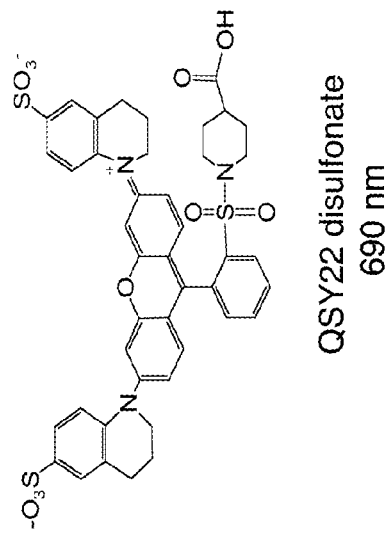
FIGS. 5A-5D depict the structures of QSY 21 (FIG. 5A), QSY21 disulfonate (FIG. 5B) and QSY22 disulfonate (FIG. 5C) and the chemical synthesis of QSY22 disulfonate (FIG. 5D).
Figure 5B:
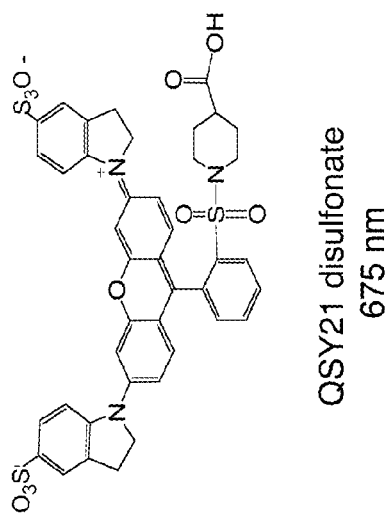
Figure 5A:
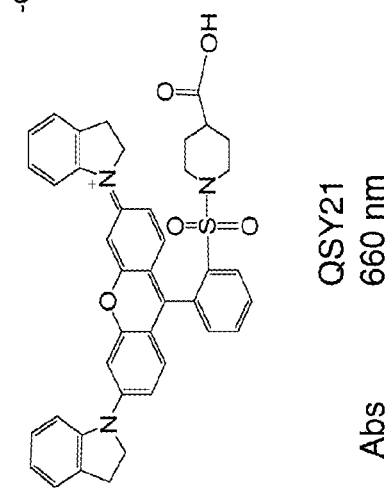
Figure 5D:
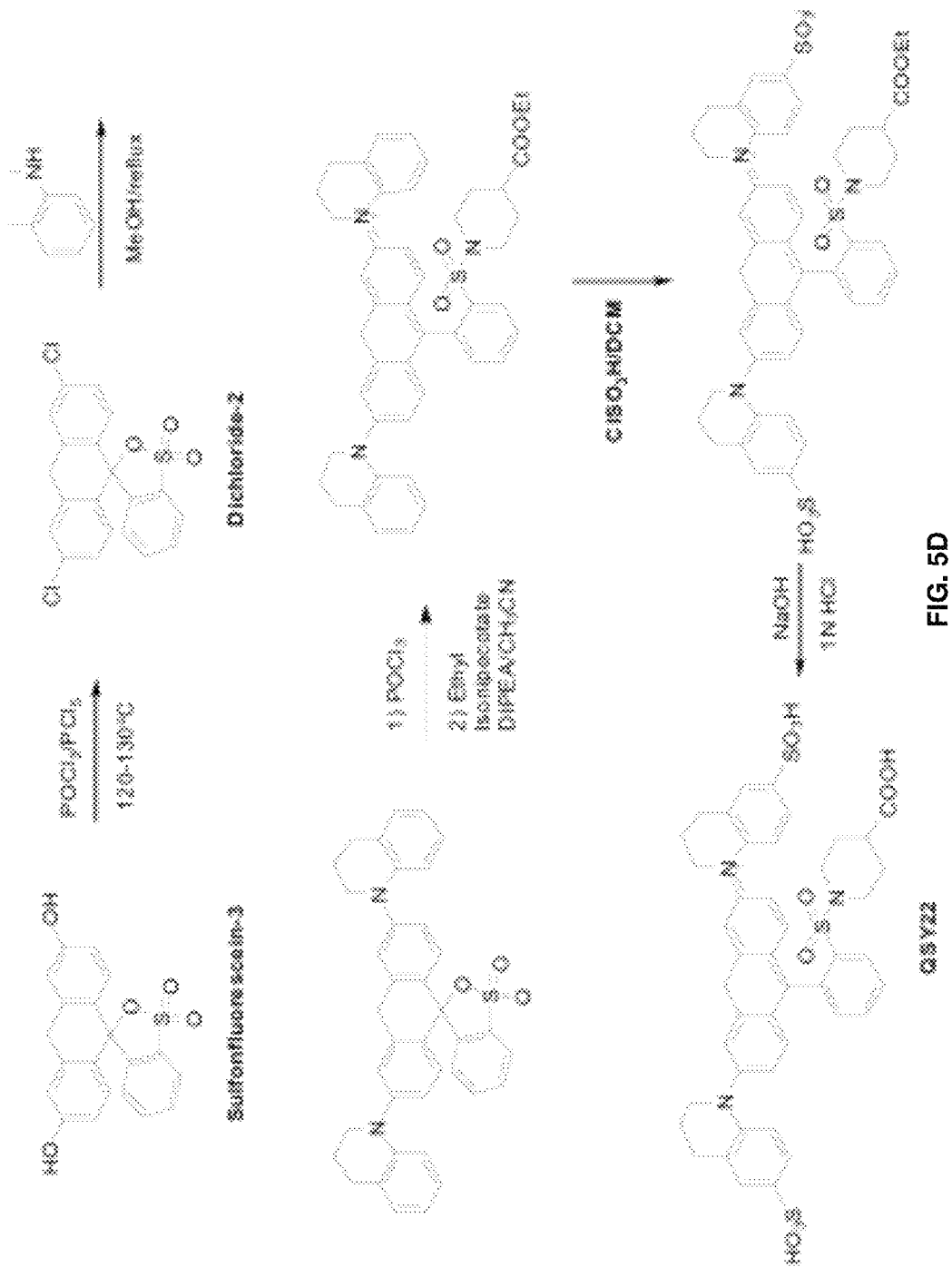
Figure 7A:
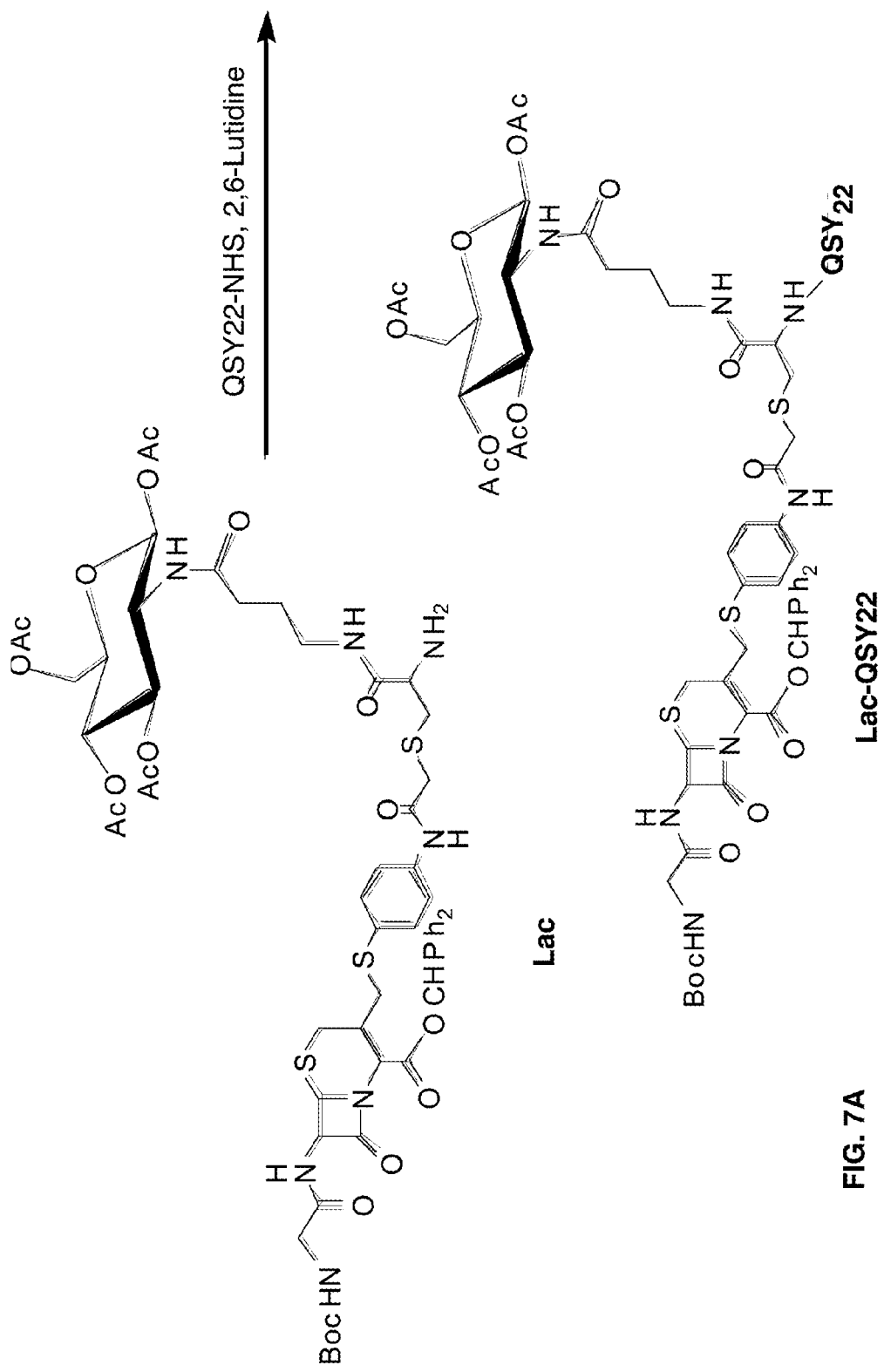
FIGS. 7A-7E depict the synthetic schema for CNIR9 (FIGS. 7A-7B) and CNIR10 (FIGS. 7C-7E).
Figure 7B:
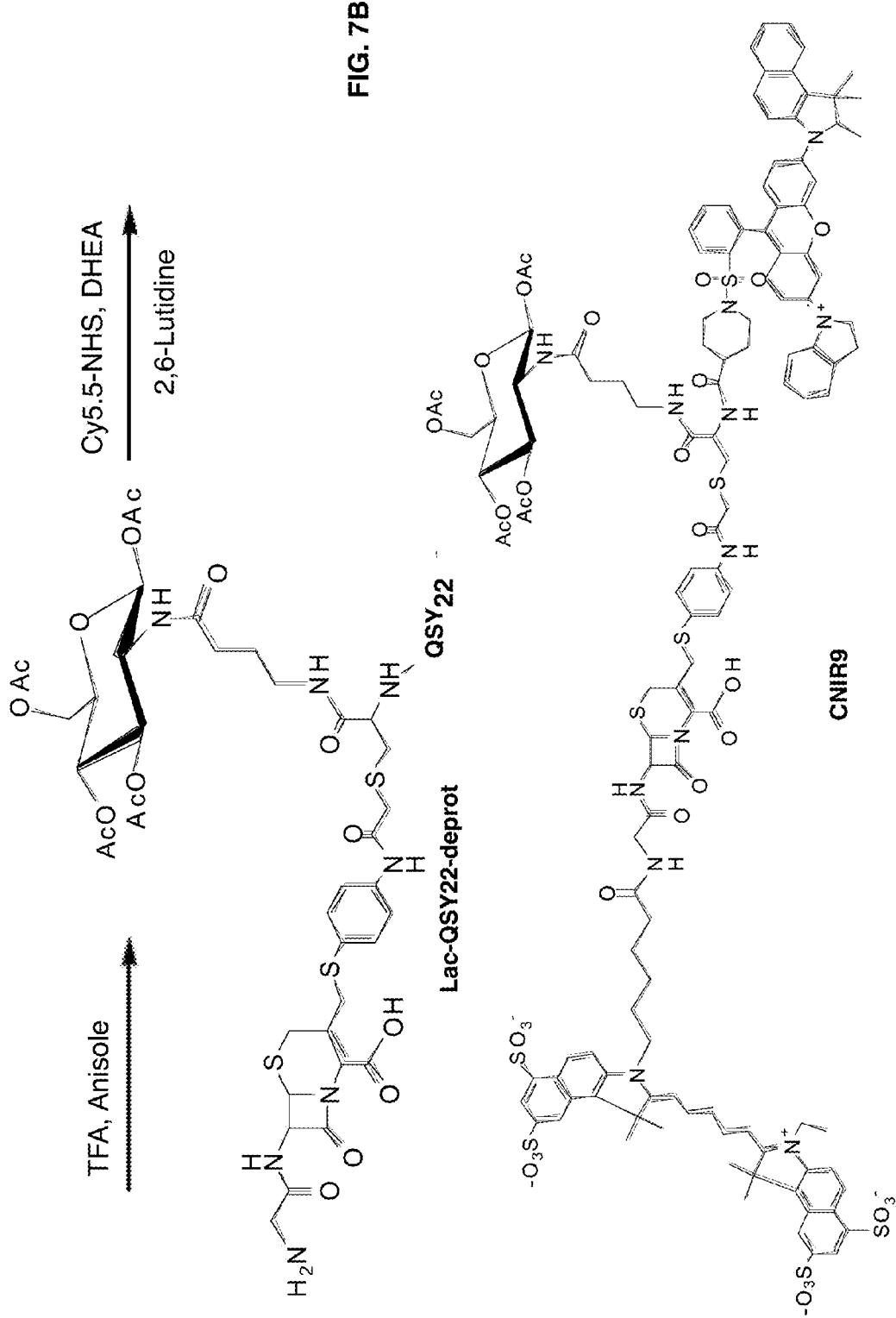
Figure 7C:
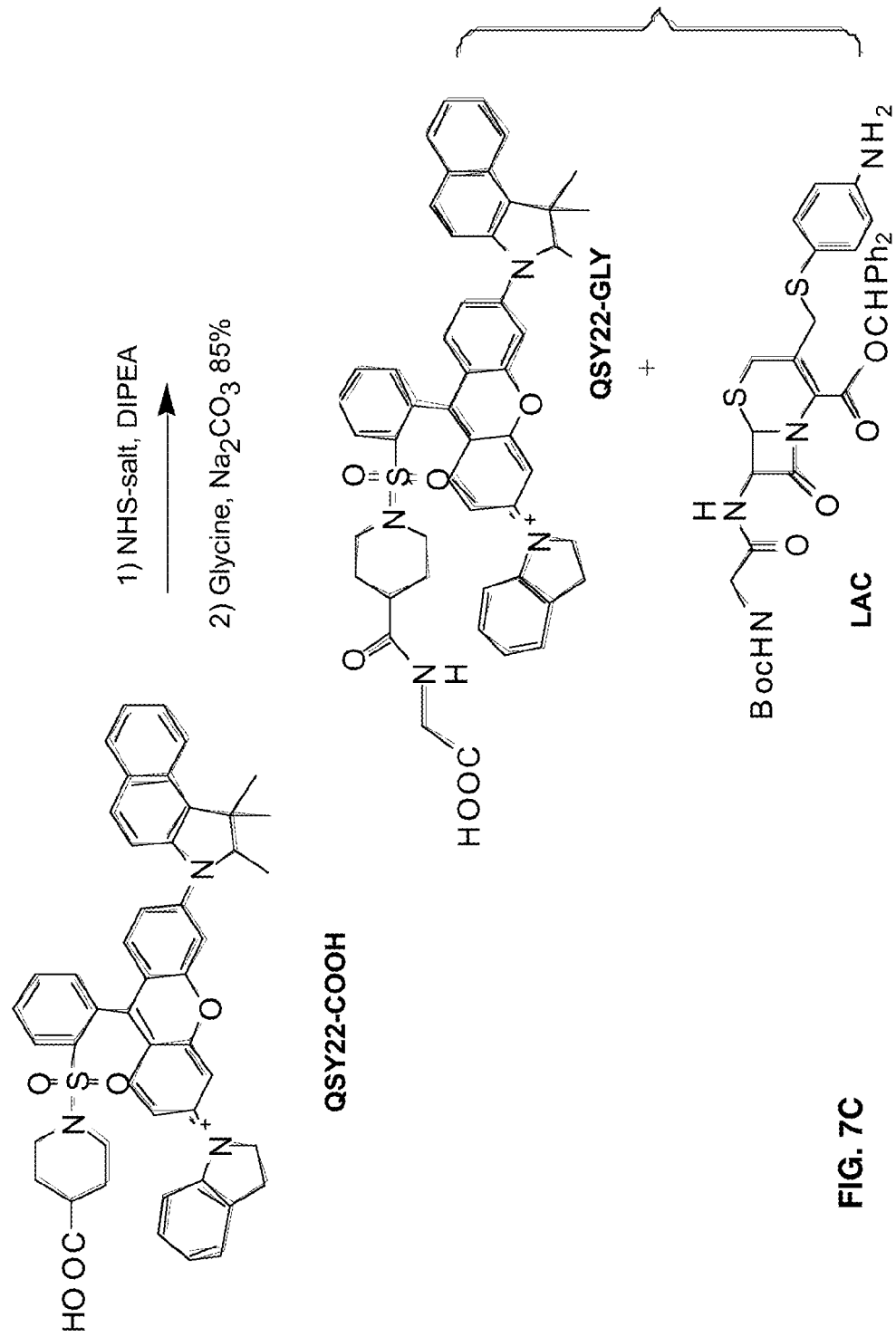
Figure 7D:
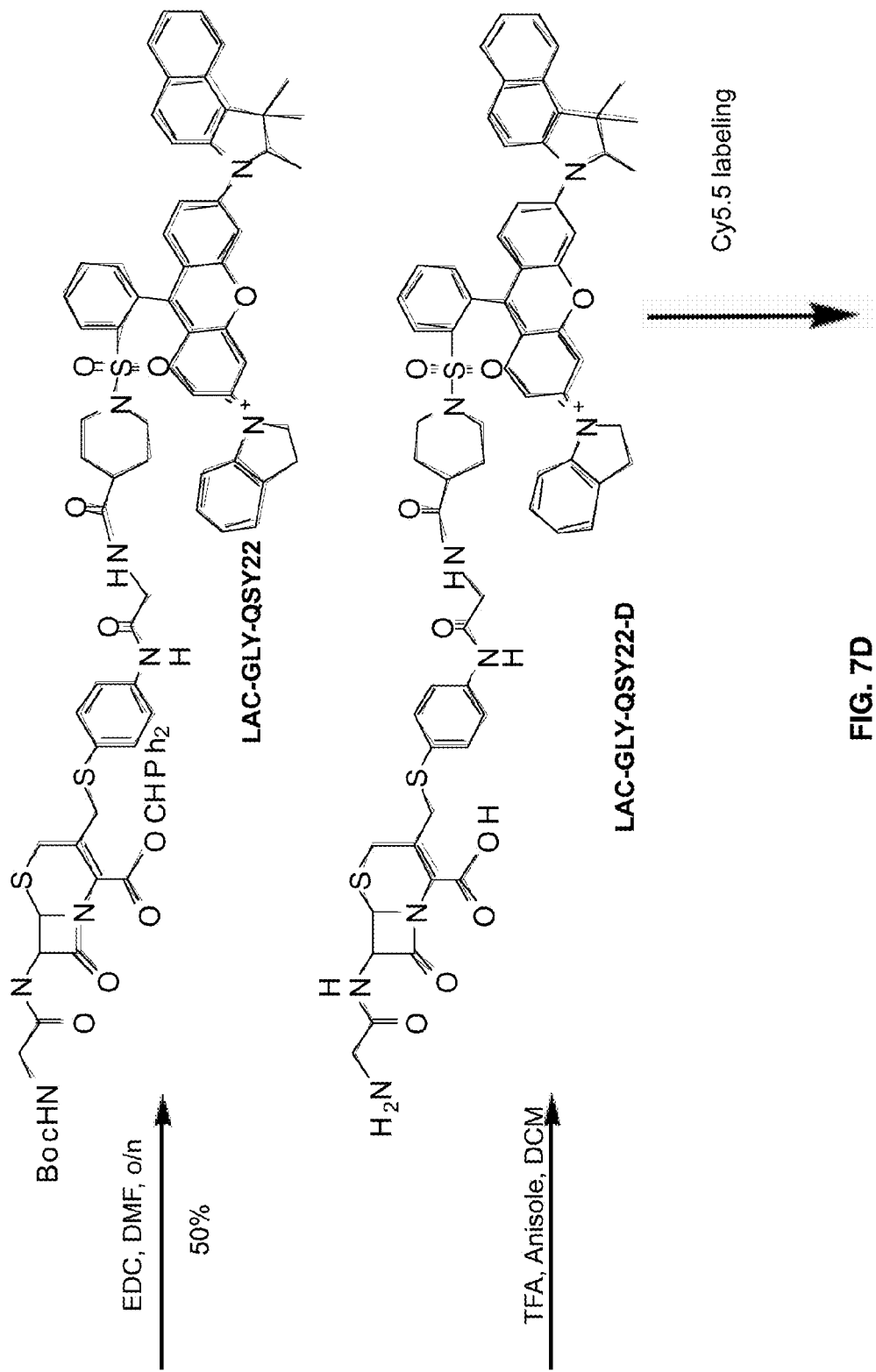
Figure 7E:
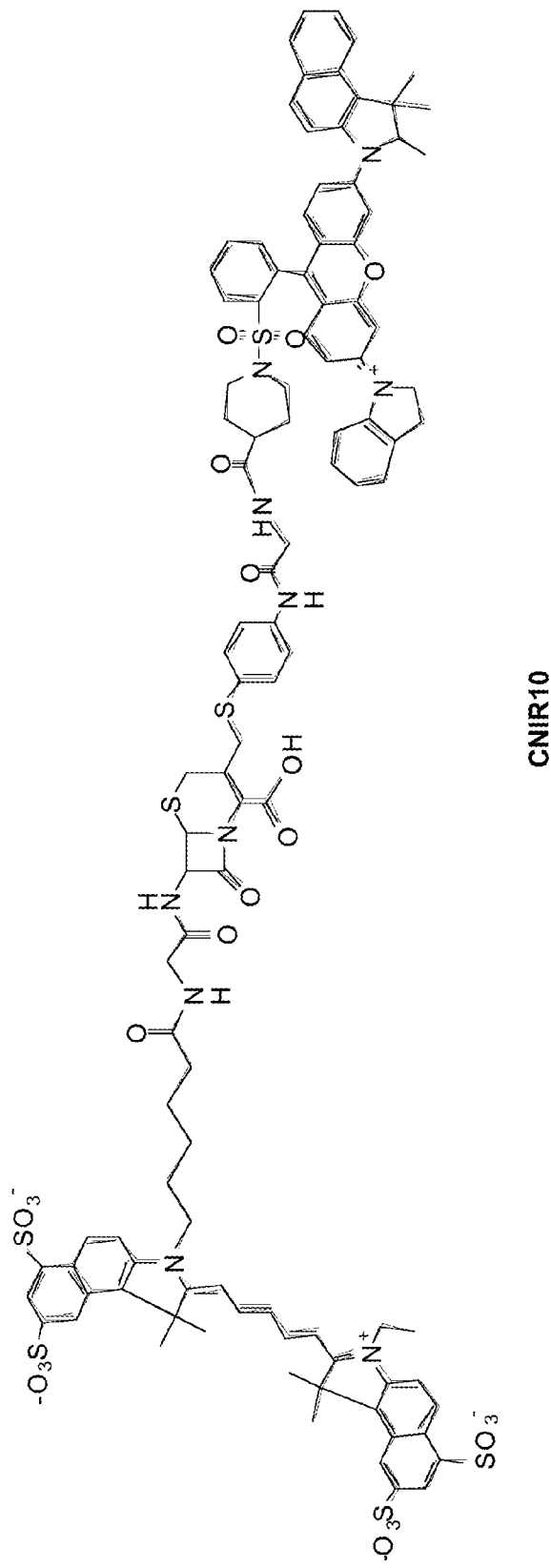

The quencher QSY22 synthesized in FIG. 5D is attached to the lactam ring to produced CNIR9 as depicted in the synthetic scheme shown in FIGS. 7A-7B. CNIR9 displays very high fluorescence upon cleavage, but very low fluorescence in the absence of cleavage by Bla. The similar compound, CNIR10, was synthesized with a shorter bridging group and fewer sulfates, as depicted in the synthetic scheme shown in FIGS. 7C-7E.

CNIR800 and Derivatives

CNIR800, was designed with a new fluorophore, IRDye800, that fluoresces at a longer wavelength, 800 nm, to improve the sensitivity of REF imaging. The longer wavelength of CNIR800 penetrates tissue better than the Cy5.5 fluorophore of CNIR5 and reduces background due to autofluorescence, since in most tissue autofluorescence is at wavelengths below 700 nm. CNIR800 displays very low background fluorescence and a large differential (25-fold) after cleavage with BlaC. CNIR800.2 (FIG. 11C) is the CNIR800 probe with a different linker synthesized by the alternative method described in Example 5, as is CNIR800-3 (FIG. 11D), a CNIR800 derivative with a methoxy substitution to the R2 position on the lactam ring. In addition, CNIR800 derivatives may comprise a methyl substitution to the R2 position or a benzyl group attached to the 7-amine on the R1 position.

CDC 1-5 Substrates

Because Mtb BlaC has a larger active site than TEM-1 Bla, it is reasonable that a bigger substituted group on the lactam ring might help to improve the specificity of a fluorescence substrate for Mtb BlaC over TEM-1 Bla. The effect of the substituted group on the amine of the lactam ring was evaluated first. To simplify the synthesis and speed up the screening process, a fluorescent substrate comprising an amine-substituted lactam ring that releases 7-hydroxycoumarin as the fluorophore. Upon the treatment of TEM-1 Bla or Mtb BlaC, 7-hydroxycoumarin is released and fluorescence signal is generated. Therefore, by simply monitoring the fluorescence intensity of the substrate upon release of the fluorophore, the hydrolysis kinetics of TEM-1 Bla and Mtb BlaC can be obtained (Table 1).

As depicted in FIGS. 8A-8C, fluorogenic probes CDC-1 and CDC-2 are synthesized, where CDC-2 is the sulfoxide counterpart of CDC-1. Similarly, probes CDC-3 and CDC-4, which have a larger substituted group attached to the amine group of the lactam ring, were also prepared. It has shown that probe CDC-1 is a TEM-1 Bla-preferred probe, giving much faster hydrolysis kinetics than Mtb BlaC. It was contemplated that CDC-3, with a bigger substituted group, could improve the specificity to Mtb BlaC.

The hydrolysis kinetics of the probes was determined with a fluorometer by measuring the fluorescence intensity at different time points in the presence of TEM-1 Bla and Mtb BlaC, respectively. Surprisingly, as shown in FIG. 8D, substrate CDC-3 displayed even faster hydrolysis kinetics than CDC-1, a TEM-1 Bla-preferred substrate, in the presence of 2 nM of TEM-1 Bla. These four probes are all obvious TEM-1-preferred since the fluorescence intensity is much lower after treatment with Mt Bla for same amount of time at the same enzyme concentration (2 nM in PBS). The fluorescence intensity enhancement in the presence of 2 nM of Mtb BlaC is so low that it is even difficult for an accurate measurement. Then 10 nM of Mtb BlaC was used for the determination of hydrolysis kinetics of Mtb BlaC (FIG. 8E). Unfortunately, small probe CDC-1 gave even faster hydrolysis kinetics with Mtb BlaC than the larger size probe CDC-3, indicating the size of the substituted group on the amine is not as critical for the BlaC specificity. The sulfoxide probes CDC-2 and CDC-4 all showed a much slower hydrolysis kinetics with both TEM-1 Bla and Mtb BlaC than their sulfide counterparts CDC-1 and CDC-3, respectively, without any significant improvement in the specificity.

The effect of a group substituted directly onto the lactam ring of the probe was investigated. As depicted in FIG. 8F, substrate CDC-5 having a methoxy group on the 7-position of the lactam ring was synthesized. The hydrolysis kinetics of CDC-5 were measured with a similar assay as above and CDC-1 was used as the control. CDC-5, unlike CDC-1 (FIG. 8G), clearly shows a high Mtb BlaC-preference (FIG. 8H). The fluorescence intensity of probe CDC-5 is only increased slightly after treated with 20 nM of TEM-1 Bla in PBS for 15 min, while over 30 folds of fluorescence increase can be detected with the same concentration of Mtb BlaC, indicating a profound substituted effect on the lactam ring. The fluorescence intensity of CDC-5 treated with Mtb BlaC for 15 min is over 10-times stronger than that with TEM-1 Bla. CDC-5 has proven to be the first Mtb BlaC-preferred fluorogenic probe observed. Such a substituted structure can be easily adapted in the CNIR5-like or CNIR800 or CNIR800-like, near-infrared probe synthesis.

TABLE 1

Kinetic parameters of coumarin-based lactam probes.

| Name | Structure | blaC | | | TEM-1 bla | | |
|---|---|---|---|---|---|---|---|
| | | $K_m$ (mM) | $k_{cat}$ (s$^{-1}$) | $k_{cat}/K_m$ (s$^{-1}$M$^{-1}$) | $K_m$ (mM) | $k_{cat}$ (s$^{-1}$) | $k_{cat}/K_m$ (s$^{-1}$M$^{-1}$) |
| CDC-1 | [structure] | 63 | 13 | 2.1 × 10$^5$ | 135 | 48 | 3.6 × 10$^5$ |
| CDC-3 | [structure] | 69 | 6 | 8.7 × 10$^4$ | 59 | 77 | 1.3 × 10$^6$ |

TABLE 1-continued

Kinetic parameters of coumarin-based lactam probes.

| Name | Structure | blaC $K_m$ (mM) | blaC $k_{cat}$ (s$^{-1}$) | blaC $k_{cat}/K_m$ (s$^{-1}$M$^{-1}$) | TEM-1 bla $K_m$ (mM) | TEM-1 bla $k_{cat}$ (s$^{-1}$) | TEM-1 bla $k_{cat}/K_m$ (s$^{-1}$M$^{-1}$) |
|---|---|---|---|---|---|---|---|
| CDC-OMe | [structure] | 47 | 1 | $2.1 \times 10^4$ | 50 | $7.6 \times 10^{-4}$ | 15.2 |
| CDC-OEt | [structure] | 131 | $2.6 \times 10^{-2}$ | $1.9 \times 10^2$ | ND | ND | ND |
| CC1 | [structure] | 37 | 6 | $1.6 \times 10^5$ | 60 | 137 | $2.3 \times 10^6$ |
| 4-65 | [structure] | 148 | 10 | $6.8 \times 10^4$ | 133 | 10 | $7.5 \times 10^4$ |
| 4-64 | [structure] | 139 | 0.52 | $3.7 \times 10^3$ | ND | ND | ND |
| CDC-2 | [structure] | 136 | 0.51 | $3.8 \times 10^3$ | 454 | 7 | $1.5 \times 10^4$ |

In general, Table 1 demonstrates that the lactam substrates display better hydrolysis kinetics toward TEM-1 Bla than BlaC; however, this trend is reversed when a methoxy or ethoxy group is introduced to the 7-position carbon (R2 in new FIG. 5) of the lactam ring. For example, the value of $k_{cat}/K_m$ of the probe CDC-OMe for blaC is 1,400 fold larger than that for TEM-1 bla. The hydrolysis of CDC-OEt and 4-64 by TEM-1 bla is so slow that cannot be determined. The substitution of proton by a slightly larger group has profound effect on the selectivity for BlaC over TEM-1 Bla. The sulfide oxidation significantly decreases the kinetic efficiency for both TEM-1 Bla and BlaC. The methoxy group is more preferred to a larger ethoxy group since ethoxy substitution led to much decreased kinetics compared to methoxy substitution. TEM-1 Bla appears a large substitution on R1, as the value of $k_{cat}/K_m$ decreases (CDC-3>CDC-1>4-65) as the size of R1 decreases. However, CDC-1 displays the largest value of $k_{cat}/K_m$ for BlaC.

Other Substrates

XHX2-81, XHX2-91, XHX3-1, XHX3-2, XHX3-26, and XHX3-32 are derivatives or analogs of CNIR800 substrates that display selectivity for mycobacterial BlaC over TEM-1

(FIGS. 9A-9E). Compound XHX3-32 is similar in structure to CDC-5 and demonstrates a threshold of detection below 100 bacteria and may be as low as 10 bacteria (FIG. 9F). XHX3-1 comprises the IRDye800 fluorophore and IRDyeQC-1 quencher attached to the lactam backbone which are used to synthesize CNIR800 which confers more rapid tissue distribution and more sensitive detection of Mtb in mice. This does not, however, preclude using a Cy5.5-based fluorophore systems for detection. XHX3-2 has an improved leaving group and the incorporation of a double bond to increase the release kinetics of the phenolic group. It is contemplated that the configuration at the double bond is trans, instead of the previous cis configuration, because of the much larger allylic group.

Caged Bla Substrate for Imaging Bla in Tuberculosis

The structure of the caged substrate for Bla (Bluco) (FIG. 10A), comprises D-luciferin, the substrate of firefly luciferase (Fluc), and beta-lactam, the substrate of Bla. The phenolic group of D-luciferin is critical to its oxidation by Fluc. When this phenolic group is directly coupled to the 3' position of the cephalosporin via an ether bond, the resulting conjugate should become a poor substrate for Fluc, but remain a substrate for Bla. The opening of the beta-lactam ring by Bla would trigger spontaneous fragmentation, leading to the cleavage of the ether bond at the 3' position and releasing free D-luciferin that can now be oxidized by Fluc in a light-producing reaction. To improve the stability of the conjugate, the sulfide on the cephalosporin was oxidized to sulfoxide, affording the final structure Bluco. The preparation of Bluco is accomplished via a multiple-step organic synthesis, (FIG. 10B). Since the size of Bluco is much smaller than a CNIR series probe, it may penetrate the *M. tuberculosis* cell wall better. The identified substitution at the 7 amino position can be simply utilized here to design a TB-specific caged luminescent substrate for SREL imaging of Bla in TB. Bluco also may be synthesized to have an improved $K_{cat}$ by insertion of a double bond (Bluco2) and with use of a carbamate linkage (Bluco3).

EXAMPLE 5

Alternative Synthesis of CNIR Fluorogenic Substrates

In an alternative synthetic scheme, CNIR probes can be synthesized utilizing a module based approach (FIG. 11A). Unit 1 and unit 2 can be prepared using previous chemistry at a large quantity. Instead of using base-catalyzed coupling, mild chemo-ligation is implemented between a free cysteine and the thiol ester introduced to the lactam unit 2. Under this condition, no isomerization is expected. The product 3 can be isolated in a high purity at a large quantity. The free amino group on 3 is readily conjugated to the NIR dye, such as Cy5.5 and NIR800. through the standard NHS ester mediated coupling, and the thiol group is conjugated via the maleimide group on the quencher. Since both couplings are orthogonal, they may be performed in a one-pot synthesis, and the final product is purified by HPLC. The use of organic bases such as N,N-diisopropyl ethylamine (DIPEA), which is the main source of isomerization, has been eliminated. In addition, no deprotection chemistry is required after the quencher is introduced, which improves the yield since the quencher QC-1 has been observed with decomposition in the trifluoroacetic acid mediated deprotection condition. Importantly, just one final HPLC purification is required.

In another alternative synthetic scheme (FIG. 11B), precursor 1.1 is the intermediate for synthesis of CNIR5. The free amino group on intermediate 1.1 can similarly react with the NIR dye, such as Cy5.5 and NIR800, and quencher in PBS. Since the use of organic bases, such as N,N-diisopropyl ethylamine (DIPEA), the main source of isomerization, is avoided, the reaction is clean without the need for HPLC. Deprotection of the protecting groups on the lactam is performed, and the amino group on the 7-position is coupled to the NIR dye, for example, CY5.5 or NIR 800, in PBS. The final reaction product is subject to HPLC purification. In comparison to the scheme shown in FIG. 11A, no organic base is used in the dye and quencher coupling so isomerization in the final product is not expected. As with the chemical synthetic scheme in FIG. 11A, only one HPLC purification is required thus enabling a large yield of probes.

These chemical synthetic schema can produce CNIR probes, such as CNIR5.2 and CNIR800.2 (FIG. 11C). Although CNIR800.2 and CNIR5.2 (FIG. 11D) have slightly different linking groups to the quencher, it is not contemplated that probe properties would be altered. CNIR800 derivative or analog probes, such as, but not limited too, CNIR800-3, XHX3-1 and XHX3-2 (FIG. 11E), also may be synthesized on a large scale using this chemistry.

EXAMPLE 6

FRET and Fluorescence Incorporation Kinetics for CNIR4, CNIR5, CNIR9, & CNIR10

FRET In Vitro: Detection of Bla Activity in *E. coli* and *M. tuberculosis* with CNIR5

CNIR5 was detested for its ability to detect Bla activity in living bacteria. *E. coli* was transformed with ampicillin resistant plasmid and grown overnight at 30 C. Cells were collected and washed with LB media twice before the addition of 500 nM CNIR5. Fluorescence spectra were taken at intervals (Ex: 640 nm), and the data were shown in FIG. 12A. At the end of measurement (t=160 min), a solution of purified Bla was added to verify the complete hydrolysis of CNIR5. The result indicates that CNIR5 is able to detect Bla in *E. coli*. In comparison, when the fluorogenic substrate CCF2/AM from Invitrogen Inc. was used under the same conditions, Bla in live *E. coli* in LB media was not detected. FIG. 12B demonstrates that CNIR 5 could detect between 100-1000 Mtb bacteria with a good correlation between bacterial numbers present and fluorescent signal.

FRET Spectra

FIGS. 13A-13D are the FRET emission spectra for each of the probes CNIR4, CNIR5, CNIR9, and CNIR10 before and after cleavage with Bla for 10 min. All four probes display little fluorescence prior to beta-lactamase cleavage and an increase in maximal emission by 8.5- (660 nm, CNIR4), 24- (690 nm, CNIR5), 9.5- (690 nm, CNIR9) and 10-fold (690 nm, CNIR10) after cleavage. As depicted in FIGS. 13E-13H co-incubation of each of these probes with Mtb resulted in direct labeling of the bacteria, with an increase in fluorescence of 2-fold for CNIR4, 3-fold for CNIR5, 1.5-fold for CNIR9 and 2-fold for CNIR10 after 18 h co-incubation.

Kinetics of *E. coli* TEM-1 and *M. tuberculosis* Bla-C with CNIR4 and CNIR5 Substrates Table 2 compares the kinetics of the *E. coli* TEM-1 and *M. tuberculosis* Bla-C beta-lactamase enzymes with CNIR4 and CNIR 5 as substrates (FIGS. 14A-14B).

The kinetics of fluorescence incorporation into *M. tuberculosis* using these CNIR probes was determined Incorporation and distribution of CNIR4 and CNIR5 probes were used as substrates in *M. tuberculosis* alone in media (FIGS. 15A-15H) and in *M. tuberculosis* infected with macrophages (FIGS. 16A-16H).

TABLE 2

|  | TEM-1 CNIR4 | TEM-1 CNIR5 | Bla-C CNIR4 | Bla-C CNIR5 |
|---|---|---|---|---|
| Km (μM) | 2.677950938 | 1.868473092 | 13.3235901 | 5.897114178 |
| Vmax (μM/S) | 0.028860029 | 0.016342807 | 0.00573132 | 0.003584872 |
| Kcat (1/S) | 0.577200577 | 0.326856134 | 0.11462632 | 0.071697437 |

CNIR4 Incorporation into *M. tuberculosis*

Fluorescent confocal microscopy demonstrates that CNIR4 is incorporated intracellularly into *M. tuberculosis* infected macrophages (FIG. 17). DAPI stain (blue) indicates the nuclei of the infected cells, the green fluorescence is from GFP labeled *M. tuberculosis* and the red fluorescence is from cleaved CNIR4. Note that the fluorescence from CNIR4 builds up within the infected cells but uninfected cells display no fluorescence.

Detection of CNIR Probe Fluorescent Signal In Vivo

Mice are infected intradermally with *M. tuberculosis* at various concentrations. The lower left quadrant received $10^8$ bacteria, the upper left quadrant received $10^7$ bacteria and the upper right quadrant received $10^6$ bacteria. Fluorescence is measured in the presence of each of the CNIR4, CNIR5, CNIR9, and CNIR10 probes (FIGS. 18A-18E). CNIR5 showed the greatest fluorescent signal and increase therein as concentration of the inoculum increased followed by CNIR10 and CNIR9. CNIR4 did not demonstrate an increase in fluorescence. Also, fluorescence from CNIR4, CNIR5, CNIR9, and CNIR10 probes is measured in mice that have been infected with wild type *M. tuberculosis* or with *M. tuberculosis* that has a mutation in the blaC gene in the lungs by aerosol inoculation (FIGS. 19A-19D). CNIR10 showed the highest total fluorescence followed by CNIR9, CNIR5 and CNIR4 (FIG. 19E).

CNIR5 was used as substrate to image fluorescence incorporation and graph the kinetics thereof over time in control mice and mice infected by aerosol with *M. tuberculosis* and imaged using the substrate CNIR5. Images from control and infected mice were obtained at 1, 18, 24, 48, and 96 hr (FIGS. 20A-20E). Peak incorporation of CNIR5 occurred at 48 h after aerosol infection (FIG. 20F). FIGS. 21A-21B depict fluorescence images of uninfected mice or mice infected with *M. tuberculosis* by aerosol, respectively, and imaged using transillumination, rather than reflectance, to reduce background signal.

EXAMPLE 7

In Vivo Imaging with CNIR5: CNIR5 in a Mouse Tumor Model

About $1 \times 10^6$ of C6 rat glioma cells were injected at the left shoulder of a nude mouse and the same number of C6 rat glioma cells that were stably transfected with cmv-bla were injected at the right shoulder of the same nude mouse. When the size of tumors reached about 6 mm, 7.0 nmol of CNIR5 was injected via tail-vein into the mouse under anesthesia. The mouse was scanned in an IVIS 200 imager with the Cy5.5 filter set (excitation: 615-665 nm; emission: 695-770 nm) and 1 second acquisition time at different post injection time.

FIG. 22A is a series of representative images taken before injection and 2, 4, 12, 24, 48 and 72 hrs after injection. As early 2 hrs after injection, cmv-bla tumors displayed higher fluorescence intensity than wild-type (wt) C6 tumors. The contrast reached the highest value of 1.6 at 24 hrs, and then began to decrease to about 1.3 at 48 hrs and 72 hrs (FIG. 22B). At the end of imaging, the mice were sacrificed to collect the organs and tumors for ex vivo imaging and biodistribution studies to corroborate the imaging data. FIG. 22C is the fluorescence image of tumors and organs collected from the sacrificed mouse 24 hrs after the injection of CNIR5, which is consistent with the in vivo imaging data demonstrating higher Cy5.5 emission from excised cmv-bla tumor than wt C6 tumor. To verify the expression of Bla in the cmv-bla tumors, a CC1 assay of excised tumors from mice injected with CNIR5 (FIG. 22D) was performed; the result indicated that cmv-bla tumors had high levels of enzyme expression, whereas wild type tumors possessed little Bla activity.

To further demonstrate that the observed contrast was due to the activation of CNIR5 by Bla expressed in tumors, CNIR6, an analog of CNIR5 but without the peracetylated D-glucosamine, was prepared as a control (FIG. 23A). CNIR6 can be hydrolyzed in vitro by Bla as efficiently as is CNIR5, but is not cell-permeable and thus CNIR6 should not be able to image Bla in vivo. In the FIGS. 23B-23C, there was not any significant contrast between cmv-bla tumors and control tumors throughout the whole imaging period. This clearly indicated that CNIR5 entered into target cells and was activated by Bla. This result also demonstrated the importance of the D-glucosamine group for CNIR5 to image Bla in vivo.

Biodistribution and Pharmacokinetics of CNIR5 in Mice after i.v. Inoculation

CNIR5 is injected i.v. into Balb/c mice. Groups of mice are sacrificed for organ collection and processing. The presence of CNIR5 is evaluated by fluorescence intensity in each organ over time. FIGS. 24A-24B shows the CNIR5 signal at 4 h and 24 h post injection, respectively. Stable signal is observed in all tissues suggesting that over 24 h CNIR5 is systemic and not degraded significantly over this time.

In Vivo Imaging to Locate *M. Tuberculosis* Infection in Mice with Bla

Six groups of four Balb/c mice each are infected by aerosol with between 100-1000 cfu/lung as described in Example 1. One group of four mice are used for imaging at all time points and at each time point another group of four mice are sacrificed and necropsied for histopathology and to determine cfu in lungs and spleen. At 24 h, 7, 14, 28 and 72 days, imaging is carried out in the same ABSL3 suite using a Xenogen IVIS200 imaging station. A control group of four animals are used for imaging that have not been infected with bacteria, but are injected with the detection reagent, to control for background fluorescence from the un-cleaved compound Animals are anesthetized with isofluorane in the light tight chamber and imaged with excitation at 640 nm and images captured at 690 nm. 5 nmol of CNIR5, which has been shown to be sufficient for IVI, are injected intravenously using the tail vein. Images are acquired prior to injection of the compound and 1, 2 and 4 h post-injection. If signal is observed at any of these time points, the animals are subsequently imaged 24, 48 and 72 h later to follow dissipation of the signal.

In vivo images of a mouse that has been infected with wild type *M. tuberculosis* (FIG. 25A) and a control mouse (FIG. 25B) are shown. Both mice were injected with CNIR5 i.v. prior to imaging. This image shows that the infected mouse has signal coming from the lungs. 3D re-construction of the signal demonstrates that the average signal location is between the lungs. Since signal is averaged and mice have two lungs, one would expect this location to be the greatest point source. Thus, the compound CNIR5 can be used to determine the location of *M. tuberculosis* in live mammals. The Xenogen/Caliper IVIS Spectrum imaging system was used to capture this image.

Determining Threshold of *M. tuberculosis* Detection in Mice with Bla

A beta-lactamase CNIR probe can detect 100 *M. tuberculosis* bacteria or less with SREL imaging of mice in real time (FIG. 26A). SREL imaging was performed on live mice uninfected, as control, (FIG. 26B) or infected with *M. tuberculosis* (FIG. 26C). The color bar indicates levels of emission at 680 nm after excitation at 620 nm. Color indicates the presence of a strong signal originating from the lungs infected with Mtb, demonstrating specific localization of infection. Thresholds of detection for *Pseudomonas, Staphylococcus* and *Legionella* also may be determined.

In Vivo Imaging of *M. Tuberculosis* Infection in Guinea Pigs with Bla

Six groups of four guinea pigs are infected and imaged in the same manner as described for mice, with the following exceptions. First, only time points post-infection up to 28 days are examined, since guinea pigs are expected to begin showing significant mortality at later time points. Second, 20-fold more (~100 nmol for CNIR5) of the detection reagents are needed in guinea pigs to achieve the same serum levels as that needed in mice and the compound is administered through the lateral metatarsal vein. Guinea pigs are infected by aerosol in the ABSL3 facilities and maintained under containment until imaging. Imaging is carried out in the ABSL3 suite using an IVIS200 imaging station at 24 h, 7, 14 and 28 days post infection. A control group of four animals are used for imaging that have not been infected with bacteria, but are injected with the detection reagent, to control for background fluorescence from the un-cleaved compound.

Prior to imaging, 100 nmol of CNIR5, which has been shown to be sufficient for IVI, is injected intravenously using the tail vein. Images are acquired prior to injection of the compound and 1, 2 and 4 h post-injection. If signal is observed at any of these time points, the animals are subsequently imaged 24, 48 and 72 h later to follow dissipation of the signal.

EXAMPLE 8

Detection of Tuberculosis in Clinical Samples with CNIR5

Thirty clinical isolates were obtained directly from clinical laboratories, including approximately half that were positive for tuberculosis and half that were negative as determined by standard clinical lab testing (acid-fast direct concentrated smear, acid fast culture and mycolic acid HPLC). These clinical samples were primarily sputum (26 samples), but there were 4 bronchial washes. The sputum samples were both un-induced (24 samples) and induced (2 samples). There were four *M. avium* complex (MAC) samples within the positive samples. Each of these samples was examined in a blinded fashion in two independent tests that obtained comparable results for specificity (>94%) and sensitivity (>86%) of the test.

The clinical samples were evaluated using the CNIR5 substrate (FIG. 27A). Only one false positive was obtained (sa6), but this patient displayed clinical disease, but was negative by standard culture and sputum tests. One false negative was obtained (sa29), but this patient was also negative by culture. Samples sa18, sa20 and sa24 were *M. avium*. Negative sputum samples were also used for spiking experiments to determine the threshold of detection (~100-1000 CFU) and, preliminarily, to optimize assay conditions (FIG. 27B).

Similar thresholds of detection were obtained directly with clinical samples to that obtained with tuberculosis in phosphate buffered saline (PBS) in more than three independent experiments. In sputum spiked with known numbers of tubercle bacilli, there was an extremely good correlation (R2=0.9) of signal intensity produced relative to bacterial numbers present (FIG. 27C). The sensitivity was such that detection of 100 bacteria was demonstrated, which is in range of the sensitivity needed to produce a diagnostic test comparable to culture. Interestingly, there was little difference using this system between their reliability and quantitative nature whether using laboratory buffer (PBS) and sputum, suggesting that the system is quite robust (FIG. 27D).

In addition, the ability to indicate a correlation between bacilli count and signal strength provides the basis for the drug susceptibility protocol used to identify isoniazid and rifampicin resistance in 4 to 12 hours. This potential has been validated by analysis of anti-tuberculosis therapy using the substrate CNIR5, which displays clear differences between the treated and untreated groups in less than 24 h post-treatment (FIG. 27E). These data indicate that susceptible versus resistant bacteria can be differentiated in under 24 h using the substrates provided herein. It is contemplated that optimized variants of these substrates would improve the diagnostic assay and lower the threshold of detection.

EXAMPLE 9

In Vivo Imaging with CNIR7: Biodistribution of CNIR7 in Mouse Tissues

The biodistribution of CNIR7 in mouse tissues is evaluated prior to in vivo imaging. CNIR7 is intravenously injected in three mice (at a dose of 10 nmol in 100 µL of saline buffer). Anesthetized mice are sacrificed by cervical dislocation at different time intervals (30 min, 240 min, 12 hr, 24 hr, 48 hr, and 72 hr) postinjection (three mice at each time point). Blood samples are collected by cardiac puncture and tissues (heart, kidney, liver, bladder, stomach, brain, pancreas, small and large intestine, lung, and spleen) are harvested rapidly to measure the near-infrared fluorescence by a fluorometer. Data is expressed as fluorescence unit (FU) of per gram of tissue [FU/(g tissue)] and indicate the amount of the hydrolyzed CNIR7 product in these tissues organs.

In Vivo Imaging with CNIR7 in Mouse Model

C6 glioma tumor xenograft was used in nude mice, for CNIR7 imaging. Mice are anesthetized with the inhalation of 2% isoflurane in 100% oxygen at a low rate of 1 L/min. The lateral tail vein is injected with 10 nmol of CNIR7 in 100 µL of PBS buffer. Three mice are imaged with a small-animal in vivo fluorescence imaging system using the IVIS200 Optical CCD system (Xenogen Inc). This system is suitable for both bioluminescence and fluorescence in vivo imaging and can scan a small rodent quickly for a single projection, i.e., as short as 1 second for fluorescence imaging. Full software tools for visualization are also available with this system. For the NIRF imaging with Cy5.5, a filter set with an excitation filter (640±25 nm) and an emission filter (695-770 nm) is used. Fluorescence images will be collected with a monochrome CCD camera with high sensitivity to the red light equipped with a C-mount lens. Mice are sacrificed for the biodistribution study. A portion of tumor tissue samples are used for assessment of Bla activity.

EXAMPLE 10

Biodistribution and Pharmacokinetics of CNIR800 in Mice after i.v. Inoculation

Mice are inoculated I.V. with 2.5 µl/g of three different doses of CNIR800 at 10, 20 and 40 µM. At different time intervals from 1, 3, 5, 10, 24, 48 h post-administration. Anesthesized mice are sacrificed by cervical dislocation (three mice at each time point). Blood samples are collected by cardiac puncture and tissues (tumors, heart, kidney, liver, bladder, stomach, brain, pancreas, small and large intestine, lung, and spleen) are harvested rapidly to measure the near-infrared fluorescence by a fluorometer. Those samples are processed with the addition of sodium hydroxide to hydrolyze all non-activated probes for fluorescence measurement. Biodistribution of both activated and non-activated probes can thus be obtained, and data is expressed as fluorescence units (FU) per gram of tissue [FU/(g tissue)]. Thus, optimal concentrations of substrate in tissues is determined.

Determining Threshold of *M. Tuberculosis* Detection in Mice with Bla

Female Balb/c mice, five per group with one uninfected control, 5-7 wks old are infected by the pulmonary route. Inocula of 50, 500, 5000, 50,000 and 500,000 cfu/lungs is utilized. Two groups of mice are infected at each inoculum and one group is not imaged, but is sacrificed on day 1 and lungs are plated for cfu to confirm the inoculum. In the other groups of mice, the optimal dose of CNIR800 is given I.V. and the mice imaged immediately afterward and 1, 3, 5, 10, 24, 48, and 72 h after substrate delivery.

Optimizing the concentration of substrate is accomplished by imaging experiments using inocula two-fold higher than the determined threshold of detection and two-fold lower than this threshold at a two-fold lower and a two-fold higher concentrations of substrate, for a total of four additional conditions. Concentrations of inocula and substrate demonstrating improvement in the signal to noise ratios can be used to again determine the optimized threshold of detection.

CNIR800 REF Imaging Correlation with cfu During Infection

Mice are female 5-7 wk old Balb/c maintained on low chlorophyll chow, to reduce autofluorescence, and water. Five animals per group are utilized with a control that is uninfected and four that are infected. All animals receive substrate delivered at 2.5 μl/g of 20 μM CNIR800 prior to imaging. Doses corresponding to (group#×number of groups of 5): 1) 100 cfu×3, 2) 1000 cfu×1, 3) 10,000 cfu×6, 4) 100,000 cfu×1 and 5) 106 cfu×1 are deposited in the lungs. Mice from Group 1 are first imaged at 7 days. If signal is observed, the animals are sacrificed and cfu determined. If signal is not observed, the animals are imaged every day until signal is observed, the day is noted and cfu determined. This is the time point at which physiologically relevant infections become visible by REF and the first time point at which therapy could begin. The other two Group 1 sets of animals are imaged at 28 and 60 days post-infection. Group 2 is imaged at 4 days and is handled in the same manner as group 1 until signal is observed and cfu is determined. In Group 3 one set of animals are imaged at day 1, 3, 5, 7, 14, 28 post-infection and cfu is determined. In Group 4 and 5 the animals are imaged at day 1 and cfu is determined.

For I.V. inoculation, doses correspond to 1) 104 cfu×1, 2) 105 cfu×2, 3) 106 cfu×1, 4) 107 cfu×1. All of these groups are handled in the same manner and are imaged on day 1, 2, 3, 4, 5, 6 and 7. Once signal is observed, the group is sacrificed, except in the case of the second group of animals in Group 2, which are imaged at each time point out to 7 days and are sacrificed on this last day. Fluorescence incorporation at the site of infection is visualized using the IVIS imaging system at the whole animal and excised organ level and confirmed in tissue homogenates with a fluorometer and using tissue cryosections and fluorescence confocal microscopy.

Therapeutic Screening by CNIR800 REF Imaging

Female 5-7 week old Balb/c mice are infected with 100-1000 cfu/lungs using the Madison chamber 4 days prior to treatment. 10 animals per group are utilized with two animals that are not infected as controls for imaging and five animals per group for conventional cfu studies. One group of animals are treated and a second group are untreated in all experiments. All animals are imaged prior to treatment on day 3 to obtain a baseline, therapeutic treatment is begun on day 4 and imaging is performed on day 5, 6, 7, 14 and 28 days post-infection. In parallel one group of five animals is sacrificed on day 4, 7, 14 and 28 days post-infection for standard therapeutic evaluation. Also, daily treatment with 5, 10, 25 and 50 mg/kg for INH, RIF and MOX in an I.V. inoculation model of 106 cfu by the tail vein. Comparison is made to conventional imaging and therapeutic techniques using treatment with 25 mg/kg INH.

EXAMPLE 11

Fluorescent Proteins: Evaluate the Potential of Fluorescent Proteins for IVI

The fluorescent protein (FP) mPlum has the longest wavelength of 649 nm and quite a good Stokes shift of 59 nm, which means that it will both penetrate tissue quite well and have a good signal to noise ratio. Although it is not as bright as EGFP, it has a similar photostability and its wavelength and Stokes shift should more than make up for this difference during IVI, though it may not behave as well in vitro. A second FP that has a long wavelength (620 nm) is mKeima, which has an even better Stokes shift than mPlum, at 180 nm where there is little concern that background will be due to overlap in the excitation wavelength. However, mKeima has a similar brightness to mPlum, making it unclear which FP will behave better during IVI. Another FP with a relatively long wavelength (610 nm) that is four-fold brighter than either mPlum or mKeima is mCherry. The Stokes shift for mCherry is only 23 nm, so the signal to noise ratio may remain a problem despite the greater brightness. The FP tdTomato has the shortest wavelength (581 nm), but is also the brightest at as 20-fold brighter than mPlum and mKeima.

The four FP, mPlum, mKeima, mCherry and tdTomato are cloned into the expression vectors using Gateway PCR cloning. Each of these constructs is transformed into Mtb and is evaluated in vitro using 96-well plate assays. They are evaluated in culture medium under standard growth conditions and with the intracellular growth assays. All constructs are evaluated spectrophotometrically and by microscopy using 8-well chamber slides. Spectrophotometric studies evaluate the optimal excitation wavelength as well as the optimal emission wavelength for each construct. EGFP is used as a negative control for emission at long wavelengths and vector alone to evaluate the effects of autofluorescence from the bacteria and macrophages themselves. Microscopy allows for evaluation of any variability in signal strength and stability of the various vectors after growth in culture medium through calculation of the percent fluorescence in the bacterial population.

In Vitro Evaluation Panel for FP

FP constructs are evaluated for stability in culture, efficiency of transcription and translation, limit of detection and signal during/after isoniazid treatment. Initially at least two transformants with each FP construct are chosen for evaluation, since variability in signal intensity and construct stability has previously been observed in individual FP transformants. A single optimal strain for each FP is then chosen in vivo studies.

Stability in culture is evaluated by growth of each strain in the absence and in the presence of selection and determination of the percentage of bacteria that remain fluorescent after 30 days growth. This is confirmed by plating dilutions in the presence and absence of the appropriate antibiotic to evaluate the percentage of bacteria in the culture that carry the selectable marker from the plasmid. Transcriptional and translational efficiency studies provide insight into whether the promoter is functioning properly in each construct and whether codon usage is affecting translation to the point that it may affect signal intensity. This is evaluated by RT-PCR from Mtb carrying each FP construct to compare the fold induction using the different promoters and single- or multi-copy vectors to correlate this induction with constructs expressing other reporters. These ratios should be comparable regardless of the reporter expressed.

Fluorescent intensity and protein levels are measured and compared for each strain using spectrophotometry and Western analyses, respectively. The ratios of protein to RNA to fluorescent signal should be comparable, regardless of the reporter expressed or the level of RNA transcript expressed. If some reporters are translated inefficiently, their ratios of protein to RNA transcript will likely decrease with increased levels of RNA expression. Such observation is interpreted as a need to correct codon usage for that FP to improve the efficiency of translation. However, it is also possible that this is the result of protein instability or sequestration in inclusion bodies upon overexpression.

Limit of detection is determined by evaluating the fluorescence of limiting dilutions from cultures prepared in parallel. These data are evaluated relative to CFU and by fluorescent microscopy quantitation to confirm that the numbers obtained by fluorescence correlate directly with viable bacteria. Effects of isoniazid (INH) treatment are evaluated by the addition of 1 µg/ml isoniazid to cultures that have already been evaluated for CFU and fluorescence in a 96-well format assay. CFU and fluorescence is followed in real time using a spectrophotometer with an incubating chamber set to 37° C. and by taking aliquots to plate for CFU immediately after addition and various time points out to 48 h post-addition of INH. This provides insight into the signal strength, stability and signal duration after antibiotic treatment for each construct.

Stability and Effects on Virulence of Select Recombinant FPs

In virulence studies all strains are compared to wild type in parallel. Twenty groups of four Balb/c mice are infected by aerosol with between 100-1000 cfu/lung as described in Example 1. One group of four mice for each bacterial strain (wild-type, FP1, FP2, FP3, FP4) are necropsied at all time points (1, 14, 28 and 72 days) to determine CFU, carry out histopathology, determine the presence of the appropriate construct and level of fluorescence in lungs and spleen. The percentage of the bacterial population that carry the construct is determined by fluorescence microscopy conducted on at least 20 individual colonies from the CFU titer plates. Fluorescence levels are measured homogenized tissues to evaluate overall levels of FP remaining.

Fluorescent Proteins in Mice Infected by Aerosol.

Six groups of four Balb/c mice each are infected by aerosol with between 100-1000 cfu/lung of each bacterial strain carrying the mPlum, mKeima, mCherry and tdTomato constructs and the vector backbone alone (a total of 30 groups). Bacterial strains are thawed for aerosol infections as described in Example 1. Five groups of four mice, one with each FP and one with vector alone, are used for imaging at all time points and at each time point another five groups of four mice are sacrificed and necropsied for histopathology and to determine cfu in lungs and spleen. At 24 h, 7, 14, 28 and 72 days, imaging is carried out in the same ABSL3 suite using a Xenogen IVIS 200 imaging station, using optimal excitation and emission filters for each FP. When FP require use of a different set of filters in the IVIS, the vector also is imaged alone in each animal group using the same filter set to control for autofluorescence. Thus, each FP for IVI is validated as well as the sensitivity of this system, since the bacterial load will vary throughout the experiment from very low (100 cfu/lung) to very high (>$10^5$ cfu/lung) at later time points post-infection. The use of vector alone controls for both autofluorescence and for potential differences in virulence brought about by the presence of the FPs.

EXAMPLE 12

Click Beetle Red (CBR) for Detection of Tuberculosis in Culture Medium

The CBR gene is cloned into all four of the constructs described for Bla using the Gateway recombination sites already introduced. These plasmids allow expression from both the L5 and hsp60 promoters. The ability of each strain to produce light in the presence of D-luciferin is compared in growth medium using 96-well plates in multi-mode microplate reader with luminescent detection capability and injectors to allow measurement of flash emission during addition of D-luciferin as well as persistent signal degradation kinetics. All assays are done in quadruplicate with limiting dilution of the bacteria and determination of CFU to allow correlation of viable bacterial numbers with signal produced. Stability of the constructs is evaluated by growth in the absence of selection for 7 days followed by spectrophotometric and fluorescent microscopic examination. These data are correlated with CFU to determine the signal/viable *bacillus* and microscopy is used to calculate the percentage of bacteria producing a positive signal. Effects of the constructs on bacterial viability is evaluated in these assays by plotting growth of bacteria that carry this construct as compared to bacteria with vector alone.

Evaluate CBR Expression, Stability and Virulence in Mice

Stability and effects on virulence of recombinant CBR are examined for two strains that display promise for IVI. In virulence studies all strains are compared to wild type in parallel. Twelve groups of four Balb/c mice are infected by aerosol with between 100-1000 cfu/lung as described in Example 1.

One group of four mice for each bacterial strain (wild-type, CBR1 and CBR2) are necropsied at all time points (1, 14, 28 and 72 days) to determine CFU, carry out histopathology, determine the presence of the appropriate construct and level of luminescence in lungs and spleen. The percentage of the bacterial population that carry the construct is determined by fluorescence microscopy conducted on at least 20 individual colonies from the CFU titer plates. Luminescence levels also are measured homogenized tissues to evaluate overall levels of CBR remaining.

Image CBR Expressing Tuberculosis and BCG Strains in Mice

Six groups of four Balb/c mice each are infected by aerosol with between 100-1000 cfu/lung of each bacterial strain carrying the RLuc8 and the vector backbone alone (a total of twelve groups) as described in this Example 1. Two groups of four mice, one with the RLuc8 and one with vector alone, are used for imaging at all time points and at each time point another two groups of four mice are sacrificed and necropsied to determine cfu in lungs and spleen. At 24 h, 7, 14, 28 and 72 days, imaging is carried out in the same ABSL3 suite using a Xenogen IVIS 200 imaging station. Prior to imaging 1-5 μmol of the D-luciferin, which has been shown to be sufficient for IVI, is injected intravenously using the tail vein.

Images are acquired prior to injection of the compound and 1, 2 and 4 h post-injection. If signal is observed at any of these time points, the animals are subsequently imaged 24, 48 and 72 h later to follow dissipation of the signal Animals are anesthetized with isofluorane anesthesia at 2% isoflurane in 100% oxygen using the Matrix system (Xenogen) in the light tight chamber and are imaged using an integration time from 3 to 5 min with 10 pixel binning. This allows validation of the utility of CBR for IVI as well as the sensitivity of this system, since the bacterial load varies throughout the experiment from very low (100 cfu/lung) to very high ($>10^5$ cfu/lung) at later time points post-infection. The use of vector alone controls both for autofluorescence and for potential differences in virulence brought about by the presence of the CBR gene.

EXAMPLE 13

Evaluate Potential of Other Luciferase Systems for IVI

The RLuc8 luciferase is cloned into the described mycobacterial expression systems using Gateway PCR cloning. Constructs are introduced into Mtb and are examined for their light production in bacterial culture medium using whole cells. Should intact bacteria produce comparable light to CBR, then an intracellular bacterial system can be compared to CBR in mice. The Gram-positive and Gram-negative bacterial luciferase systems both have the advantage that they produce their own substrate. Both operons are cloned into expression systems using restriction digestion to remove them from their current vector followed by ligation to Gateway adapters and Gateway recombinational cloning. Constructs are examined for light production from Mtb in bacterial medium. All assays for bioluminescence are carried out in 96-well plates as described for the Bla system, except that light production will be measured on the luminescence setting for the spectrophotometer. Sensitivity is evaluated by limiting dilution and CFU determination carried out in parallel on all samples so that light production can be calculated relative to CFU.

Detecting Tuberculosis in Macrophages Using Luciferases

The effects of secretion and targeting to the membrane on luciferase activity in macrophages is examined Secretion from mycobacteria is achieved by attaching the amino-terminal TAT signal signal sequence from the Mtb BlaC (BlaSS) and placing this fusion in the same construct that optimally expresses CBR in Mtb. Secretion is confirmed by assaying culture filtrates and whole cells from the CBR, BlaSS::CBR and vector alone expressing Mtb strains grown to early log-phase. Culture filtrates from this strain should have much higher light production than the CBR expressing strain and whole cells from BlaSS::CBR should have the same or lower light production than CBR Mtb. The carboxy terminal GPI anchor from CD14 used for Bla is attached to BlaSS::CBR to produce the fusion protein BlaSS::CBR::GPI.

Mtb expressing BlaSS::CBR::GPI is evaluated for light production, using intracellular macrophage assays, as compared to strains expressing CBR and BlaSS::RLuc8. J774A.1 macrophages are used in 96-well plates so that titration of bacteria and various concentrations of the compounds can be examined. All assays are carried out in quadruplicate in the same manner as described for Bla. Duplicate wells are lysed with 0.1% Triton X-100 prior to adding D-luciferin to evaluate the role of host cell permeability in the measurements obtained. At all time points four untreated wells are used to determine the number of CFU associated with the cells. Detection of CBR intracellularly may be affected by the permeability of eukaryotic cells and the mycobacterial vacuole for D-luciferin, so evaluation of its sensitivity for bacteria within macrophages will be extremely important. The bacterial luciferase systems, however, are unlikely to be significantly impacted by growth of the bacteria intracellularly.

Light production in each of the bacterial luciferase systems and RLuc8 is confirmed using intracellular assays. Duplicate wells are lysed with 0.1% Triton X-100 prior to adding coelenterazine to evaluate the role of host cell permeability in the measurements obtained for RLuc8. Localization of the signal is confirmed by for those constructs that prove the most effective. These assays are carried out in a similar manner, but using eight-well chamber slides. Microscopy allows localization, determination of the percentage of bacteria with a positive signal and evaluation of the intensity of localized signal.

EXAMPLE 14

Detection of Bgal by Compounds for IVI

The promoterless Bgal gene previously described (17) is cloned into the mycobacterial expression vectors by restriction enzyme digestion and ligation to Gateway adapters. These vectors are transferred into Mtb for evaluation in bacterial culture medium using the mycobacterial permeable fluorescent reagent 5-acetylamino-fluorexcine di-beta-D-galactopyranoside (C2FDG), in 96-well plates as described previously (18). This compound is not fluorescent until cleaved by Bgal, excited at 460 nm and emits at 520 nm. The vector that produces the strongest fluorescent signal is used to construct additional fusions that allow secretion of Bgal and host cell localization.

Secretion of Bgal is important to help determine whether mycobacterial permeability plays a role in the ability of different compounds to detect Bgal. In order to secrete Bgal, the amino-terminal TAT signal sequence from the Mtb BlaC (BlaSS) is attached and this fusion is placed in the same construct that optimally expresses Bgal in Mtb. Secretion is confirmed by assaying culture filtrates and whole cells from the Bgal, BlaSS::Bgal and vector alone expressing Mtb strains grown to early log-phase. The same carboxy terminal GPI anchor from CD14 used for Bla is attached to BlaSS::Bgal to produce the fusion protein BlaSS::Bgal::GPI.

All Bgal constructs are evaluated for the sensitivity of fluorescent detection with C2FDG, 5-dodecanoylaminoresorufin di-beta-D-galactopyranoside (C12RG) and 9H-(1,3-dichloro-9,9-dimethylacridin-2-one-7-yl) beta-D-galactopyranoside (DDAOG). All compounds are commercially available from Molecular Probes, part of Invitrogen. Since C2FDG is known to enter and detect Bgal in Mtb efficiently, this compound provides the positive control, though its wavelength of emission is not advantageous for IVI. C12RG, enters eukaryotic cells well and has a longer emission wavelength (590 nm), but a similar compound C12FDG, does not detect Bgal well in Mtb, suggesting that it does not cross the bacterial membrane well.

To confirm the effects of permeability and localization on signal produced, Bgal activity is measured in intact cells and whole cell lysates for all strains and compounds. The compound DDAOG has been shown to work well for IVI, since it crosses eukaryotic membranes well and has the longest emission wavelength after cleavage by Bgal (660 nm). It is contemplated that DDAOG would be the best compound for further studies, should it detect Bgal activity well.

Bgal Expression, Stability and Virulence in Mice

Stability and effects on virulence of recombinant Bgal are examined for two strains that display promise for IVI. In virulence studies all strains are compared to wild type in parallel. Twelve groups of four Balb/c mice are infected by aerosol with between 100-1000 cfu/lung as described in Example 1. One group of four mice for each bacterial strain (wild-type, Bgal1 and Bgal2) are necropsied at all time points (1, 14, 28 and 72 days) to determine CFU, carry out histopathology, determine the presence of the appropriate construct and level of Bgal in lungs and spleen with C2FDG. The percentage of the bacterial population that carry the construct is determined by Bgal assays using C2FDG conducted on at least 20 individual colonies from the CFU titer plates. Bgal levels are measured in homogenized tissues to evaluate overall levels of Bgal remaining at each time point.

Imaging Bgal-Expressing Tuberculosis Strain in Mice

Since all cells from L2G85 mice express Fluc from the ACTB promoter, bone-marrow derived macrophages from L2G85 mice are infected with the Mtb strain expressing Bgal and are compared to the same strain carrying the vector alone. Macrophage infections are carried out with bone marrow-derived macrophages from L2G85 mice infected in the same manner as those for other intracellular growth assays in J774A.1 macrophages. Duplicate wells are lysed with 0.1% Triton X-100 prior to adding Lugal to evaluate the role of host cell permeability in the measurements obtained. At all time points four untreated wells are used to determine the number of CFU associated with the cells. Localization of the signal is confirmed by microscopy for those constructs that prove the most effective. These assays are carried out in a similar manner, but using eight-well chamber slides. Microscopy allows for localization, determination of the percentage of bacteria with a positive signal and evaluation of the intensity of localized signal. IVI studies are carried out in mice using the same protocols as that described for CBR, except that Lugal will be used instead of luciferin for detection.

EXAMPLE 15

Substrate Probe Design Based on Crystal Structure Models of Beta-Lactamases and Other Proteins: BlaC Enzyme Pocket Modeling The *M. tuberculosis* beta-lactamase (BlaC) enzyme pocket is modeled using small molecules to improve probe design and specificity. High-throughput screening of small molecules, such as in small molecule libraries, is used to identify compounds that bind the active site cleft of BlaC and a crystal structure is obtained therefrom. Candidate probes are synthesized and tested in vitro.

Beta-Lactamase-Like Enzymes and Penicillin-Binding Proteins

Two primary beta-lactamase-like proteins (BlaX) and two primary penicillin-binding proteins (PBP) in *M. tuberculosis* are cloned, overexpressed and purified. Km and binding constants for BlaX and PBP are determined with ceferoperazone, penicillin and ciprofloxacin. The crystal structure for candidate proteins is elucidated and used to design specific probes with improved probe activity.

Structure Activity Relationships Between Mtb Enzymes and *E. coli* Beta-Lactamase TEM-1

The crystal structures of BlaC and TEM-1 with cefoperazone are elucidated. Probes based on ceferperazone are modeled, designed and synthesized. Candidate probes are used to determine the Km for BlaC and TEM-1.

EXAMPLE 16

Improving REF Sensitivity Through Novel Quenchers and Dyes

Previous substrates used for REF imaging have been successful for imaging pulmonary infections of tuberculosis in mice, suggesting that this strategy holds great promise. However, since the threshold of detection in the lungs is >10,000 bacteria, it would be advantageous to improve detection through increasing the sensitivity of the REF probes. Recently, a new dye and quencher have been developed by LiCor that works in the 800 nm range, offering great promise to improve the compounds. This novel dye, designated IRDye 800CW is approximately 10-fold brighter than the Cy5.5 and due to its long wavelength should penetrate mammalian tissue much better than Cy5.5. Compounds based on this dye and the matched quencher designated QC-1, are designed. A compound based on this dye and quencher allows improvement on the current REF system significantly. Also explored are two IRDye800 dyes, IRDye800RS and IRDye800CW (FIG. 27) as the FRET donor for in vivo imaging application. Both have the same fluorescence spectra with excitation at 780 nm and emission at 820 nm, but they differ in that IRDye800CW bears more sulfonate groups than IRDye800RS. This difference may lead to different in vivo biodistribution, and thus both are explored. A corresponding dye with high quenching efficiency for IRDye800, IRDye QC-1, is used as the FRET acceptor in the fluorogenic probe (FIG. 28). Incorporation of these molecules into the probe is the same as the synthetic procedures used to prepare CNIR5 with the same coupling chemistry between the NHS ester and amine, as described supra. First the hydrolysis kinetics of these CNIR probes made of IRDye800 dyes is characterized by both TEM-1 Bla and Mtb BlaC, and the probes are evaluated for in vivo imaging of Mtb in sub-cutaneous and pulmonary infections.

The compounds based on IRDye 800CW are first examine in vitro, followed by intracellular studies and animal model work to validate it in sub-cutaneous and pulmonary infections. Fluorescence incorporation at the site of infection is visualized using the IVIS imaging system at the whole animal level and confirmed in tissue homogenates in the fluorometer, using tissue sections and fluorescent confocal microscopy and intravital microscopy of infected tissues at the cellular level. The combination of these techniques is applied to all probes that are examined in the mouse model of infection to allow detailed characterization of the labeling characteristics of infected tissues and the incorporation of the probe within infected host cells.

Improving SREL and REF Sensitivity Through Structural Modification of Substrates.

While current substrate probes can detect and image Mtb BlaC activity, its activity for Mtb BlaC is not optimal. A probe that improved enzyme kinetics with the Mtb BlaC would provide greater sensitivity for both detection and imaging. The crystal structure of the Mtb BlaC shows a major difference from other class A beta-lactamases, which is that Mtb BlaC has a larger active site pocket. This structural difference suggests the possibility of designing a probe with improved kinetics for the Mtb BlaC. Three major approaches are utilized for improving the structure of BlaC probes modification based on cefoperazone, screening of a limited library of compounds and modification of leaving groups. Identified appropriate compounds are further characterized using in vitro assays with Mtb, intracellular bacteria and infections in mice by the sub-cutaneous and pulmonary routes.

A rational approach based on the structure of cefoperazone.

Kinetics of CNIR5 by TEM-1 Bla and Mtb BlaC:

for TEM-1 Bla, $k_{cat}=0.33$ s$^{-1}$, $K_M=1.9$ μM, $k_{cat}/K_M=1.74\times10^5$ s$^{-1}$M$^{-1}$;

for Mtb BlaC, $k_{cat}=0.07$ s$^{-1}$, $K_M=5.9$ μM, $k_{cat}/K_M=1.2\times10^4$ s$^{-1}$M$^{-1}$.

This kinetic data indicates that CNIR5 is a preferred substrate for TEM-1 Bla but not for Mtb BlaC. In order to identify the structural elements required for specific activity for Mtb BlaC, the kinetics for a number of cephalosporin lactam antibiotics (cefoperazone, cephalotin, cefazolin, ceftazidime, cefoxitin, cefamandole, cefotaxime, and cephalexin) was measured with TEM-1 Bla and Mtb BlaC. The results showed that cefoperazone (FIG. 28) is a preferred substrate for Mtb BlaC as compared to TEM-1 Bla.

for TEM-1 Bla, kcat=0.26 s−1, KM=262 µM, kcat/KM=1× 103 s−1M−1;

for Mtb BlaC, kcat=2.01 s$^{-1}$, KM=76 µM, kcat/KM=2.6× 104 s−1M−1.

Its value of kcat/KM for Mtb BlaC (2.6×104 s−1M−1) is better than that of CNIR5 (1.2×104 s−1M−1), but its value of kcat/KM for TEM-1 Bla (1×103 s−1M−1) is 100-fold smaller than that of CNIR5 (1.74×105 s−1M−1). It is hypothesized that the major structural group responsible for this selectivity arises from the bulky group connected to the 7 amine in cefoperazone, which seems to be supported by the finding from the X-ray structure of Mtb BlaC--BlaC has a large substrate binding pocket at the 7 site.

Therefore, the group at the 7 position of cefoperazone is incorporated into CNIR5, and to create an Mtb BlaC probe that should display improved enzyme kinetics (FIG. 29). This probe is examined in vitro first 1) for its stability in buffers and in mouse sera, 2) for its kinetics in the presence of purified Mtb and intracellular Mtb, and 3) its kinetics in the presence of purified TEM-1 Bla. Its membrane permeability characteristics are then compared to CNIR5 to evaluate whether it displays comparable or improved membrane transport and retaining characteristics to those displayed by the previous probes. Then animal studies through sub-cutaneous and aerosol infections are performed followed by imaging with Mtb.

To better understand the structure and activity relationship (SAR) of the cefoperazone CNIR probe, computational modeling of its binding to BlaC was performed. In parallel, the probe was co-crystallize with BlaC to solve the complex structure. The resulting structural information is applied to rationally design an improved probe.

Rapid Limited Structure Library Analysis to Identify Probes with Improved Sensitivity.

After synthesizing and testing the cefoperazone CNIR probe, a library approach is attempted to improve selectivity in parallel with the SAR refinement by X-ray structural study.

Since it is much easier to prepare Bluco than CNIR probes, Bluco-based substrates were utilized to provide a simple and rapid readout for enzyme kinetics. Bluco is utilized as the template to construct a small biased library of cefoperazone analogs. To build up this library and generate the diversity, 8 substituted piperazine 2,3-diones (A) with 6 substituted phenylglycyl methyl esters (B), were utilized, all of which are commercially available. This led to production of 48 members.

The library was then reacted with the Bluco precursor (C) to generate the final 48 analogs of Bluco. The library was prepared on solid support through the carboxylate group on D-luciferin. Before including all of these compounds in the library preparation, a computer modeling study of each member was performed based on the available X-ray structure of BlaC to confirm that all are potentially fitting with the active site pocket of BlaC.

Screening of the library was performed in high throughput assays using a luminescence microplate reader. Before the kinetic screening, the first step was to screen the stability of the compounds in buffers. Kinetics were evaluated by comparing the luminescent levels to the original Bluco substrate and luciferin as a positive control at early time points of co-incubation. Compounds with beneficial kinetics displayed rapid hydrolysis and release of luciferin resulting in high levels of luminescence within minutes after addition of the substrate; whereas the original Bluco molecules display maximal levels of luminescence after several hours of co-incubation. These studies provide novel compounds that can be used as the foundation for CNIR and Bluco substrates that display improved kinetics with BlaC and greater sensitivity for optical imaging.

Modified Leaving Groups for Improved Kinetics: Allylic Linkage at the 3'-Position It has been previously shown that insertion of a double bond between the phenolic ether greatly increases the release kinetics of the phenolic group (19). For example, the $k_{cat}$ has been increased by 5 folds to 54 s$^{-1}$ for a phenolic leaving group. Based on this observation, a double bond was inserted into CNIR probes. For example, for the structure shown in FIG. 28, the corresponding probe is shown in FIG. 31. While in the previous examples the double bond has a cis configuration, it is expected that the configuration here would be trans due to the much larger allylic group. Similarly, an inserted double bond into Bluco leads to Bluco2, which is expected to have better kinetics than Bluco (FIG. 30).

Carbamate Linkage at the 3'-Position

A second type of linkage at the 3'-position offers faster fragmentation after hydrolysis thus better sensitivity. This design utilizes the carbamate linkage and the amino analogue of D-luciferin, amino D-luciferin. The carbamate linkage has been widely used in the prodrug design as an excellent leaving group. The Bla cleavage releases the carbamate that subsequently decomposes into the carbon dioxide and free amino D-luciferin (FIG. 32), a substrate for luciferase. Similarly, this linkage is applied to the CNIR probe as well (FIG. 32).

Improving SREL and REF Sensitivity Through Evaluation of Tissue Distribution.

Tissue distribution studies have been conducted using the fluorescence of CNIR substrates to determine concentrations present. Since cleavage increases fluorescence the distribution of uncleaved substrate was determined by incubating in the presence of BlaC and measuring fluorescence and cleaved substrate concentrations were determined by direct fluorescence evaluation. Although this method approximates the presence of the substrate in tissues, it is not definitive, since autofluorescence within tissue samples, the presence of potential inhibitors and spontaneous hydrolysis of the substrate could impact the data obtained. More detailed tissue distribution data is obtained through examination of the distribution of radioactive labeled probe. CNIR5 is labeled with radioactive iodine such as I-125 so it can be easily follow the distribution of the probe in vivo. Aromatic groups in CNIR5 are similarly iodinated using the protocol that labels tyrosine in proteins. The labeled probe is injected in mice and dynamic SPECT imaging performed. At different intervals, mice are sacrificed to collect organs to count the radioactivity. In parallel, the free fraction of probe is directly evaluated using HPLC using soluble fractions obtained post-necropsy. Tissue (total and soluble) homogenates are evaluated by fluorescence using cold probe and soluble by HPLC followed by scintillation detection of fractions for hot probe. The same experiment will be done with the new Mtb-specific probes when they are developed and validated to provide insight into their potential to improve tissue distribution.

Improving the Sensitivity of SREL and REF Through Use of Beta Galactosidase.

Since it is possible that a different SREL/REF enzyme system would have significant advantages over BlaC due to better enzyme kinetics or substrates available, beta-galactosidase (lacZ) with fluorescent (DDAOG) or luminescent substrates (Lugal) for SREL/REF with Mtb were utilized. Both DDAOG and Lugal were successfully utilized for in vitro imaging and Lugal for imaging sub-cutaneous infections in mice. Although DDAOG has shown promising results in vitro, it has not been evaluated in vivo. It will be important for us to determine whether DDAOG is as sensitive as Lugal in vivo, because the use of a fluorescent substrate would have some advantages over the luminescent substrate that requires luciferase to be delivered along with the substrate. This system has similar issues to those for Bluco. DDAOG or modified compounds that are improved based on DDAOG may ultimately prove to be one of the most sensitive systems and there are a number of colorimetric reporter systems already in use by numerous investigators that would make this system immediately valuable in the tuberculosis community, should it be successful at imaging tuberculosis infections in live animals with it.

EXAMPLE 17

Improving SREL and REF Probe Specificity Using Large Lactams

A similar strategy to that used to develop probes with improved sensitivity is used to develop probes that are selective for the Mtb BlaC over the beta-lactamases present in other bacterial species. The best characterized of these beta-lactamase enzymes is the *E. coli* TEM-1, which are used for a number of kinetic assays and has been used as a valuable reporter in eukaryotic systems. The primary difference in the approach that is used as compared to that for improving sensitivity is the focus on compounds that have the greatest differential between the Mtb BlaC and the *E. coli* TEM-1 in kinetics. Although most beta-lactams display better kinetics with the TEM-1 enzyme, three beta-lactams have been identified that display better kinetics with the Mtb BlaC than TEM-1. These are cefoperazone, cefotaxime and cefoxitin. These compounds vary in their kinetics significantly, but cefoperazone displays between 10-100-fold faster kinetics with the Mtb enzyme than the TEM-1 enzyme, suggesting that it is a good candidate for development of probes that are specific to this enzyme. A CNIR compound is constructed based on cefoperazone, its specificity is examined through determination of its enzyme kinetic parameters using purified BlaC and TEM-1 in a 96-well format with fluorescence as the readout.

Improving SREL and REF Probe Specificity Using Limited Structural Libraries.

The library of compounds that have been developed in Example 16 can also be used to improve the specificity of the SREL and REF probes, but a modified high throughput screen is used that focuses on specificity, rather than enzyme kinetics. Basically, each compound is synthesized as a Bluco-based substrate as described above and the compounds are evaluated in the presence of purified BlaC and TEM-1 in the high throughput luminescent assay. All compounds are screened with BlaC to identify hits and with TEM-1 Bla to identify those that are poor substrates for other enzymes. In addition, all compounds are pre-screened for stability at 37° C. in water to ensure only stable compounds are taken forward. Assays are carried out in parallel and all results expressed as the ratio of BlaC to TEM-1 luminescence. In the beginning, the threshold was set at molecules that display greater than 10-fold more rapid kinetics with the BlaC enzyme after 30 minutes of reaction. Each compound is computer-modeled against the crystal structure of the BlaC and TEM-1 enzymes to establish solid structure-activity relationships (SAR). The assumption that these findings can be translated to the CNIR substrates used for REF was first confirmed by comparing the activity of cefoperazone probes that are CNIR and Bluco-based. With these data in hand, lactams that are identified with good specificity are developed further into REF probes and evaluated for their ability to detect Mtb whole cells in vitro, when grown intracellularly within macrophages and during infections in mice after sub-cutaneous and aerosol inoculation.

EXAMPLE 18

Evaluation of CBR for Imaging in Living Mice

Initial studies have found that the click beetle red (CBR) luciferase functions very well as a reporter for Mtb in vitro and in tissue culture cells. CBR was found to be comparable to firefly luciferase (FFlux) in terms of signal produced and threshold of detection in vitro. However, during sub-cutaneous and pulmonary infections of mice, the threshold of detection for CBR was significantly better than FFlux. This preliminary observation may be due to differences in the inoculum, effects on bacterial metabolism in vivo or to kinetics of luminescence. Each of these parameters are examined in a careful analysis of the utility of CBR as a reporter for the viability of Mtb during pulmonary and sub-cutaneous infection. The kinetics of luminescence is evaluated and compared directly to FFlux in the same animals using sub-cutaneous inoculation at different sites and in combination using spectral unmixing of the bioluminescent signal to demonstrate the reporter that is responsible. Pulmonary infections are evaluated separately in pairs of mice infected in parallel with comparable numbers of bacilli. Insight is obtained into the potential sensitivity of CBR within hypoxic lesions by examining the effects on signal intensity in vitro under low oxygen conditions. Other stresses are examined that may be encountered in vivo, such as low pH and the presence of ROS and RNS.

Analysis of CBR Imaging for Therapeutic Evaluation.

Since CBR luciferase signal is dependent upon the presence of ATP, this imaging system offers the unique opportunity to rapidly evaluate the effects of therapeutics on bacterial viability. Some of the main questions regarding this system are how rapidly a measurable difference in signal will be obtained and how accurately it can be used to determine MICs. MICs are determined for Mtb using this assay for isoniazid and rifampicin. The MIC determined in experiments are compared to that obtained with OD and CFU-based assays. Kinetics of signal loss are evaluated in the presence of the 0.5×, 1× and 5×MIC of antibiotic using whole Mtb assays and intracellularly in macrophages. Once the kinetics have been determined in vitro and compared to differences in viability by CFU, the ability to grow out the bacteria after treatment and whether there remains a good correlation between CFU and luminescence is evaluated. Once the correlation between CFU and luminescence has been determined for in vitro grown bacteria, the kinetics of effects on luminescence on treatment during sub-cutaneous and pulmonary infections in mice is examined. Both routes of inoculation are used because differences are expected between the accessibility of bacteria in the lung and sub-cutaneous environments, making it likely that the kinetics of signal loss will also differ. These studies provide insight into the utility of CBR for rapid evaluation of therapeutics in mice. These experiments focus on the acute phase of infection, to allow results to be obtained rapidly, but subsequent experiments will need to be carried out during the chronic phase of infection in mice to establish whether this system would also be useful for evaluating therapeutics when the bacteria may not be replicating at a high rate.

Development of a Dual CBR-REF Optical Imaging System.

The CBR system is advantageous since it should allow a rapid readout for bacterial viability, but in some cases this type of system may not be optimal. In situations where the bacterial metabolic rate is not sufficient to allow maximal light production, luciferase-based systems may not be as sensitive as under optimal metabolic conditions. Using CBR the impact of therapeutics is evaluated and bacilli in different tissues quantified and REF is used to determine their cellular location. To gain insight into the potential utility of these two systems for evaluation of bacterial numbers in different environments, the kinetics of both CBR and REF signal loss after pulmonary sub-cutaneous infection was examined in mice. Luminescence is immediately reduced upon delivery of antibiotic and REF signal requires as long as 24 h to observe loss of signal. The differential between the sensitivity of CBR and REF to metabolic activity provides the potential to evaluate bacterial numbers in real-time in conjunction with metabolic state. This is an important system to develop because it remains unclear what the metabolic state of all bacteria are during Mtb infection in animals. This imaging system provides the first means by which one could directly observe transit to different environments in live animals by the presence or absence of each signal in real time. This ability is likely to prove particularly important for evaluating therapeutics because therapeutics can be bactericidal in some environmental when they are not in others, a critical consideration for continuation of pre-clinical studies.

EXAMPLE 19

Colorimetric and Chemical Imaging Systems
Colorimetric Assays

A visible assay system can utilize a colored dye as a direct replacement for the fluorophore. Examples of visible dyes are Texas Red, rhodamine, bromocresol dyes (multiple colors), cyanine dyes, etc. Unlike the fluorescent system, these types of dyes are visible and detectable while still attached to the substrate. Therefore separation of bound and free dye is necessary. The free dye travels downstream to a subsequent detection area to be visualized. These dyes are very small molecules, therefore, the free dye may need to be concentrated downstream in order to obtain the necessary, visible by eye, sensitivity.

Chemical Reagent Assays

A visible chemical reagent format also may be utilized in a visible detection system. In place of a dye, a specific chemical such as one that elicits a pH change, or other chemically induced color change, is substituted. The chemical is separated from the conjugate complex, travels downstream to another detection area whereupon the chemical interacts with another reagent resulting in a detectable visible signal. This format differs from the visible dye format in that a concentration method may not be necessary. Some measure of amplification is achieved by the nature of the color change reaction, such as a pH change. The secondary chemical reaction happens downstream of the beta-lactamase reaction, and can be isolated in a cellulose pad containing the dried secondary reagent, for example.

Downstream Detection in Colorimetric and Chemical Reagent Visible Assays

The visible systems are designed to retain the substrate (freed of the detection molecule) and/or whole conjugate (containing bound detection molecule) by, for example, linking the conjugate to a latex particle or to biotin. By linking the conjugate to a latex particle, the particle is retained via a filtration membrane, allowing only the free dye to travel to the detection zone. Alternatively, by linking a biotin to the conjugate, i.e., the substrate along with the dye or chemical reagent, the free and bound material travel to a second region where immobilized avidin binds the substrate and conjugate. Only the free dye travels to the detection zone.

In these visible diagnostic assays latex particles can serve as a solid-phase to which other ligands are bound and immobilized, and they also can be the detector particle through the use of colored dyes. Proteins or other molecules can be permanently attached to the surface of activated microspheres through commonly practiced chemistry. For example, in a diagnostic assay the conjugate may be linked directly to a suitably sized latex microsphere. This reagent is then mixed directly with a decontaminated sputum sample. After a suitable incubation period the mixture is added to the device. The latex particles are trapped by an integrated glass fiber filter, allowing only the free dye (FIG. 33A) or other chemical (FIG. 33B) to travel downstream to the detection zone. The mechanism of liquid travel is via capillary action through a bibulous membrane such as nitrocellulose. The dye is captured through an antibody or other complimentary binding ligand.

In a diagnostic avidin-biotin visible detection system avidin is immobilized on the membrane downstream to capture 100% of the biotinylated substrate. Only the free dye or chemical then flow further along the strip to the detection area. The detection area is essentially identical to the systems presented above. The dye is captured in a line for visualization or the chemical reaction would happen downstream within the absorbent sink. In either the dye (FIG. 33C) or the chemical reagent (FIG. 33D) systems, the substrate/conjugate avidin capture lines can be hidden from view such that the end user cannot see them while interpreting the results of the test. The internal control lines indicate to the user that a valid sputum sample was obtained, and that the test was performed correctly. There are several options for a target common to all human sputum.

The following references were cited herein:
1. Flores et al. 2005, J Bacteriol, 187:1892-1900.
2. Jacobs et al. 1991, Methods Enzymol, 204:537-555.
3. Gao et al. 2003, J. Am. Chem. Soc. 125:11146-11147.
4. Cirillo et al. 1994, Molec. Microbiol., 11:629-639.
5. Lyons et al. 2004, Tuberculosis (Edinb), 84:283-292.
6. Fontan et al. 2008, Infect. Immun. 76:717-725.
7. McMurray, D. N. 2001, Trends Molec. Med., 7:135-137.
8. McMurray, D. N. 1994, Guinea pig model of tuberculosis, p. 135-147. In B. R. Bloom (ed.), Tuberculosis: Pathogenesis, protection and control. American Society for Microbiology, Washington, D. C.
9. Smith, D. W. and Harding, G. E. 1977, Am. J. Pathol. 89:273-276.
10. Weigeshaus et al. 1970, Am. Rev. Respir. Dis., 102:422-429.
11. Cao et al. 2005, Transplantation, 80:134-139.
12. Cao et al. 2004, Proc Natl Acad Sci USA, 101:221-226.
13. Weissleder, R. 2001, nat Biotechnol, 19:316:317.
14. Xing et al. 2005, J Am Chem Soc, 127:4158-4159.
15. Derossi et al. 1996, J Biol Chem, 271:18188-18193.
16. Derossi et al. 1996, J Biol Chem, 269:10444-10450.
17. Cirillo et al. 1991, J. Bacteriol., 173:7772-7780.
18. Rowland et al. 1999, FEMS Microbiol Lett, 179:317-325.
19. Gao et al. 2003, JACS 125:11146-11147.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A method for detecting a pathogenic Mycobacteria in real time in a subject or a biological sample, comprising:
introducing into a subject or contacting a biological sample therefrom or obtained from a surface with a fluorogenic substrate for a beta-lactamase of the pathogenic Mycobacteria, wherein the fluorogenic substrate is selected from the group consisting of CNIR800-3, XHX2-81, XHX2-91, XHX3-1, XHX3-26 and XHX3-32;
imaging the subject or sample for a product from beta-lactamase activity on the substrate; and
acquiring signals in real time at a wavelength emitted by the beta-lactamase product, thereby detecting the pathogenic Mycobacteria in the subject or the sample.

2. The method of claim 1, wherein the fluorogenic substrate is introduced into a subject and the method further comprises producing a 3D reconstruction of the emitted signal to determine location of the pathogenic bacteria in the subject.

3. The method of claim 1, wherein the fluorogenic substrate is introduced into a biological sample and the method further comprises one or both of quantifying and differentiating infected cells from non-infected cells in the biological sample.

4. The method of claim 3, wherein the steps of differentiating and/or quantifying infected cells is performed by utilizing one or more of flow cytometry, confocal microscopy and/or fluorescent spectrometry.

5. The method of claim 1 wherein the biological sample is sputum, pleural fluid, urine, blood, saliva, stool, or a sample obtained by swabbing an area of interest on the subject.

6. The method of claim 1, wherein the pathogenic bacteria comprise a *Mycobacterium tuberculosis* complex or a *Mycobacterium avium* complex.

7. The method of claim 1, wherein the imaging wavelength is from about 300 nm to about 900 nm and the emission wavelength is about 300 nm to about 900 nm.

8. The method of claim 7, wherein the imaging wavelength is about 540 nm to about 730 nm and the emission wavelength is about 650 nm to about 800 nm.

* * * * *